United States Patent
Nagasaki et al.

(10) Patent No.: US 6,278,797 B1
(45) Date of Patent: Aug. 21, 2001

(54) APPARATUS FOR INSPECTING LAND-ATTACHED CIRCUIT BOARD

(75) Inventors: Masato Nagasaki; Tomoyoshi Tsunekawa, both of Aichi; Yoichi Matsubara; Akira Kotagiri, both of Nagano, all of (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 0 days.

(21) Appl. No.: 09/160,586

(22) Filed: Sep. 25, 1998

(30) Foreign Application Priority Data

Jun. 5, 1998 (JP) .................................................. 10-158074

(51) Int. Cl.$^7$ ............................. G01B 11/00; G06K 9/20
(52) U.S. Cl. ...................... 382/146; 382/147; 382/154; 250/559.34
(58) Field of Search .................................. 382/145, 146, 382/147, 149, 150, 151, 154; 348/87, 94, 126, 130; 250/559.23, 559.31, 559.34, 559.35, 559.39, 559.45; 356/239.4, 239.5, 375, 376, 386, 601, 612, 614, 640, 237.4, 237.5; 702/40, 82, 159, 166, 169, 172

(56) References Cited

U.S. PATENT DOCUMENTS

| | | | |
|---|---|---|---|
| 5,134,665 | * | 7/1992 | Jyoko .................................... 382/8 |
| 5,299,268 | * | 3/1994 | Amir ..................................... 382/8 |
| 5,384,711 | * | 1/1995 | Kanai et al. ........................ 364/489 |
| 5,906,309 | * | 5/1999 | Hashimoto et al. ..................... 228/9 |
| 6,017,424 | * | 1/2000 | Shibuya et al. ................. 204/157.15 |

FOREIGN PATENT DOCUMENTS 6-167322   6/1994   (JP) .............................. G10B/11/24

* cited by examiner

Primary Examiner—Leo Boudreau
Assistant Examiner—Brian P. Werner
(74) Attorney, Agent, or Firm—Foley & Lardner

(57) ABSTRACT

An inspection beam such as laser beam is scanned two-dimensionally on an inspection surface of a circuit board with a plurality of lands while allowing its reflected beam from the inspection surface to be received by a beam receiving section. The beam receiving section is formed by a device, such as a semiconductor position sensitive detector, which is capable of producing an output which varies according to a reflected beam brightness and reflected beam receiving position (which reflects the height level of the reflection surface). On the basis of the output of the beam receiving section, reflected beam brightness information and height level information at respective positions on the inspection surface are prepared. From the reflected beam brightness information at the respective positions, an existing region of each of the lands on the inspection surface can be fixed. From the height level information at the respective positions within the thus fixed land existing region, the land height level can be fixed.

32 Claims, 51 Drawing Sheets

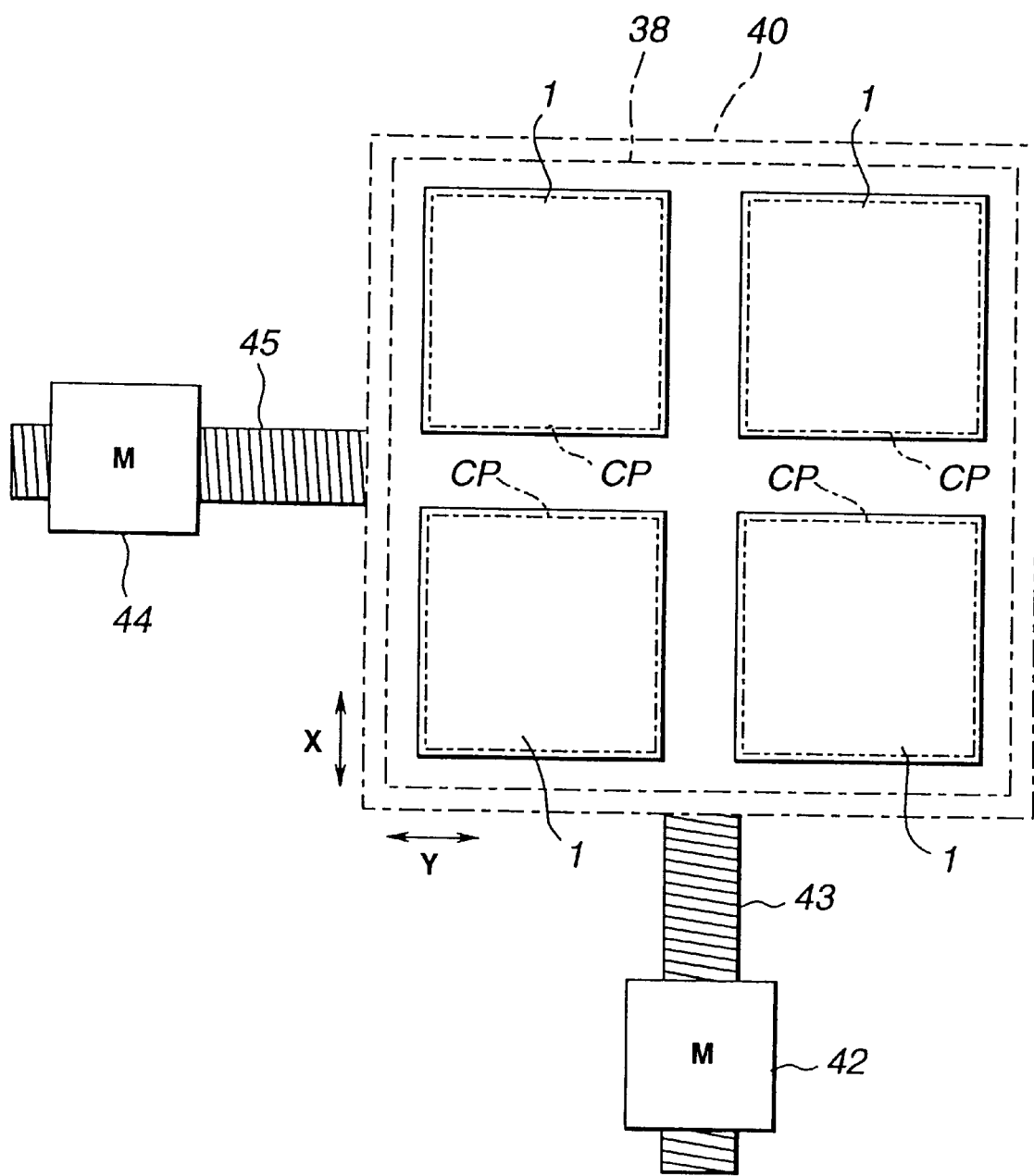

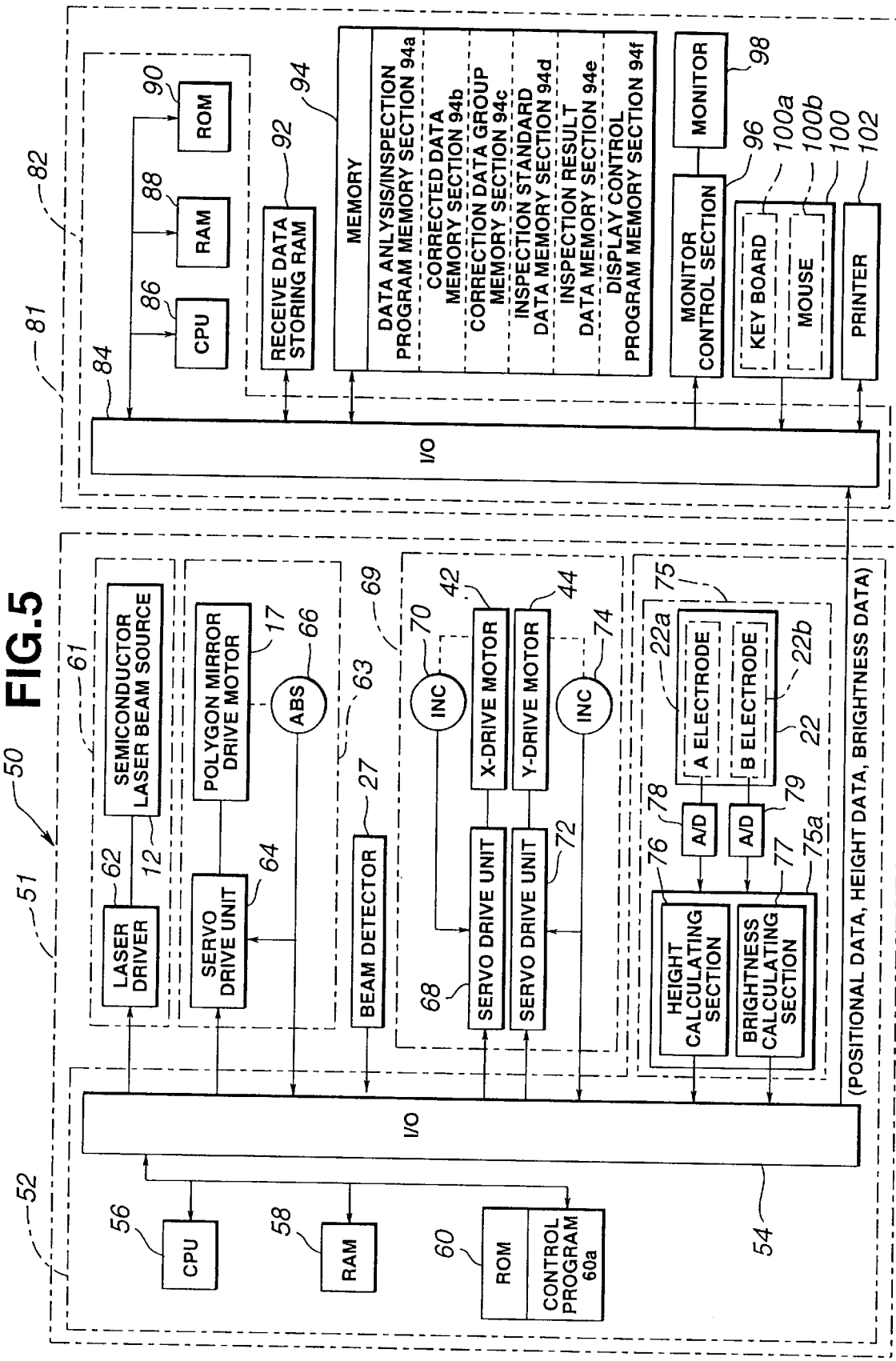

$\phi = 180° - 2\theta$ $\Delta b = L\cos\theta / \sin\phi$

FIG.10

CORRECTION DATA GROUP MEMORY SECTION 94c

| LASER BEAM INCIDENT ANGLE ($\theta$) |
| --- |
| SURFACE INCLINATION CORRECTION DATA |
| BRIGHTNESS THRESHOLD VALUE ($I_{SH}$) |

| SURFACE 1 | SURFACE 2 | SURFACE 3 |
| --- | --- | --- |
| $\Delta d_1$ | $\Delta d_2'$ | $\Delta d_3'$ |

FIG.11
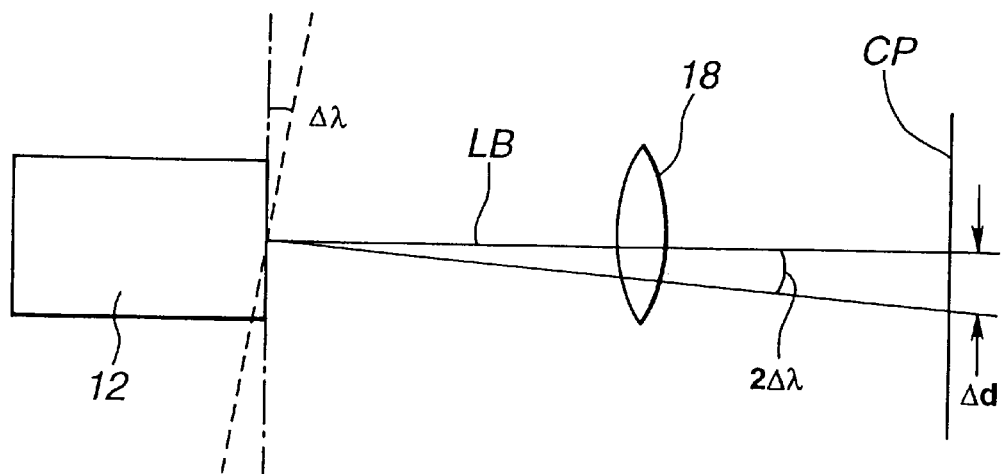
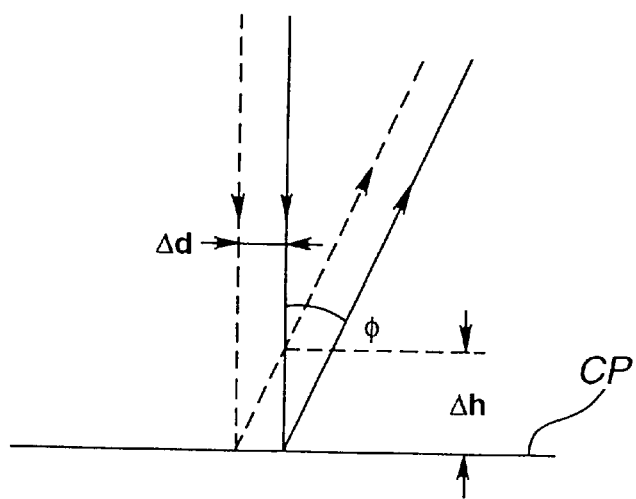

FIG.13A

|   |   |   |   |   |   |   |   |
|---|---|---|---|---|---|---|---|
| 5 | 5 | 5 | 3 | 5 | 5 | 5 | 5 |
| 5 | 5 | 5 | 2 | 3 | 5 | 5 | 5 |
| 5 | 5 | 3 | 2 | 2 | 2 | 5 | 5 |
| 5 | 3 | 3 | 2 | 2 | 2 | 3 | 5 |
| 3 | 2 | 3 | 2 | 2 | 2 | 2 | 3 |
| 5 | 5 | 2 | 2 | 2 | 3 | 5 | 5 |
| 5 | 5 | 5 | 3 | 2 | 5 | 5 | 5 |
| 5 | 5 | 5 | 5 | 2 | 5 | 5 | 5 |

HEIGHT DATA

FIG.13B

|   |   |   |   |   |   |   |   |
|---|---|---|---|---|---|---|---|
| 3 | 3 | 3 | 5 | 3 | 3 | 3 | 3 |
| 3 | 3 | 3 | 7 | 7 | 3 | 3 | 3 |
| 3 | 3 | 8 | 8 | 8 | 8 | 3 | 3 |
| 3 | 7 | 8 | 8 | 8 | 8 | 7 | 3 |
| 5 | 7 | 8 | 8 | 7 | 8 | 7 | 5 |
| 3 | 3 | 7 | 8 | 8 | 7 | 3 | 3 |
| 3 | 3 | 3 | 8 | 8 | 3 | 3 | 3 |
| 3 | 3 | 3 | 5 | 3 | 3 | 3 | 3 |

BRIGHTNESS DATA
(THRESHOLD VALUE : 7)

FIG.13C

|   |   |   |   |   |   |
|---|---|---|---|---|---|
|   |   | 2 | 3 |   |   |
|   | 3 | 2 | 2 | 2 |   |
| 3 | 3 | 2 | 2 | 2 | 3 |
| 2 | 3 | 2 | 2 | 2 | 2 |
|   | 2 | 2 | 2 | 3 |   |
|   |   | 3 | 2 |   |   |

LAND EXISTING
REGION

LAND CENTER $G(x, y)$ $$= \left( \frac{1}{NT} \sum_{i=1}^{N} x_i, \frac{1}{NT} \sum_{i=1}^{N} y_i \right)$$

REFERENCE AREA ( NUMBER OF BITS ) $S_0$
$LA_1$ : $S_1 > S_0$     $LA_3$ : $S_3 > S_0$     $LA_5$ ·· 1BIT
$LA_2$ : $S_2 > S_0$     $LA_4$ : $S_4 < S_0$     $LA_6$ ·· 2BITS $LA_4$ ( EXCLUDED FROM OBJECT FOR LAND CENTER SETTING )

$LA_5$ ( DISREGARDED )
$LA_6$ ( DISREGARDED )

LAND DIAMETER $D = 2r_m$ $$r_m = \frac{1}{N}\sum_{i=1}^{N} r_i$$

FIG.21A
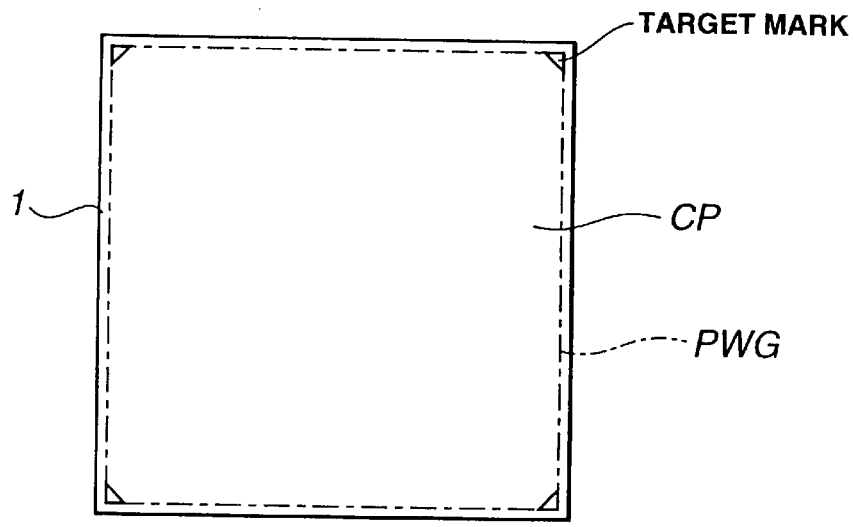
FIG.21B
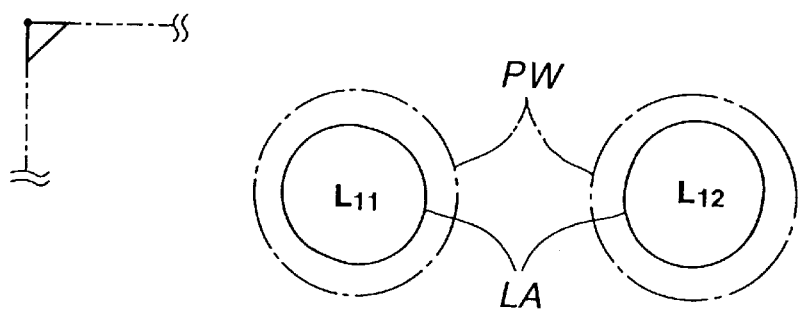
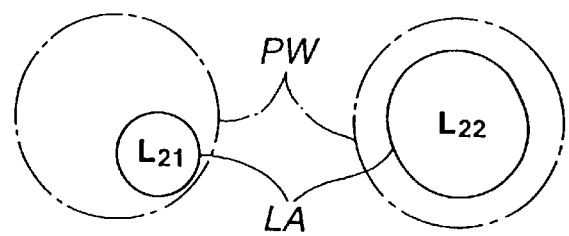
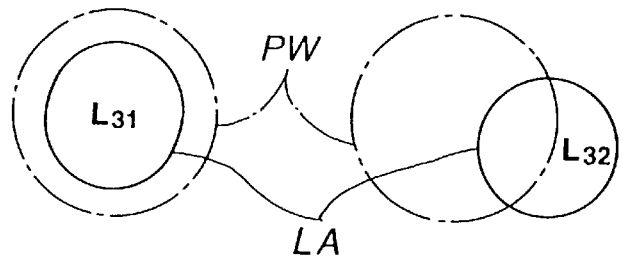

FIG.22
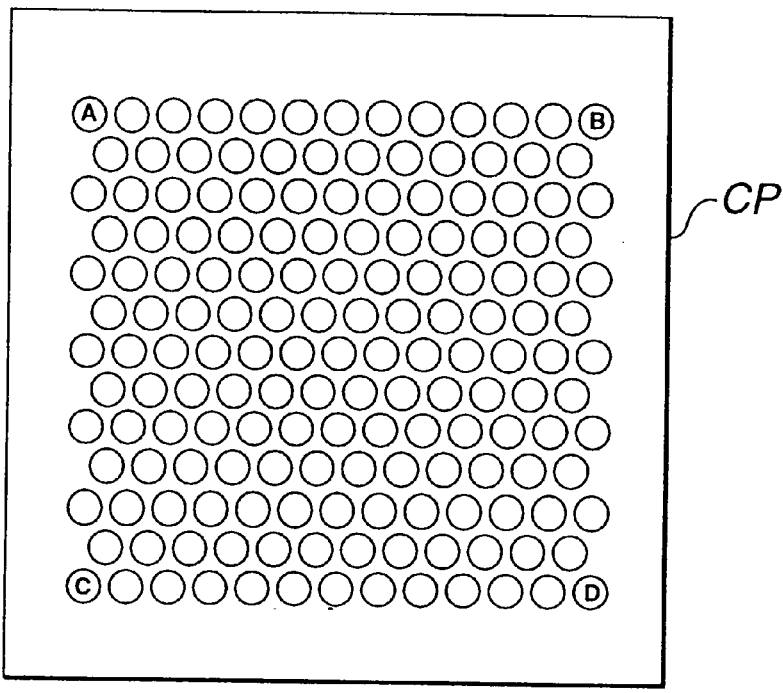
WAVINESS VALUE : $T_A = \dfrac{1}{N} \sum\limits_{i=1}^{N} T_{mi}$
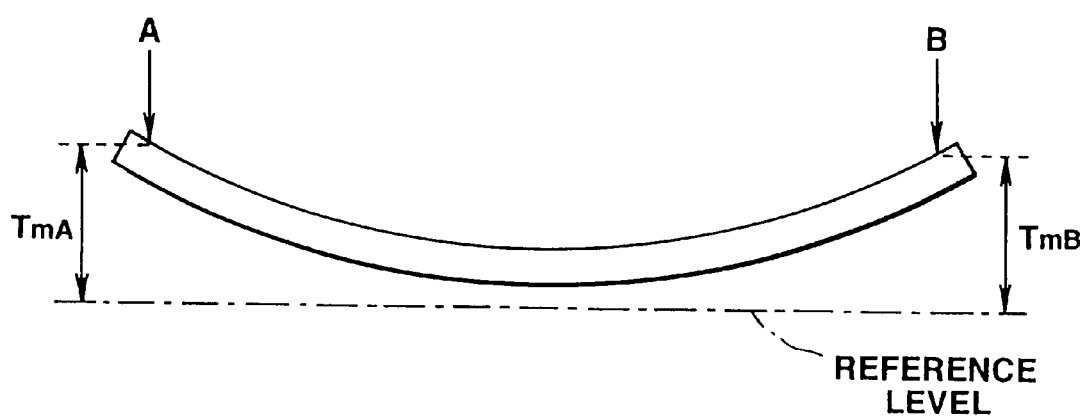
WAVINESS VALUE : $T_A = \dfrac{T_{mA}+T_{mB}+T_{mC}+T_{mD}}{4}$

FIG.33
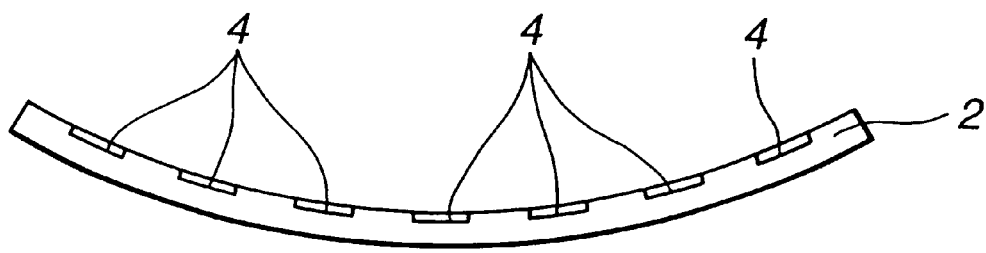
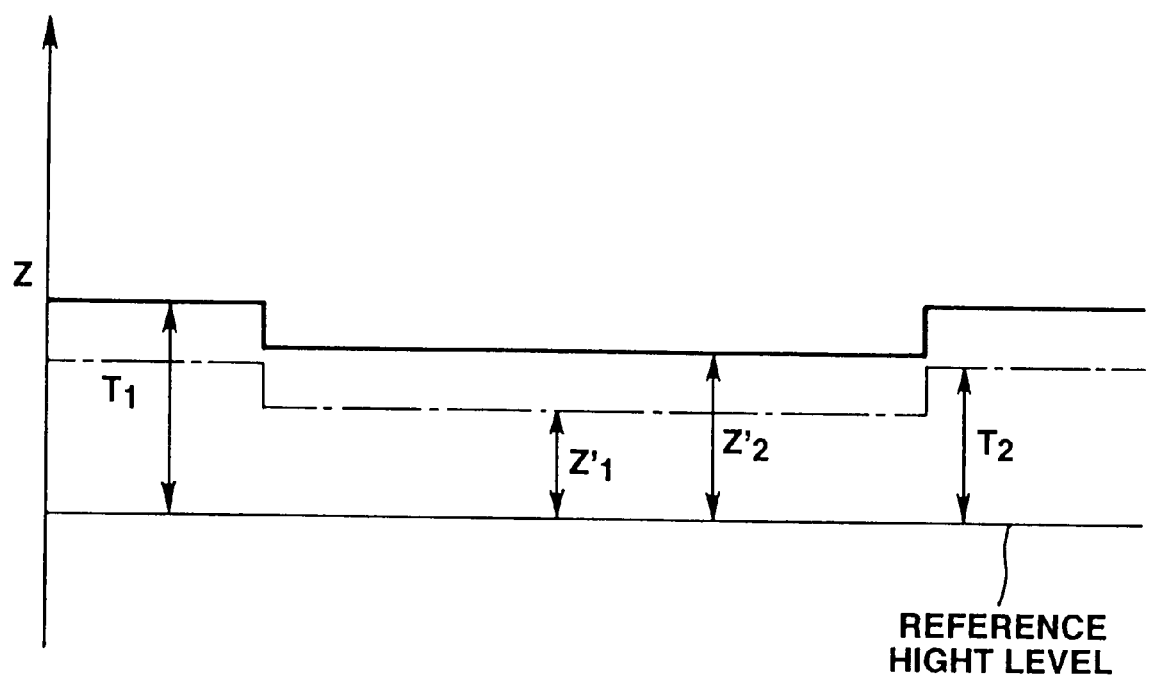
REFERENCE HIGHT LEVEL

FIG.40
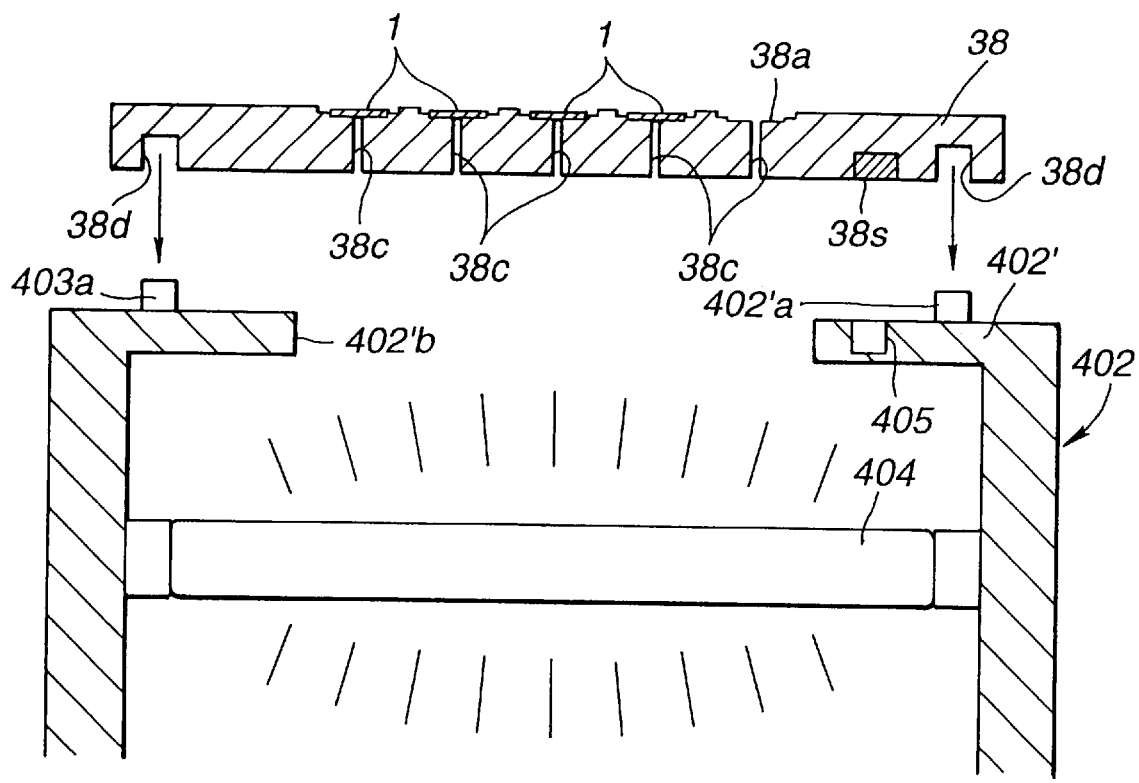
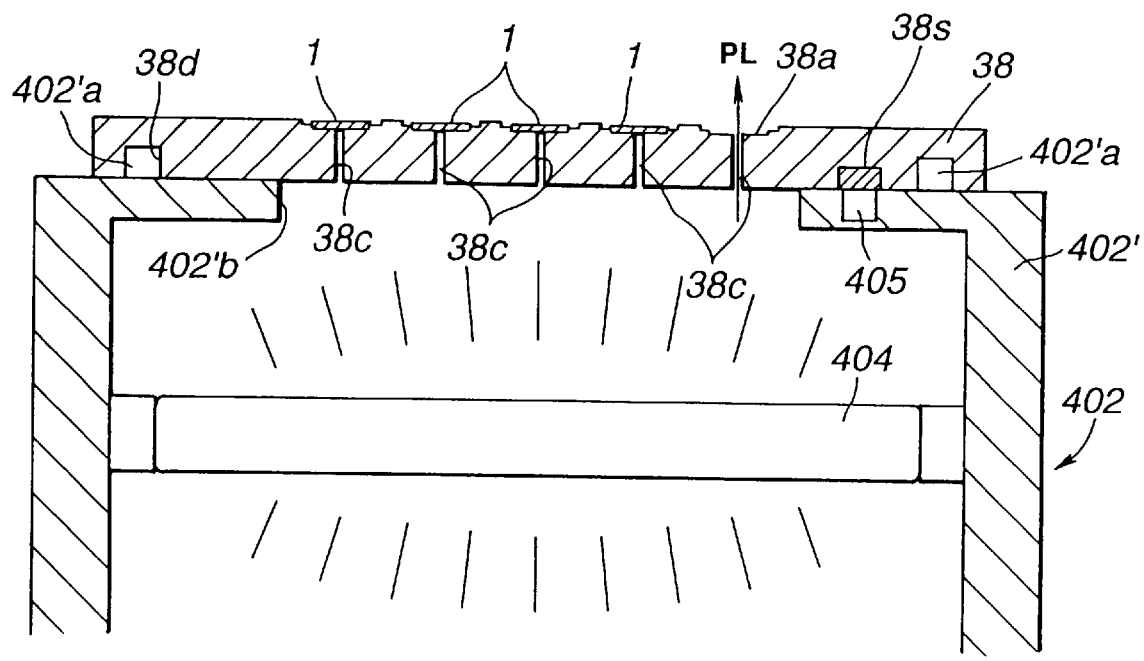

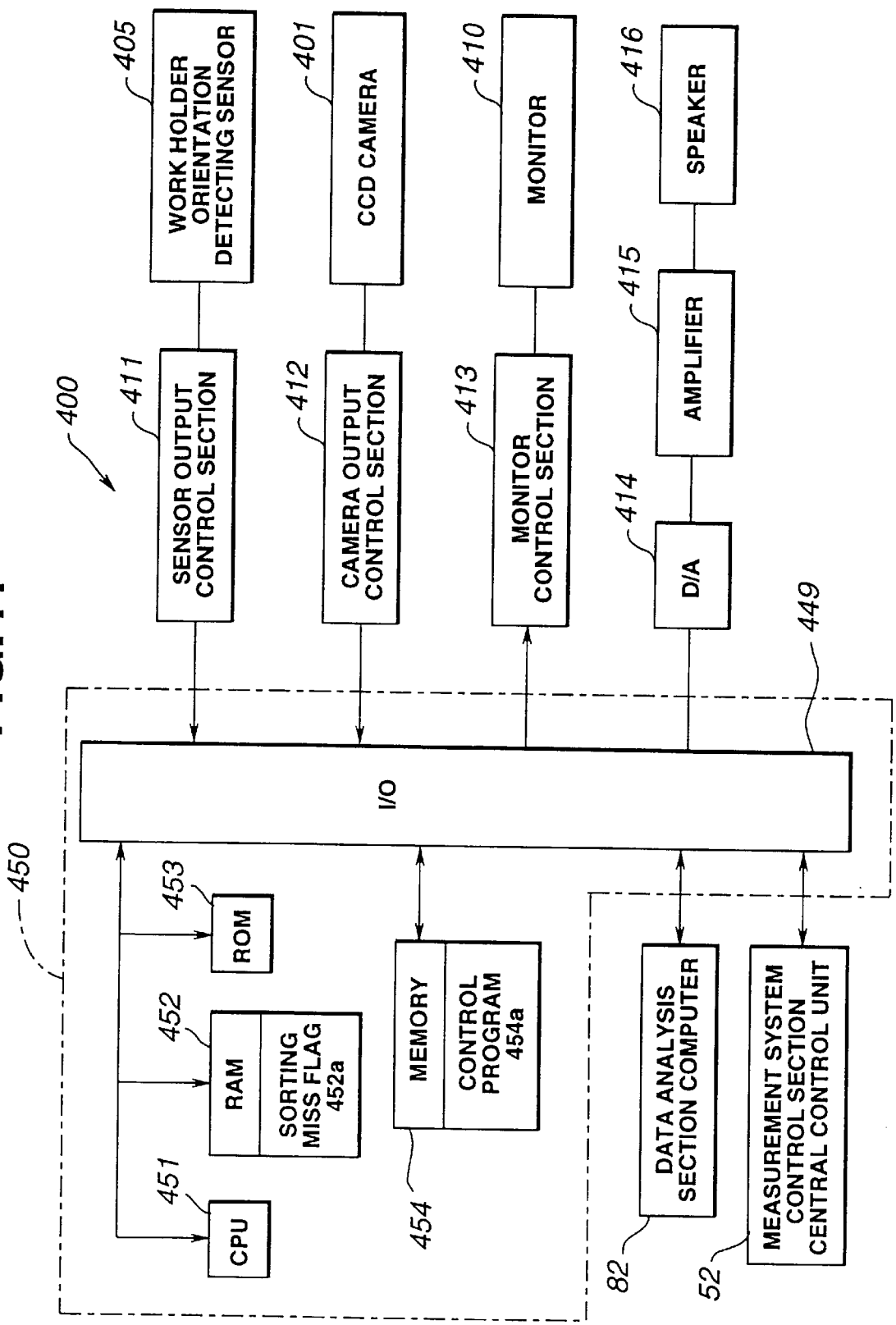

MASTER IMAGE

LAND EXISTING REGION

SET MASTER OUTPUT VALUE

| $m_{11}$ | $m_{12}$ | $m_{13}$ | ... |
|---|---|---|---|
| $m_{21}$ | $m_{22}$ | $m_{23}$ | |
| $m_{31}$ | $m_{32}$ | $m_{33}$ | |
| ⋮ | | | |

SET LAND EXISTING REGION OUTPUT VALUE

| $w_{11}$ | $w_{12}$ | $w_{13}$ | ... |
|---|---|---|---|
| $w_{21}$ | $w_{22}$ | $w_{23}$ | |
| $w_{31}$ | $w_{32}$ | $w_{33}$ | |
| ⋮ | | | |

$$\sum_{i,j} |m_{ij} - w_{ij}| \Rightarrow \text{MINIMUM}$$

APPARATUS FOR INSPECTING LAND-ATTACHED CIRCUIT BOARD

BACKGROUND OF THE INVENTION

1. Field of the Invention

The present invention relates to an apparatus for inspecting a substrate or circuit board on which is arranged two-dimensionally a plurality of terminal pads or contact pads (herein referred to as lands) for electrical connection with a chip or another circuit board (circuit board provided with lands being herein referred to as "land-attached circuit board").

2. Description of the Related Art

In recent years, there is an increasing tendency that integrated circuit chips, such as microprocessor chips and computer chips are becoming higher in the density of integration and rapidly increasing in the number of input/output terminals. Such a chip is connected to a printed circuit board such as a motherboard by way of a flip-chip connecting board. The number of lands formed on the front surface of the connecting board is several hundreds at the minimum and several thousands at the maximum. Further, on the rear surface of the connecting board are formed a number of lands which correspond in position to the respective lands of a matching printed circuit board for connecting the connecting board to the printed circuit board by means of solder balls, etc. In this connection, if the lands formed on the substrate are, for example, not in place or not uniform in the height level of the surface thereof due to waviness, warping, bending, etc., there arises a problem in that a defective connection may possibly occur to cause a malfunction of an integrated circuit, so strict inspection of the lands is necessitated.

Heretofore known as the most popular inspecting technique for inspecting the formed condition of each land of such a land-attached circuit board, is an inspection technique of picking up a rear surface side image of the board by means of a CCD camera or the like and making a judgement on whether the formed condition of each land is good or not, on the basis of the picked-up image. However, such an inspection technique based on the picked-up image has a disadvantage in that it can never obtain information on land surface height distribution though it can carry out inspection of the position, area, etc. of the land with ease. In this connection, it is considered to first carry out measurement of land area or other dimensions on the basis of the picked-up image and then carry out inspection of height distribution by using a known laser height measurement technique such as a knife edge technique and confocal technique. However, such inspection and measurement require a laser height measurement apparatus and an inspection apparatus for inspection on the basis of a picked-up image, respectively and separately, thus resulting in an increased cost of the apparatus. Further, by the known laser height measurement technique, it takes several seconds to measure the surface height level of one land (hereinafter referred to as land height level). Thus, in case of the board having a great number of lands, it takes a time ranging from several tens of minutes to several hours to measure the heights of all the lands on one circuit board, so it is actually impossible to carry out 100% inspection of mass-produced circuit boards.

SUMMARY OF THE INVENTION

According to an aspect of the present invention, there is provided a novel and improved apparatus for inspecting a circuit board with a plurality of lands disposed on one side of a circuit board substrate two-dimensionally, which side has at a place other than a place provided with the lands an exposed portion constituting a background surface which is different in reflectance from a surface of each of the lands. The apparatus comprises a measurement system which includes:

a beam source for supplying an inspection beam onto an inspection surface of the circuit board, the inspection surface including a surface region where the lands are disposed;

a beam receiving section for receiving a reflected beam resulting from the inspection beam and reflected from the inspection surface, and producing a detection output which varies according to a reflected beam brightness and a reflected beam received position at the beam receiving section;

beam scanning means for scanning the beam within the inspection surface two-dimensionally;

height level information preparing means for preparing height level information which is information on height level at respective positions within the inspection surface, on the basis of the detection output reflecting the reflected beam received position at the beam receiving section; and reflected beam brightness information preparing means for preparing reflected beam brightness information which is information on the reflected beam brightness at respective positions on the inspection surface.

The apparatus further comprises:

land existing region fixing means for fixing, within the inspection surface, land existing regions where the respective lands exist, on the basis of the difference in the reflected beam brightness represented by the reflected beam brightness information, between the background surface and the surface of each of the lands;

inspection information preparing means for preparing inspection information including land height level information which is information relating to surface height levels of the respective lands, on the basis of the height level information at respective positions within the land existing regions fixed by the land existing region fixing means; and inspection information output means for outputting the inspection information prepared by the inspection information preparing means.

An object to be inspected by the present invention is a circuit board which has an exposed side surface between lands (i.e., background surface), which exposed side surface is different in reflectance with respect to an inspection beam from a surface of each land. Specifically, a substrate for the circuit board is made of a resinous material such as a high polymer material, a ceramic material or the like. A surface portion of the land is constituted by a metallic layer such as a gold-plated layer. Thus, the surface of the land constitutes a high reflectance region, whereas the background surface portion made of a resinous material such as a high polymer material constitutes a low reflectance region.

In the above described inspection apparatus, the beam such as a laser beam is scanned two-dimensionally on the inspection surface of the circuit board with the lands while allowing its reflected beam from the inspection surface to be received by the beam receiving section. The beam receiving section is formed by a device, such as a position sensitive detector (PSD), which is capable of producing an output which varies according to the reflected beam brightness and reflected beam received position (which reflects the height level of the reflection surface). On the basis of the output of the beam receiving section, the reflected beam brightness information and height level information at respective positions on the inspection surface are prepared. From the reflected beam brightness information at the respective positions, the existing region of each of the lands on the inspection surface can be fixed. From the height level information at the respective positions within the thus fixed land existing region, the land height level can be fixed. That is, by the use of a single inspection apparatus, it becomes possible to detect the information on the land existing region, and the size, area, formed position, etc. of the land. Further, inspection of height levels of a number of lands can be carried out rapidly by two-dimensional scanning of an inspection beam.

In the meantime, in case the circuit board substrate is made of a high polymer material or a ceramic material whose outer surface is lower in reflectance with respect to the inspection beam than the surface of each land (i.e., low reflectance material), the land existing region fixing means can fix the land existing regions by regarding the regions which enable detection of a reflected beam brightness level equal to or higher than (or beyond) a predetermined threshold. value which is set so as to be higher than a reflected beam brightness level at a surface of the low reflectance material, as the land existing regions. On the other hand, in case a high polymer material or a ceramic material whose color tone is relatively light (i.e., high reflectance material), it can possibly occur such a case in which its reflectance is reversely higher than that of the background surface. In this instance, the land existing region fixing means fixes the land existing regions by regarding the regions which enable detection of a reflected beam brightness level equal to or lower than (or below) a predetermined threshold value which is set so as to be lower than a reflected beam brightness level at a surface of the low reflectance material, as the land existing regions.

Further, the reflectance of the inspection beam such as a laser beam with respect to the surface of a material can generally be changed by changing the angle of polarization. The angle of polarization of the inspection beam can be changed by the use of a polar screen or by changing a beam source (e.g., frequency). For example, in many cases, the surface of the land has small irregularities in order to mount a solder ball on each land at the time of connection of a land-attached circuit board to a printed circuit board such as a motherboard. In such a case, the difference in the reflectance with respect to the inspection beam between the land and the background surface is small. Thus, by setting the angle of polarization of the inspection beam such as a laser beam to such a value that can attain a larger difference in the reflectance between them, the land existing regions can be fixed with higher accuracy.

Then, the inspection information preparing means can be structured so as to prepare land size information reflecting an area and/or other dimensions (generally called a bulk or size) of each of the lands on the basis of an area and/or other dimensions of corresponding one of the land existing regions. By this, the inspection information on the average size of the lands can be obtained.

Further, the inspection information preparing means can comprise land center calculating means for calculating a geometric center of gravity of each of the land existing regions and determining the calculated geometric center of gravity as a center of corresponding one of the lands. In this instance, as the inspection information, information on the coordinates of the center of the land can be produced. By this, the position of the center of the land can be obtained accurately.

In the meantime, the land center calculating means can be constructed so as to calculate a point of intersection of diagonal lines of a quadrilateral region (e.g., rectangular region) circumscribed about each of the land existing regions, and determine the calculated point of intersection as a center of corresponding one of the lands. For example, a method of calculating a center of gravity as representing a center of a land, is more accurate among center determining methods but requires to use coordinate values of a number of brightness data constituting a high brightness region at the time of calculation, so that the number of operations is a little larger. However, in case of the method of obtaining a quadrilateral region circumscribed about the land existing region (and a point of intersection of diagonal lines) as described above, its operation is far easier as compared with an operation for obtaining coordinates of a center of gravity, thus making it possible to make higher the processing speed.

Each of the land existing regions can be fixed by means of an image which is displayed by collective pixels disposed on a pixel plane corresponding to the inspection surface. In this instance, a master image corresponding in shape to each of the land existing regions and reflecting an area and/or other dimensions of each of the land existing regions is prepared, whereby the land center calculating means can be structured so as to select a position of the master image on the basis of the number of pixels which correspond to only one of the image of each of the land existing regions and the master image and calculating a geometric center of gravity of the master image at the selected position and determining the calculated geometric center of gravity as a center of corresponding one of the lands. The master image can be determined as a circle with the same area as the land existing region or a circle which is obtained from any three points on a boundary between the land existing region and a background surface. In case the circle obtained from any three points on that boundary is used as the master image, the calculation process is relatively easy so improvement in the process speed can be attained.

In the meantime, the image of each land existing region and the master image can be formed by a combination of a plurality of substantial or imaginary pixels in output states, which pixels are capable of being set to intermediate output. In this instance, the land center calculating means can be structured so as to select a position of the master image on the basis of the sum of difference in set output value between corresponding pairs of the pixels of the image of each of the land existing regions which is an object to be inspected and the master image (e.g., so as to select a position so that the sum of the absolute values of the difference of the set output values is minimum) and calculating a geometric center of gravity of the master image at the selected position and determining the calculated geometric center of gravity as a center of corresponding one of the lands. By this, the image of the land existing region and the master image can match with higher accuracy, thus making it possible to fix the position of the land existing region with higher accuracy and therefore make higher the inspection accuracy. In the meantime, the substantial pixel is used to indicate a pixel of an output device of a monitor or a printing machine. The output state of the pixel of such an output device, even if the output device does not actually exist or the output device is not used, can be fixed or specified as an output state of an output information of each pixel stored in a memory cell. In this specification, a pixel whose output value is fixed or defined only in a memory under a condition where an output device does not exist or an output device is not used, is called an imaginary pixel.

The land existing region fixing means can be structured so as to fix the land existing regions by regarding, within the inspection surface, regions which enable detection of a reflected beam brightness equal to or higher than a predetermined threshold value which is set so as to be higher than a reflected beam brightness level at a surface of the low reflectance material, as the land existing regions. In this instance, the inspection information preparing means can be structured so as to produce inspection information including at least information on height of the lands corresponding to the land existing regions, on the basis of information on height at respective positions within the land existing regions.

With this structure, the regions of the inspection surface of the land-attached circuit board, which exhibit a reflected beam brightness equal to or higher than a threshold value, are fixed as high brightness regions, and only those of the high brightness regions that have an extent of space equal to or larger than a criterion area are recognized as land existing regions. That is, since the extent of space of each of the high brightness regions is defined two-dimensionally to be processed, so there is not any possibility of mistaking two or more height level data resulting from one high brightness region for those resulting from different lands, thus resultantly making it possible to perform inspection of a circuit board provided with any kind of lands accurately and rapidly. As a result, even in the case of a land which is formed with a depression at the outer surface, it can be recognized assuredly on the basis of an extent of space of a high brightness region. Further, there may occur such a case in which the high brightness region originating from one land is separated into two or more sections. In this instance, since a high brightness region which is of such an area smaller than a criterion area is not regarded as a land existing region, it is hard to occur such a trouble that the above two sections are regarded as two lands, thus resultantly making it possible to identify a plurality of lands formed on a circuit board accurately.

The inspection information preparing means can be structured so as to include land height level calculating means for calculating the land height levels on the basis of information on height level at respective positions within the land existing regions. In this instance, the land height level calculating means can be structured so as to calculate one of an average height level which is obtained by averaging height levels at respective positions within each of land height level determining height brightness regions, a maximum height level which is a maximum of the height levels at the respective positions, a minimum height which is a minimum of the height levels at the respective positions and a most frequent height which is the most numerous one of the height levels at the respective positions, and determines calculated one of them as a height level of corresponding one of the lands. By this, rational judgment or evaluation of the land height level can be performed. Further, according to the necessity, two or more of the above described average level, maximum level and minimum level (e.g., average height and maximum height) are calculated and evaluation can be performed based on a combination of them, whereby yet more accurate evaluation of the land height level can be attained.

On the other hand, the above described inspection apparatus can be structured so as to include background height level determining region setting means for setting, at locations outside of the respective land existing regions, background height level determining regions for obtaining the height level of the background surface around each of the lands, and background height level calculating means for calculating a height level of each of the lands on the basis of the information on height level at respective positions within each of the background height level determining regions.

By this, the height level of every portion of the background surface around each of the lands can be obtained with ease. For example, in the event that the circuit board substrate is constructed of a high polymer material, there may possibly occur such a case in which the height level of the background surface and therefore the height level of the surface of the land varies from position to position largely to cause waviness or warping of the circuit board surface due to the difference in the coefficient of thermal expansion between the metal constituting the metallic wiring inside the circuit board substrate and the high polymer material when the circuit board is subjected to heating during a manufacturing process, leading to defective connection of the circuit board. Thus, by obtaining the height level information as described above, it becomes possible to make a judgment on whether such a defect occurs in a circuit board to be inspected, with ease.

The above described background height level calculating means can also be structured so as to calculate one of an average height level which is obtained by averaging height levels at respective positions within each of background height level determining regions, a maximum height level which is a maximum of the height levels at the respective positions, a minimum height which is a minimum of the height levels at the respective positions and a most frequent height which is the most numerous one of the height levels at the respective positions, and determines calculated one of them as a height level of corresponding portion of the background surface.

The inspection information preparing means can be structured so as to include surface waviness information preparing means for preparing surface waviness information reflecting a waviness condition of the background surface on the basis of the height levels, which height levels are calculated by the background height level calculating means, of the background surface at the background height level determining regions which are set at different positions on the inspection surface. In this structure, the information on the waviness of the circuit board substrate is obtained on the basis of the information on the height level of the background surface, thus enabling an inspection having the more sides or aspects.

The apparatus can be structured so as to include position tolerance defining window setting means for setting, in regard to the inspection surface, a plurality of position tolerance defining windows each of which defines a tolerance of a position where each of the lands is formed, area calculating means for calculating an area of each of the land existing regions within each of the set position tolerance defining windows or an area proportion at which each of the land existing regions occupies each of the position tolerance defining windows, and judgment means for judging whether each of the lands corresponding to each of the position tolerance defining windows is in a state of being formed good or not, on the basis of the area or the area proportion of each of the land existing regions calculated by the area calculating means. By this, a defective land which is moved out of place or incomplete in shape due to chipping or the like can be recognized with ease on the basis of judgment on whether the land existing region within the position tolerance defining window has an area equal to or larger than a predetermined value.

In the meantime, the inspection beam can be cast onto the inspection surface while holding the circuit board in place by means of a circuit board holder. In this instance, the land height level calculating means can be structured so as to calculate a height level of each of the lands above a reference height level having a constant relation with a circuit board holder and determines the calculated height level as the height level of corresponding one of the lands. The inspection information preparing means can be structured so as to include coplanarity information preparing means for preparing coplanarity information reflecting an irregularity of heights of the lands of the circuit board, on the basis of a maximum $Z'\max$ and a minimum $Z'\min$ of the height levels calculated by the land height level calculating means.

It is considered desirable that the lands disposed on the circuit board are as uniform in height level as possible in order to improve the adherence thereof to a joining object such as a printed circuit board (e.g., BGA circuit board). In this instance, a simple parameter is a difference of $Z'\max$ and $Z'\min$ ($Z'\max - Z'\min$) and it means that as the difference becomes smaller the lands become more uniform in height level, so it can serve as an indicator for indicating the irregularity of the lands.

In this invention, an indicator for indicating the irregularity of the height levels of the lands, which is calculated not only by the above described $Z'\max - Z'\min$ but by the use of $Z'\max$ and $Z'\min$ is referred to in a broad sense as coplanarity. For example, there can be employed in this embodiment, other than $Z'\max - Z'\min$, various indicators such as a coplanarity in a narrow sense which is defined by the distance between planes Pmax and Pmin wherein it is assumed that a least squares plane corresponding to the top position of each land (in case of a flat land a predetermined place on the top face of the land, for example, the place on the top face corresponding to the above described center of the land) is a top reference surface P0, Pmax is a plane parallel to the top reference surface P0 and in contact with the top of the land which is maximum in height, and Pmin is a plane parallel to the top reference surface P0 and in contact with the top of the land which is minimum in height.

Further, a coplanarity per unit length, which is obtained by dividing the above described distance serving as an indicator by the distance LD between a remotest pair of lands among a number of lands formed on the circuit board (e.g., in case the lands are arranged in the form of matrix so as to constitute a rectangular or square region in which they are arranged, the distance between the pair of lands located on the opposite ends of a diagonal line of the rectangular or square region) can be used. In any case, by the provision of the above described coplanarity information preparing means, it becomes possible to evaluate the coplanarity of the land-attached circuit board easily.

Then, in the above described inspection apparatus, the information output means can be structured so as to include height level distribution display means for causing a display device to produce a mapping output representing a height level distribution on the inspection surface by dividing a range of height level by one or more threshold values and associating divided range sections of height level with respective depths and/or colors of each of pixels of the display device one to one for thereby associating depths and/or colors of pixels corresponding to the respective positions on the inspection surface with height levels at the respective positions, which are indicated by the height level information.

That is, a mapping output of inspection information, i.e., the height levels at the respective positions within the inspection surface of the land-attached circuit board is supplied to the display device in such a manner that different heights are indicated by different depths or colors, so the height distribution within the inspection surface is visualized and can be grasped very intuitively, whereby it becomes possible to obtain information on the position and height level of each land and the information on warping, waviness or the like of the circuit board substrate with accuracy.

The inspection information preparing means can be structured so as to include land defect information preparing means for preparing information reflecting a defect within each of the land existing regions, on the basis of the reflected beam information at respective positions within the land existing regions. For example, by providing a predetermined threshold value to the reflected beam brightness at the respective positions within each of the land existing regions, a defective region can be fixed by regarding a region that exhibits a brightness equal to or lower than the threshold value, as the defective region.

In the above described structure, land defect information for use as inspection information is prepared on the basis of reflected beam brightness information at respective positions on the surface of each of the lands. By this, judgement on a defect such as oxidation of a surface of a land, defective plating and flaw can be made with ease. Further, by a combination with the height level distribution display means, oxidation of a surface of a land, i.e., a defect caused by a factor other than height level can be grasped with ease.

Then, the apparatus can be structured so as to comprise land quality judging means for judging good/no good of each of the lands on the basis of whether the formed condition of each of the lands, which reflects on the inspection information, satisfies a predetermined judgment condition or not, and defective land position display control means for controlling so that the display device displays an existing position of a defective land which is judged, on a mapping output display (hereinafter will be sometime referred to as "mapping display") of the height distribution, as being defective by the land quality judging means. That is, in case a defective land is detected in the middle of inspection, it is displayed on the mapping output display of the height distribution so that it becomes possible to grasp rapidly and accurately where it is located within the inspection surface and what kind of defect is caused.

In this connection, the apparatus can be structured so as to comprise defective land existing region selecting means for selecting, on the mapping output display of the height distribution, the existing region of the defective land whose position is indicated, and defective land existing region enlarged display means for displaying an enlarged mapping image of a height distribution of the selected defective land existing region. Thus, by enlarging the condition of the defective land on the mapping display, it becomes possible to grasp the detail of the defect by visual enlargement, and therefore analysis of the cause of the defect or the like can be attained with ease.

The defective land position display control means can be structured so as to display, on the mapping output display of the height distribution, a region of a predetermined area including the defective land existing region for use as an enlargement designating region. In this instance, the defective land existing region selecting means can be structured so as to select the defective land existing region by using the enlargement designating region as a unit for selection of the defective land existing region, and the defective land existing region enlarged display means can be structured so as to display while enlarging a mapping image within the selected enlargement designating region. By this, the enlarged display process is carried out by taking the enlargement designating region displayed on the mapping output display as a unit, so it is easy to associate the display region in a low magnification state and the display region in a high magnification state with each other, and therefore it is easy to grasp where the existing enlarged display is located within the entire inspection surface.

In this connection, the defective land existing region selecting means can be structured so as to select the enlargement designating region by moving, on the mapping output display, a pointer which is displayed on the mapping output display by an operation of a pointing device and placing a position indicated by the pointer within the enlargement designating region while executing, under such a condition, a region selection command. By this, it becomes possible to carry out a selection operation on the mapping output display of the defective land existing region quite intuitively.

The defective land position display control means can be structured so as to set the enlargement designating region in such a manner that the enlargement designating region includes a plurality of land existing regions. In this instance, the apparatus can further comprise individual land selection region setting means for setting a region of a predetermined area including only optional one of the individual land existing regions within the enlargement designating region, as an individual land selection region, and individual land mapping image enlarged display means for displaying while further enlarging a mapping image within the set individual land selection region. By this, the condition of the defective land can be confirmed on the mapping output display, together with the conditions of the lands located adjacently therearound. Further, a mapping image of optional one of lands including a defective land can be displayed individually and in an enlarged scale, so it becomes possible to obtain more precise information on the condition of each land.

The apparatus can further comprise the inspection information content display means for displaying a content of the inspection information of one of the lands corresponding to the land existing region selected by the individual land selection region. By this, the inspection information of each land on the mapping image is visualized by numerical values or the like, so it is easy to measure and grasp the formed condition of each land. Further, the apparatus can comprise pixel selecting means for selecting optional one of pixels constituting the mapping image within the individual land selection region, and detection information-by-position display means for displaying a content concerning at least one of the height information and the reflected beam information and corresponding to a position on the inspection surface, which is indicated by the selected pixel. By this, it becomes possible to measure the height or the reflected beam brightness at the respective positions within the land existing region.

Further, the apparatus can comprise a work holder for detachably holding thereon a plurality works which are arranged on a plane, each of the works being a land-attached circuit board which is an object for inspection, and work holder drive means for driving said work holder to move relative to the beam source for thereby moving the arranged works sequentially into an inspection position to which the inspection beam is cast. In this instance, the measurement system can be structured so as to perform detection of height at respective positions within an inspection surface of each of the works which are moved into the inspection position, and the inspection information preparing means prepares inspection information of each of the works on the basis of corresponding one of the height information. By this structure, it becomes possible to inspect a plurality of works attached to the work holder one after another efficiently.

In this instance, the apparatus can further comprise work arrangement display means for displaying arrangement of the works on the work holder, work quality judging means for judging good/no good of each of the works on the basis of the inspection information, and defective work display control means for controlling the work arrangement display means and making it display, in relation to the arrangement of the works, a position of a defective work which is judged as having a defective land or lands by means of the work quality judging means. That is, as the progress of inspection, it is displayed visually which one of the work on the work holder is defective, so in case a number of works are inspected consecutively, grasp of defect is quite easy.

More specifically, the work arrangement display means can include individual work display sections which correspond one-to-one to the respective works on the work holder. In this instance, the defective work display control means can be structured so as to cause the work arrangement display means to display the position of the defective work by making those of the individual work display sections corresponding to a defective work and a normal work different in a display condition from each other. By this, it becomes easier to recognize the position of a defective work in the arrangement of the work.

Further, the apparatus can comprise measurement system operation control means for suspending a measurement operation of the work holder drive means and the measurement system in case a work is judged as being defective by the work quality judging means in the middle of detection of the height at the respective positions within the inspection surface, which is carried out sequentially for the works. That is, when a defective work is found during an inspection process, it is desired, in many cases, to confirm the condition or the like of the defective work on the spot for thereby fixing a factor that has caused the defect or for the like purpose. In this instance, by the above structure the inspection process is automatically stopped temporarily, so it is easy to obtain the time for recognition of the above matter or the like.

In case a work holder is subjected to an inspection process as a unit, it is desirable, when a defective work is found, to remove the defective work from the work holder as quickly and certainly as possible for the purpose of preventing a defective article from being included in a lot of articles (or for some reason, there can be such a case in which a normal (good) work is removed from the work holder). Thus, the apparatus can comprise work quality judgment result display means for displaying a result of judgment on whether each of the works on the work holder is a defective work or normal work, work detecting means for detecting individually whether the works are attached to respective work attaching positions on the work holder, sorting result judging means for judging whether a work sorting operation is carried out correctly or not, on the basis of a detection content of the work detection means with respect to the work holder which is subjected to a work sorting operation for removing a defective work and leaving a normal work, while looking at a display content of the work quality judgment result display means, and judgment result output means for outputting a result of judgment by the sorting result judging means.

By this, it becomes possible to manually sort or select defective works and good works while looking at the display of the work good/no good judgment result. Then, it is automatically judged by the sorting result judging means whether the sorting condition is good or not. When there occurs a sorting miss, a suitable judgment result output is produced for the process onward, so it becomes possible to prevent a defective article from being erroneously included in the lot of articles, effectively.

In this instance, by providing the inspection apparatus with warning output means for outputting a warning by means of a sound, line or a combination thereof, in response to an output of a judgment result from the judgment result output means when a work sorting operation is not carried out correctly, an oversight of a sorting miss is hard to occur and an effect of preventing erroneous inclusion of defective article can be further heightened.

Specifically, the work detecting means can be structured so as to detect whether the works are attached to the work attaching positions, with respect to the work holder in a state of being removed from said measurement system. By this, it becomes possible to remove the work holder having finished inspection and measurement, to the outside of the measurement system and carry out sorting of a defective work or works, so during the time or such sorting it becomes possible to carry out inspection of a new work, thus making it possible to maker higher the inspection efficiency. In this instance, the apparatus can further comprise measurement system operation control means for controlling the work holder drive means and the measurement system in a way as to inhibit them from performing a measurement operation for a next work holder, in response to an output of a judgment result from the judgment result output means in case the work sorting operation is not carried out correctly. That is, if inspection of the following works is carried out continuously without solving the sorting miss, it becomes high the possibility that a defective work or works are included in the lot of articles. Thus, by constructing, as in the above structure, so that the operation of the work holder drive means and the measurement system for the following work holder (works) is inhibited until the sorting miss condition is cancelled or eliminated, such a drawback can be overcome quite rationally.

The work holder can be formed with a plurality of work attaching portions in which the works are installed respectively, and each work attaching portion can be formed with a light transmitting portion (such as a through hole). In case the work attaching portion is formed into a depression, the above described light transmitting portion can be formed at the bottom of the depression. In this instance, the work detecting means can include a sorting light source for illuminating the work holder from a lower side thereof and leaking light detecting means disposed on a side of the work holder opposite to the sorting light source for detecting a leaking light from the light transmitting portion at each of the depressions, so that the work detecting means can detect whether the works are installed in or attached to the respective work attaching portions (depressions) on the basis of existence of the leaking light. That is, with the above structure, depending upon whether the light transmitting portion is covered or closed by the work, it becomes possible to detect whether a work exists within the work attaching portion assuredly.

On the other hand, the work detecting means can comprise a light casting section for casting a light toward each work attaching portion on the work holder, and a reflected light detecting section for detecting a reflected light reflected from the work which is attached to the work attaching portion, so that the work detecting means can detect whether a work is attached to each work attached portion on the basis of existence of the reflected light. That is, with this structure, it becomes possible to detect whether a work exists within the work attaching portion on the basis of existence of a reflected light with ease and accuracy.

The above structure is effective for solving the above noted problems inherent in the prior art apparatus.

It is accordingly an object of the present invention to provide a novel and improved apparatus for inspecting a land-attached circuit board which, by itself, can inspect a height level as well as a size, area and formed of each land rapidly.

BRIEF DESCRIPTION OF THE DRAWINGS

FIG. 4 is a schematic plan view of an x-y table of the inspection apparatus of FIG. 2;

FIG. 5 is a block diagram of a control system of the inspection apparatus of FIG. 2;

FIG. 10 is an illustration of a content of data stored in a correction data group memory section of the control system of FIG. 5;

FIG. 11 is an illustration of movement of a position on a scanning surface onto which a laser beam is to be cast or thrown and its measurement error, respectively;

FIGS. 13A to 13C are illustrations of land existing regions in a state of being represented by the use of bit map data;

FIGS. 21A and 21B are illustrations of a method of estimating existence of a defective land;

FIG. 22 is an illustration of a method of calculating a waviness value;

FIG. 33 is an illustration of an influence of a height level of a circuit board substrate on measurement of a land height level;

FIG. 40 is a sectional view for illustration of an internal structure of a beam source box and its operation;

FIG. 41 is a block diagram of an electrical structure of the sorting unit of FIG. 39;

DETAILED DESCRIPTION OF THE PREFERRED EMBODIMENTS

Figure 1A:
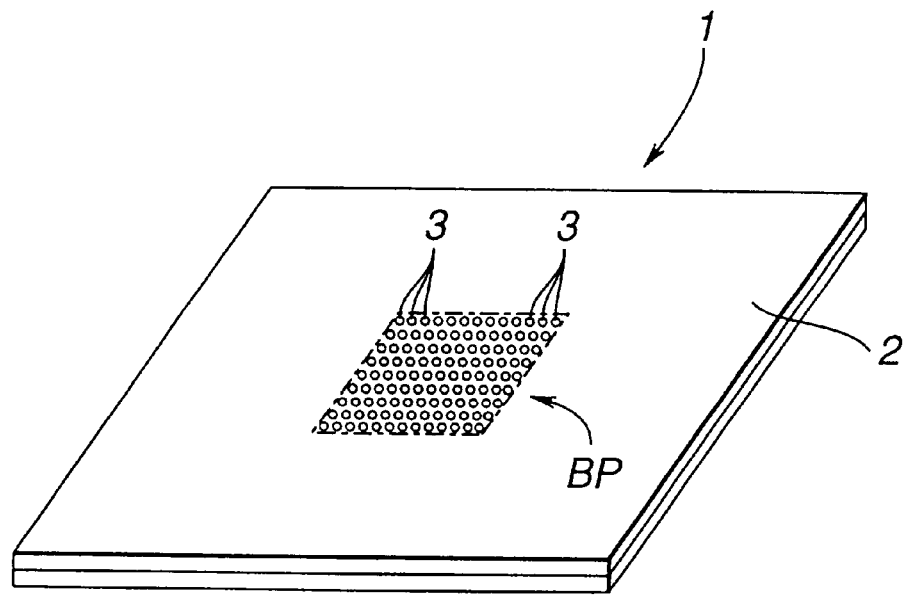
FIGS. 1A and 1B are perspective views of a front surface side and rear surface side of a land-attached circuit board which is an object to be inspected by an inspection apparatus of the present invention, respectively.
Figure 1B:
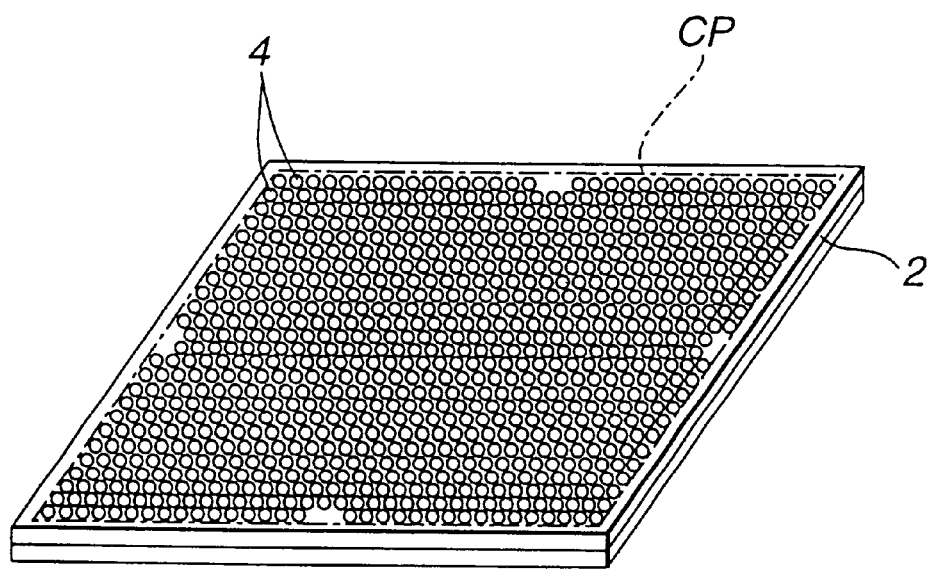

FIG. 1 shows by way of example a land-attached circuit board 1 which is an object to be inspected by an inspection apparatus of the present invention. The land-attached circuit board 1 is constructed as a flip chip circuit board and includes a substrate 2 which is, for example, made of a resinous material such as high polymer (which may be a ceramic material) and is about 25 mm square and about 1 mm thick. The substrate 2 has at a central portion thereof a bump arranged region BP which is for example square. At the bump arranged region BP are disposed a number of solder bumps 3 made of a brazing alloy such as Sn-Pb binary alloy. The bumps 3 are arranged in a two-dimensional array such as a grid pattern or checkered pattern and fixedly attached to the substrate 2. Further, at the rear surface side of the substrate 2 are similarly formed and arranged in a two-dimensional array such as a grid pattern or checkered pattern a number of lands 4 (e.g., circular when observed in a plan view) corresponding to the respective bumps 3. The lands 4 are electrically connected to the corresponding bumps 3 at the front surface side by way of a wiring pattern (not shown) disposed within a circuit board substrate 2.

Figure 6:
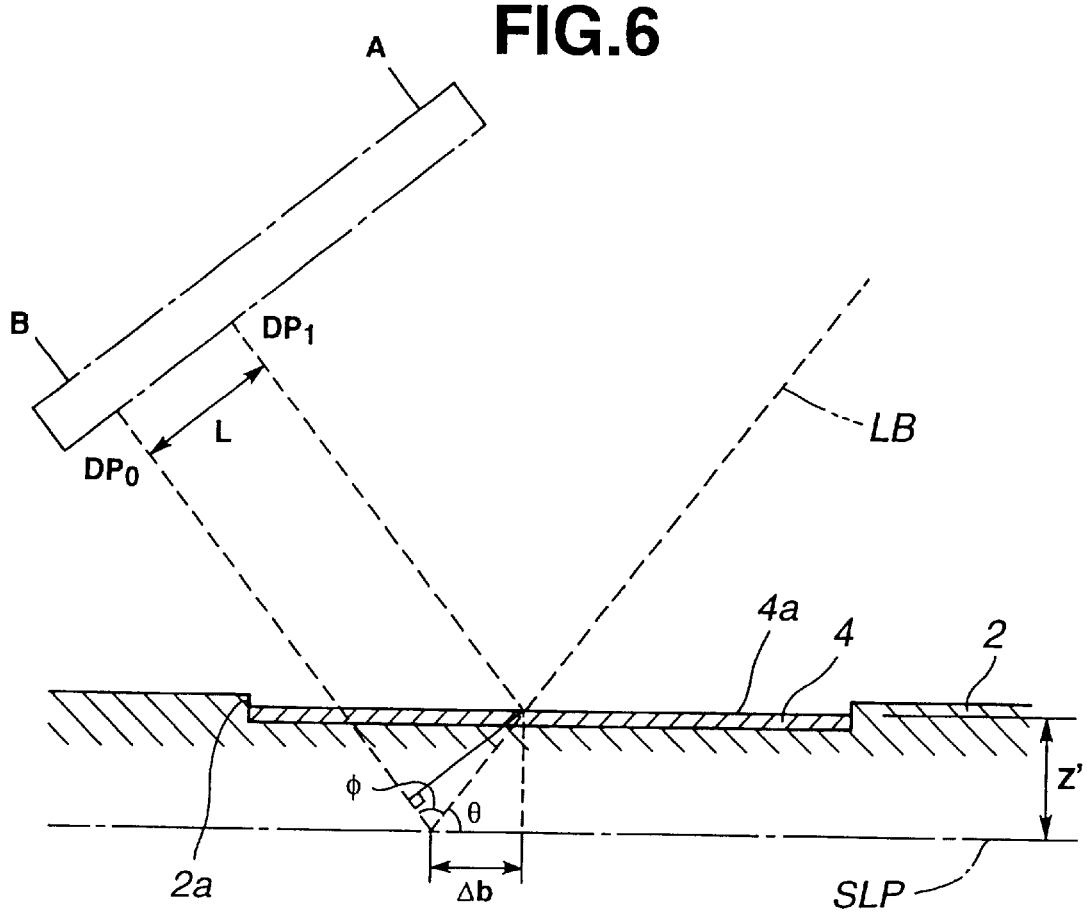
FIG. 6 is an illustration of a principle of the method of detecting a height level by the use of a laser beam.

In this embodiment, as shown in FIG. 6, the circuit board substrate 2 has at the rear surface side a shallow depression 2a for each land 4. Each land 4 is disposed in the depression 2a and has a multi-layer structure consisting of an electroless Ni-P-plated layer and an electroless Au-plated layer covering the Ni-P-plated layer. In the meantime, at the rear surface portion of the substrate 2 where no land 4 is disposed, there is formed a solder resist layer (not shown) which is made of acrylic resin, epoxy resin or the like. In this connection, the surface of each land 4 has small irregularities for mounting thereon a solder ball so it has a metallic luster though a little lackluster. On the other hand, the substrate 2 is made of a resinous material, so the surface of the land 4 is higher in the reflectance with respect to visible light (i.e., laser beam serving as inspection beam which will be described hereinlater) than the surface of the substrate 2. Further, the angle of polarization of the inspection beam such as a laser beam can be changed by the use of a polar screen or by changing a beam source. By this, the reflectance of the inspection beam with respect to the surface of the object to be inspected can be changed. Since the surface of the land 4 has small irregularities and has a metallic luster though a little lackluster, the difference in the reflectance with respect to the inspection beam between the land 4 and the background surface is small. In this instance, by setting the angle of polarization of the inspection beam such as a laser beam to such a value that can attain a larger difference in the reflectance between them, it becomes possible to make higher the accuracy with which discrimination between the land 4 and its background is made.

Figure 2:
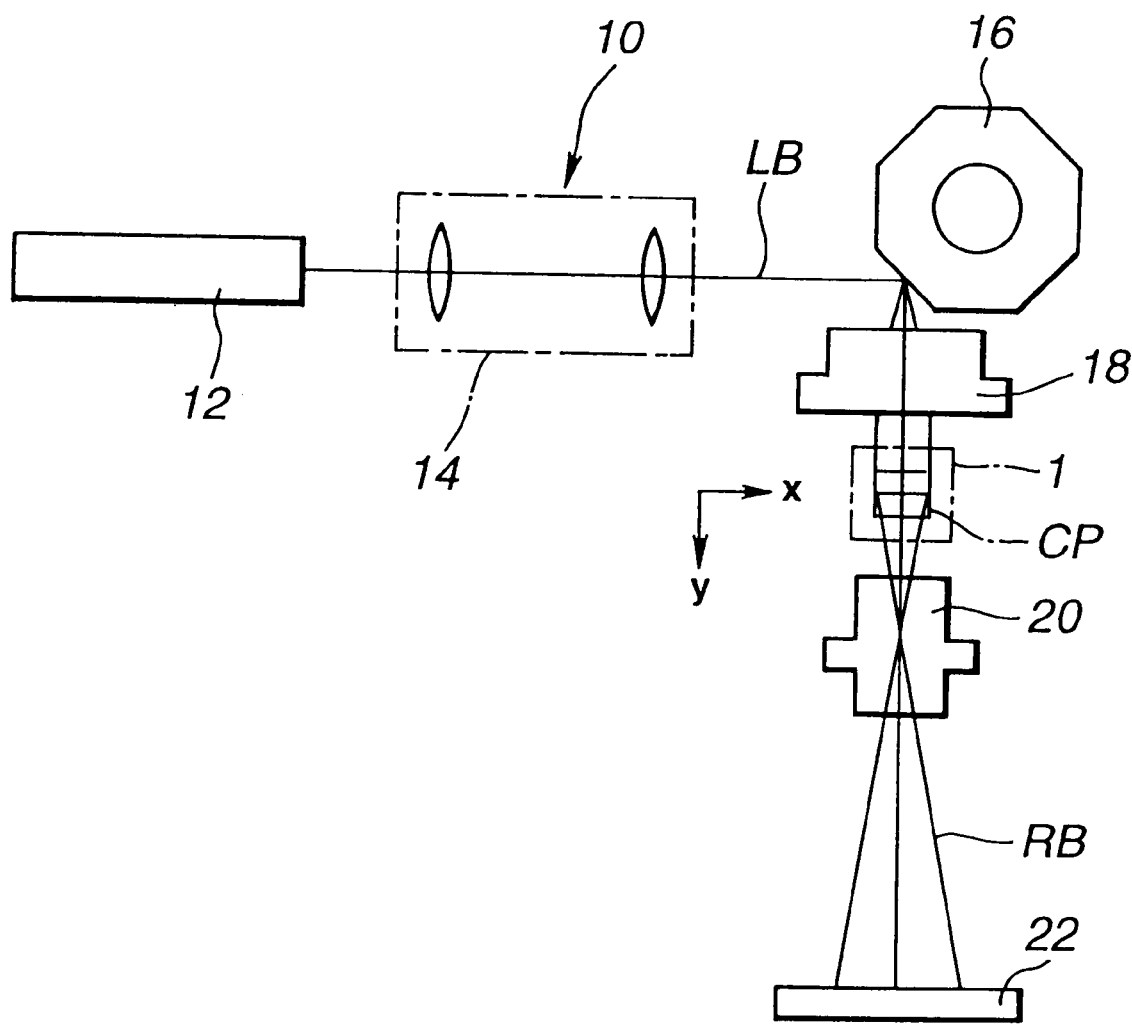
FIG. 2 is a schematic view of an important portion of a measurement system of an inspection apparatus according to an embodiment of the present invention.

FIG. 2 schematically shows an important portion of a measurement system 10 of an inspection apparatus according to an embodiment of the present invention. The measurement system 10 consists of a semiconductor laser beam source 12, a beam expander 14, a polygon mirror 16, an f·θ lens 18, an image formation lens 20, and a semiconductor position sensing device (PSD) 22 at a beam receiving section. A laser beam (incident beam) LB transmitted from the laser beam source 12 is reflected by the rotating polygon mirror 16 and irradiated or cast onto the inspection surface CP of the land-attached circuit board 1 in FIG. 1, which inspection surface CD is set so as to include the area for arrangement of the lands 4 in lengthwise and breadthwise arrays, while being caused to swing along either of a lengthwise array or breadthwise array of lands (hereinafter referred to as x-direction). The incident laser beam LB thus cast is reflected by the inspection surface CP and transmitted therefrom as a reflected beam RB to be received by the PSD 22 by way of the image formation lens 20.

Figure 3B:
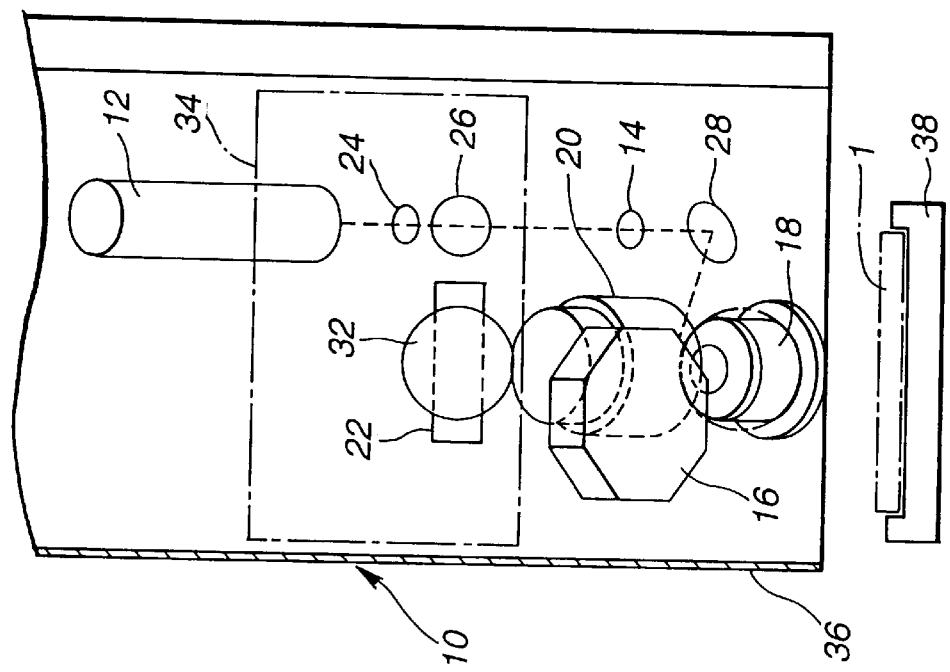
FIG. 3B is a schematic, rear elevational view of the specific structural example of FIG. 3A.
Figure 3A:
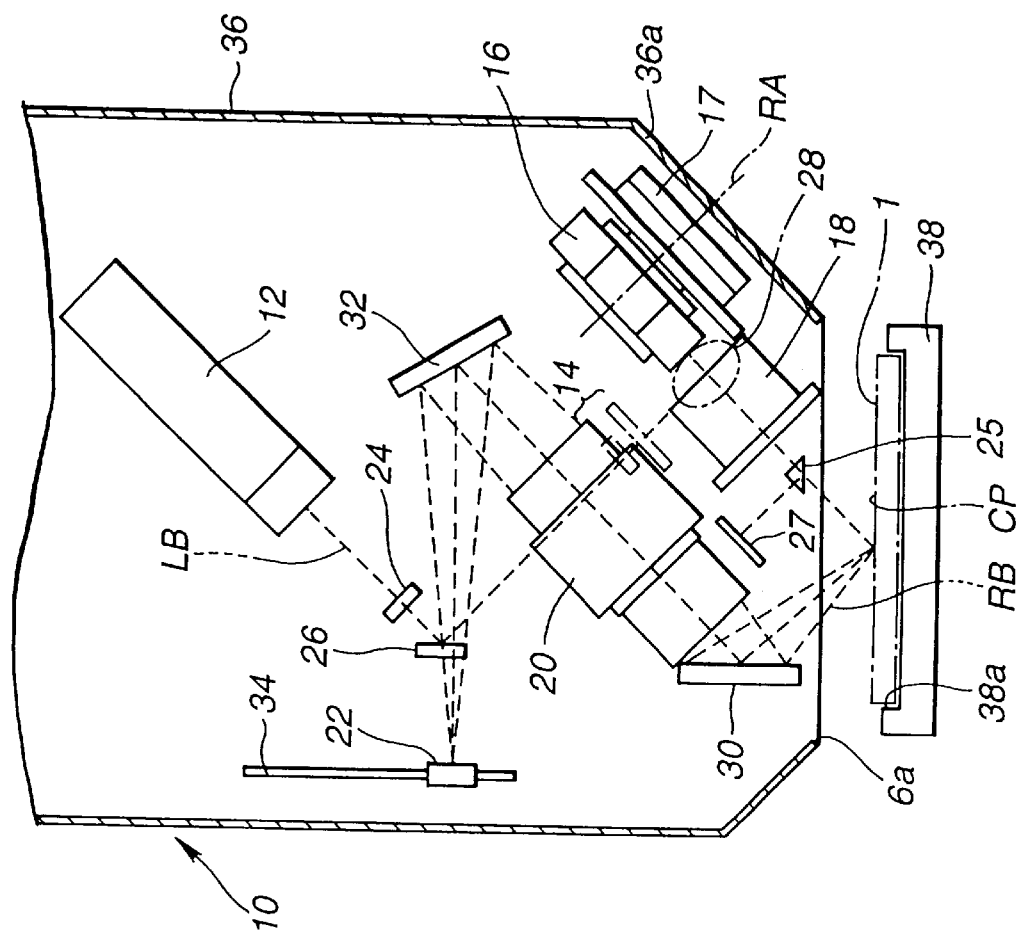
FIG. 3A is a schematic, side elevational view of a specific structural example for the measurement system of FIG. 2.

FIGS. 3A and 3B show a specific structural example of the measurement system 10, in which FIG. 3A is a side elevation and FIG. 3B is a rear elevation. In this structure, as shown in FIG. 3B, the semiconductor laser beam source 12 is disposed within a vertically elongated case 36 in a way as to be positioned at an upper portion thereof. As shown in FIG. 3A, the semiconductor laser beam source 12 emits from a beam hole formed in the lower end face thereof a laser beam LB forward and downward thereof. The laser beam LB is transmitted through a collimator lens 24 and reflected by an optical path changing mirror 26 backward and downward. The laser beam LB is then transmitted through a beam expander 14 disposed on an optical path and reflected by a second optical path changing mirror 28 sideways and upward as shown in FIG. 3B.

The laser beam LB reflected by the second optical path changing mirror 28 is incident onto the polygon mirror 16 disposed a little upper sideways of the second optical path changing mirror 28. As shown in FIG. 3A, the polygon mirror 16 is disposed within the casing 36 and has an axis RA of rotation which is attached to an inclined wall 36a at the lower back of the polygon mirror 16 in a way as to incline upward as it extends forward. The laser beam LB reflected by the polygon mirror 16 is transmitted through the f·θ lens 18 disposed diagonally under the polygon mirror 16 and an opening 6a formed in the bottom wall of the casing 36 and incident onto the inspection surface CP of the land-attached circuit board 1 (hereinafter referred to as work) which is disposed under the opening 6a and held horizontally by a work holder or circuit board holder 38.

The laser beam LB is reflected forward and upward from the inspection surface CP and transmitted as a reflected beam RB. The reflected beam RB is then reflected backward and upward by a third optical path changing mirror 30 which is disposed in front of the f·θ lens 18 and nearly vertically. The reflected beam RB is transmitted through the image formation lens 20 which is disposed diagonally above and in front of the f·θ lens 18, then reflected forward by a fourth optical path changing mirror 32 which is disposed diagonally above the polygon mirror 16, and finally received by the PSD (semiconductor position detector) 22 which is disposed at the front and inside of the casing 36.

In this instance, a first optical system group including the semiconductor laser beam source 12, the collimator lens 24 and the beam expander 14 (in this embodiment, the semiconductor laser beam source 12, the collimator lens 24, the first optical path changing mirror 26, the beam expander 14, and the second optical path changing mirror 28 which are arranged in sequence from the upper side) are disposed within the casing in a way as to be placed next to one side in the widthwise direction. On the other hand, a second optical system group including the polygon mirror 16, the f·θ lens 18, the image formation lens 20 and the semiconductor position detector 22 (in this embodiment, the polygon mirror 16, the f·θ lens 18, the third optical path changing mirror 30, the image formation lens 20, the fourth optical path changing mirror 32 and the semiconductor position detector 22) is disposed side by side, in the widthwise direction of the casing 36, with the first optical system group. The laser beam LB from the first optical system group is introduced by the optical path changing mirror 28 to the second optical system group side. By employing such a layout, it becomes possible to reduce the dead space otherwise caused within the casing 36 effectively and make the entire apparatus quite compact.

Then, the work 1 which is an object to be inspected, is mounted on a work mounting or attaching portion 38a in the form of a depression or the like formed in the work or circuit board holder 38. In this embodiment, a plurality of works 1 are mounted on one work holder 38 in such a manner as to form a matrix pattern or grid pattern. As shown in FIG. 4, the work holder 38 is detachably mounted on an x-y table 40 which is driven to move in the x-direction and y-direction independently by means of, for example, an x-drive screw shaft 43 and x-drive motor 42(hereinafter referred to as an x-drive system), and a y-drive screw shaft 45 and a y-drive motor 44 (hereinafter referred to as a y-drive system). In this instance, the y-direction is determined so as to cross at right angles the x-direction in the plane along the inspection surface CP of the work 1, i.e., in FIG. 2, the direction in which scanning with the laser beam LB is made by the polygon mirror 16 to which the laser beam LB is transmitted by way of the f·θ lens 18. In FIG. 4, by inching the table 40 with a predetermined interval in the y-direction while conducting scanning with the laser beam LB in the x-direction by means of the polygon mirror 16, the inspection surface CP is scanned with the laser beam LB two-dimensionally. Accordingly, in this embodiment, the polygon mirror 16 and the y-drive system of the x-y table 40 constitute a beam scanning means. On the other hand, the x-drive system is used, in case for example a plurality of works 1 are arranged on the work holder 38 so as to form a plurality of rows which extend in the x-direction and are located adjacent to each other, for moving the works 1 in the next row to the position to which the laser beam is cast or irradiated.

FIG. 5 shows a structural example of a control system of the inspection apparatus of the present invention. A control system 50 can be divided into two large groups, i.e., a measurement system control section 51 and a data analyzing section 81. A central control unit 52 of the measurement system control section 51 mainly consists of an I/P (input/output) port 54, and those connected to the I/O port 54, i.e., a CPU (central processing unit) 56, RAM 58, ROM 60 and a height level-brightness detecting section 75. Further, there are connected to the I/O port 54, other than those described above, a laser producing section 61, a polygon mirror operating section 63, and an x-y table operating section 69, respectively. In the meantime, the CPU 56 constitutes major or principal portions of a height level information preparing means and a reflected beam brightness information preparing means, together with a height level calculating section 76 and a brightness calculating section 77.

The laser producing section 61 consists of the semiconductor laser beam source 12 and a laser driver 62 which is responsive to an instruction from the central control unit 52 to drive the semiconductor laser beam source 12 to produce a laser beam LB. Further, the polygon mirror operating section 63 consists of a polygon mirror drive motor 17 for driving the polygon mirror 16 (refer to FIG. 3) to rotate, a servo drive unit 64 responsive to an instruction from the central control unit 52 for controlling the operation of the polygon mirror drive motor 17, and a rotary encoder (used in this embodiment is an absolute type and hereinafter abbreviated as ABS) 66 for detecting a rotation speed and an angular position of the polygon mirror drive motor 17, i.e., the polygon mirror 16. The servo drive unit 64 controls the operation of the polygon mirror drive motor 17 on the basis of a rotation speed information fed back thereto from the ABS 66. On the other hand, such an angular position detected by the ABS 66 is used as an x-coordinate determining information for determining an x-coordinate of a point to be scanned with a laser beam LB and a mirror face determining information for determining a mirror surface of the polygon mirror 16 which is in use.

The x-y table operating section 69 consists of the x-drive motor 42, y-drive motor 44, servo drive units 68 and 72 responsive to an instruction from the central control unit 52 for controlling 30 the operations of those drive motors 42 and 44, and rotary encoders (used in this embodiment is an increment type and hereinafter abbreviated as INC) 70 and 74 for detecting the angular positions of the respective motors 42 and 44. The servo drive units 68 and 72 control the respective operations of the x-drive motor 42 and the y-drive motor 44 on the basis of a rotation speed information fed back thereto from the INCs 70 and 74. Further, the angular position of the y-drive motor 44, which is detected by the INC 74, is also used as a y-coordinate determining information for determining the y-coordinate of the point to be scanned with the laser beam LB.

The height level-brightness detecting section 75 consists of the above described PSD 22, A/D converters 78 and 79 for converting outputs from respective electrodes of the PSD 22, a height calculating section 76 and a brightness calculating section 77 for calculating a height and brightness by using the outputs of the PSD 22 which are digitally converted by the A/D converters 78 and 79, and so on. Hereinlater, a principle of detecting a height level by using a laser beam will be described.

As shown in FIG. 6, a height level reference surface (i.e., a basic surface for measurement of height) SLP substantially parallel to the surface of the circuit board substrate 2 is set so that the laser beam LB is incident upon the height reference surface SLP at an incident angle θ. In this connection, if reflection takes place upon the height reference surface SLP, the PSD 22 will receive the reflected beam at a reference beam receiving position $DP_0$. However, in case reflection takes place on the substrate 2 such as the surface 4a of the land 4, the reflection surface position becomes higher by Z' so the beam receiving position is shifted or deviated to $DP_1$. The amount L of shift or deviation of the beam receiving position $DP_1$ from the reference beam receiving position $DP_0$, i.e., the height Z' of the reflection surface can be measured on the basis of the output currents IA and IB of two output terminals A and B of the PSD (position-detecting semiconductor device) 22. In the meantime, the height Z' on the basis of the height reference surface SLP will hereinlater be referred to as "height level value (or height level) Z'".

In this connection, assuming that $I_{A0}$ represents the output current of the output terminal A when the reflected beam is received at the reference beam receiving position $D_{P0}$ and similarly $I_{B0}$ represents the output current of the output terminal B, and if adjustment of the beam receiving position of the PSD is made so that $I_{A0}=I_{B0}$, the above described amount L of deviation becomes larger proportionately with $(I_A-I_B)/(I_A+I_B)$. As shown in FIG. 5, the height calculating section 76 calculates a value equivalent to $(I_A-I_B)/(I_A+I_B)$ on the basis of the information of $I_A$ and $I_B$ and outputs a height level signal representative of the calculated value. On the other hand, since the sum $I_A+I_B$ of the output currents of the both terminals of the PSD 22 becomes larger proportionately with the intensity (brightness) of the beam to be received, the brightness calculating section 77 calculates a value equivalent to $(I_A+I_B)$ similarly and outputs a brightness signal representative of the calculated value.

The above described $I_A$ and $I_B$ are amplified by voltage conversion, and an electric signal corresponding to $(I_A-I_B)/(I_A+I_B)$ is created by a calculation circuit and is produced as a height level signal. On the other hand, the sum $(I_A+I_B)$ of the output current at the both terminals of the PSD 22 becomes larger nearly in proportion to the intensity (brightness) of the light to be received, so the brightness calculating section 77 creates at a predetermined calculation circuit a signal corresponding to $(I_A+I_B)$ and transmits it as a brightness signal.

The CPU 56 of the central control unit 52 controls the operation of the laser producing section 61, the polygon mirror operating section 63 and the x-y table operating section 69 on the basis of a program 60a stored in a ROM 60 and by using a RAM 58 as a work area. On the other hand, the CPU 56 fetches from the ABS 66 an output value $X_{ABS}$ that gives an x-coordinate of a laser beam scanning position or point and from the INC 74 a pulse count value $Y_{INC}$ that similarly gives a y-coordinate in accordance with a timing given by a clock pulse (produced by a clock circuit which is not shown) and produces a positional data ($X_{ABS}$, $Y_{INC}$). At the same time, the CPU 56 fetches from the height-brightness detecting section 75 a digitized height level signal and brightness signal in sequence and produces a height level data Z" and a brightness data I corresponding to the scanning point. A set of height level data Z", brightness data I and positional data ($X_{ABS}$, $Y_{INC}$) obtained for each scanning point is transmitted from the I/O port 54 to the data analyzing section 81.

In the meantime, as shown in FIGS. 3A, a prism 25 and a beam detector 27 are provided in the place corresponding to the starting point at which scanning of the inspection surface CP in the x-direction starts and to the intermediate point of the optical path of the laser beam LB from the polygon mirror 16. The prism 25 and the beam detector 27 are provided for detecting a start timing at which data sampling-in-the x-direction of height data and brightness data on the basis of the laser beam LB starts. That is, when the laser beam LB comes to a data sampling start position on the work 1 in response to rotation of the polygon mirror 16, it is incident on the prism 25 and its branch beam is detected by the beam detector 27. In response to this, the measurement system control section 51 starts the data sampling in the x-direction.

Returning to FIG. 5, the data analyzing section 81 is mainly comprised of an I/O port 84 and an analysis computer 82 having a CPU 86, RAM 88, RCM 90, etc. which are connected to the I/O port 84. To the I/O port 84 of the computer 82 are connected a receive data storing RAM 92 for temporary storing of a set of a height level data Z", brightness data I and positional data ($X_{ABS}$, $Y_{INC}$) transmitted from the measurement system control section 51, a memory 94 made up of a hard disk or the like, a monitor control section 96, a monitor 98 connected to the monitor control section 96, an input section 100 such as a key board and mouse, a printer 102, and so on. In the meantime, the monitor 98, printer 102, etc. function as an inspection result output means. Further, the CPU 86 functions as, on the basis of a data analysis/inspection program which will be described hereinlater, a land existing region fixing means, an inspection information preparing means, a height level determining region setting means, a land height level calculating means, a height level determining high brightness region extracting means, a background height determining region setting means, a background height level calculating means, a position tolerance defining window setting means, an area calculating means, a judgment means, a land center determining means, a land arranging interval calculating means, a land size calculating means, a coplanarity information preparing means, a surface waviness information preparing means, etc.

Further, the memory 94 is provided with a data analysis/inspection program storing section 94a, a corrected data storing section 94b, a correction data group storing section 94c, an inspection standard data storing section 94d, an inspection result data storing section 94e which store corresponding programs or data, and a display control program memory section 94f, respectively. In the meantime, the contents of the respective data and the details of the program processing will be described hereinlater.

Referring to the flowchart of FIG. 23, the flow of control process at the measurement system control section 51 will hereinafter be described. Firstly, at D10, the work holder 38 having mounted thereon the work 1 is set on the x-y table 40 (refer to FIG. 4). At D20, the x-y table 40 is moved to the scanning start position for the first work. In the meantime, at the time of rising the measurement system, the starting point of the x-y table 40 is recognized by means of a starting point sensor (not shown) and hereinafter used as a criterion for various positioning processes. Then, at D40, the laser beam LB is cast upon the inspection surface CP, while at the same time it is made to start y-drive of the x-y table 40 and rotation of the polygon mirror 16. At D50, a set of the above described height level data Z", brightness data I and positional data ($X_{ABS}$, $Y_{INC}$) for each scanning point is created and transmitted to the data analyzing section 81.

In the meantime, for simplification of the analyzing process to be carried out later, the number of data to be fetched can be reduced by making the data sampling distance in the y-direction larger than that in the x-direction (or converse will do). In this instance, for making larger, for example, the data sampling distance in the y-direction, the scanning speed in the y-direction can be made larger than that in the x-direction while holding the time intervals of data sampling in the x-direction and y-direction nearly equal to each other or reversely the time interval of data sampling in the y-direction can be made longer than that in the x-direction while holding the scanning speeds in the y-direction and in the x-direction nearly equal to each other. As a further method, it will do to fetch data under the condition where data sampling distances in the x-direction and y-direction are nearly equal to each other and thin the data sets fetched in either of the x-direction or y-direction at the time of analysis so that the number of used data sets is reduced.

Then, when fetch/transmission of data for the work 1 is completed, the x-y table 40 is moved to the scanning start position of the next work (D60→D61), and the control is returned back to the step D40 to repeat thenceforth the same process steps. In this manner, the above described sets of data with respect to the row of works arranged in the y-direction are fetched in sequence. When the fetch/transmission of data for all the works arranged in that row is finished, x-drive of the x-y table 40 is carried out so that the x-y table 40 is moved to the scanning start position for the first work of the next row, and the similar process steps are repeated (D62→D63→D40). When preparation/transmission of data for all the works is completed, the process is ended.

Figure 12A:
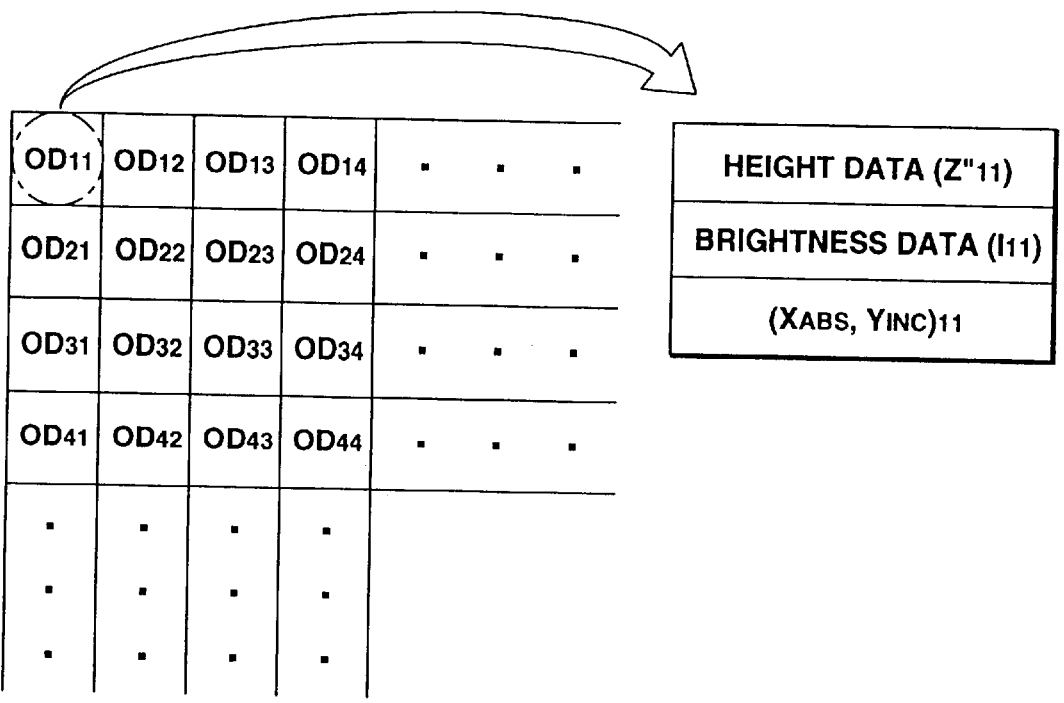
FIGS. 12A and 12B are illustrations of a content of a receive data storing RAM and a content of a corrected data memory section of the control system of FIG. 5, respectively.

On the data analyzing section 81 side, the data from the measurement system control section 51 is received and stored in the receive data storing RAM 92 (refer to FIG. 5) in such a manner that each set OD of data Z", I and ($X_{ABS}$, $Y_{INC}$) correspond to each scanning point, as shown in FIG. 12A. Hereinlater, the flow of processing on the data analyzing section 81 side will be described with reference to the flowcharts of FIGS. 24 to 33. In the meantime, it is the CPU 86 of the computer 82 (refer to FIG. 5) that executes the process on the basis of the data analysis/inspection program stored in the memory 94 and by using the RAM 88 as a work area.

Figure 24:
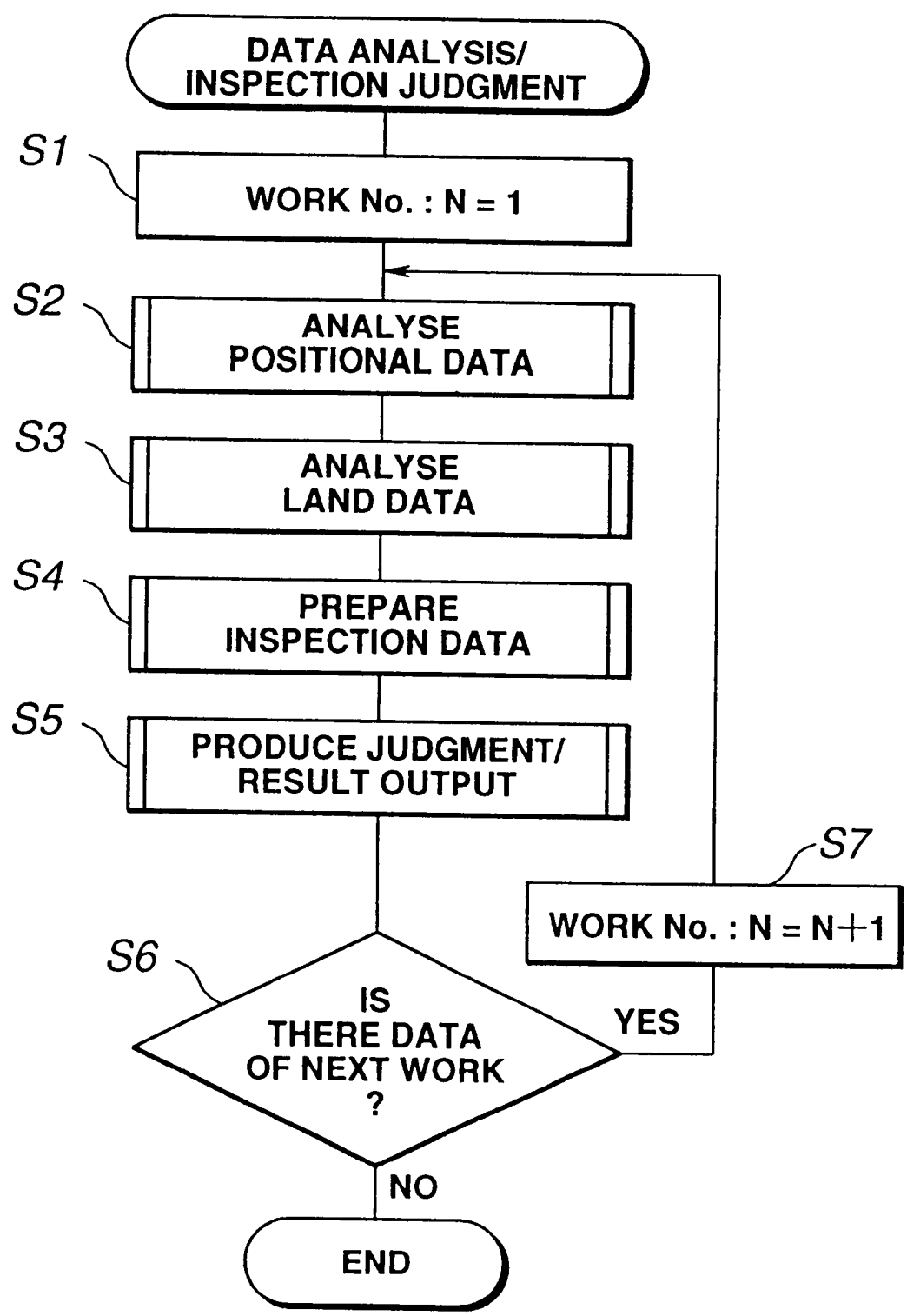
FIG. 24 is a flowchart of a data analysis/judgment process.
Figure 25:
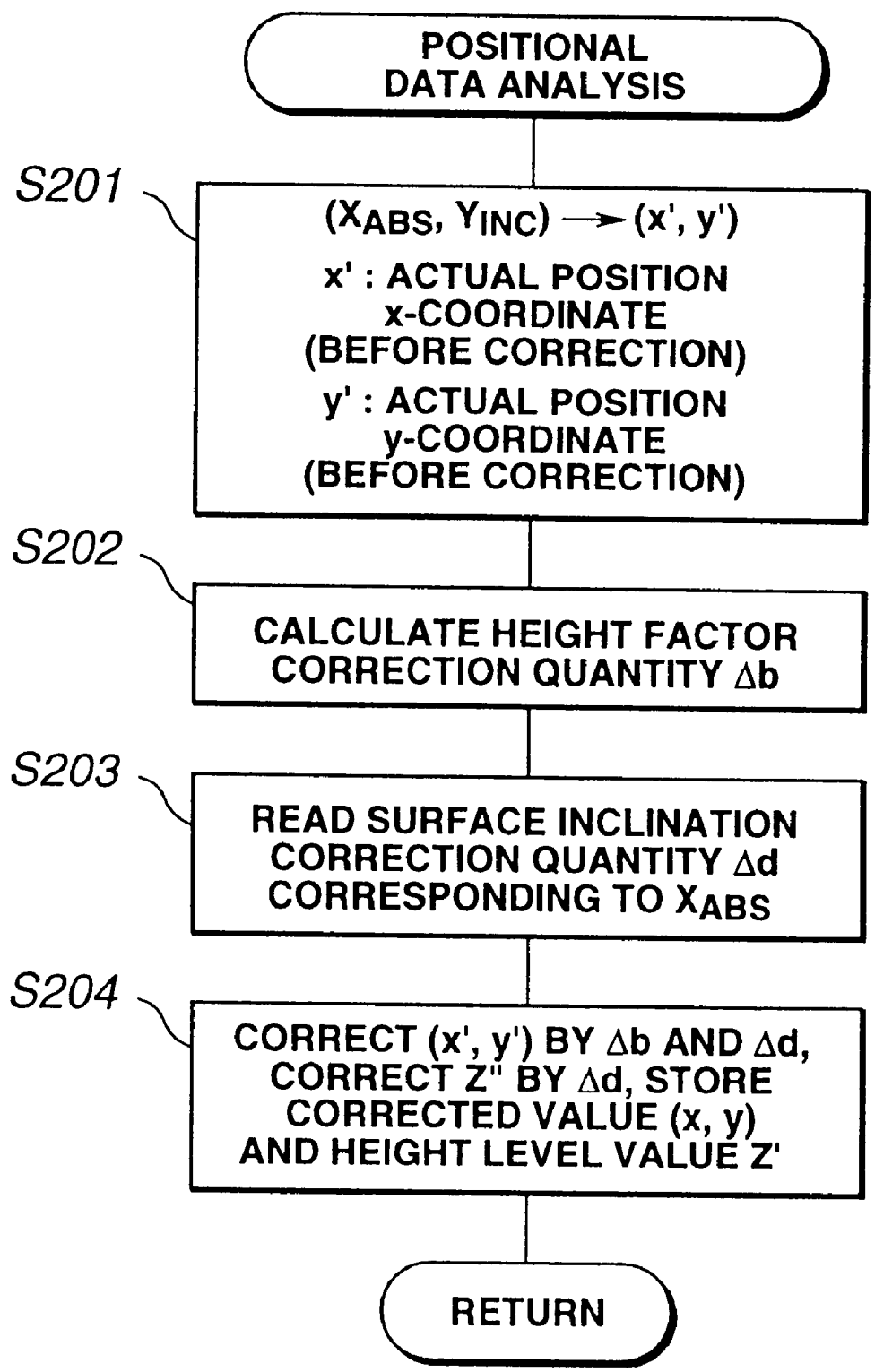
FIG. 25 is a flowchart of details of the positional data analysis process of FIG. 24.

Firstly, at S1 in FIG. 24, the data set OD of the first work is read and the process proceeds to S2 to execute a positional data analyzing process. Its detail is shown in FIG. 25. Firstly, the data ($X_{ABS}$, $Y_{INC}$) is in the form of an output value or a pulse count value from an encoder and is thus converted to the coordinate values (x', y') on the position coordinate (hereinafter referred to as inspection surface coordinates) which is set every inspection surface CP of each work (in the meantime, such conversion may previously be made on the measurement system control section 51 side and be transmitted in the form of data of (x', y') to the data analyzing section 81).

Then, as shown in FIG. 6, the laser beam LB is incident obliquely on the inspection surface at an incident angle θ, so the reflection positions of the same incident beam on the height reference surface SLP and the surface apart therefrom by Z' differ by the amount of Δb. In this connection, as will be apparent from FIG. 6, the following equations will be obtained.

$$\Delta b = L \cdot \cos\theta / \sin\phi \quad (1)$$

$$\phi = 180° - 2\theta \quad (2)$$

Figure 7:
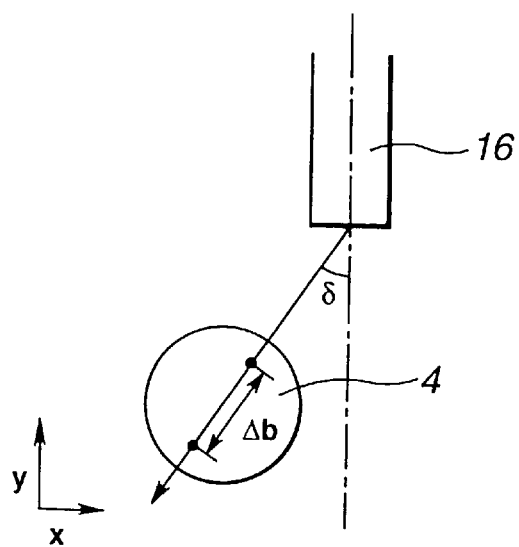
FIG. 7 is an illustration of an amount of correction of a detected height.

Thus, Δb will be obtained from θ0 and L. By Δb, the coordinate values (x', y') are corrected to such coordinate values that are based on the condition where incidence takes place against, for example, the height reference surface SLP. In this connection, as shown in FIG. 7, the beam from the laser beam source 12 is caused to scan in the x-direction while being changed in the angle δ with respect to the y-direction by means of the polygon mirror 16, but it makes a right angle with the inspection surface CP by the effect of the f·θ lens so correction on consideration of the angle δ is not necessitated. In the meantime, for the value of the incident angle θ, one of those stored in the correction data group memory section 94c is selectively read and used.

On the other hand, as shown in FIG. 11, if there is an error Δλ in the surface inclination angle of the polygon mirror 16, the position where the laser beam LB is cast or cast onto the inspection surface CP is caused to deviate by the amount Δd. Assuming that the focal length of the f·θ lens used is f, the deviation amount Δd can be calculated from f·2Δλ. On the other hand, by such deviation of the irradiation position is caused an error Δh in measurement of height.

Figure 12B:
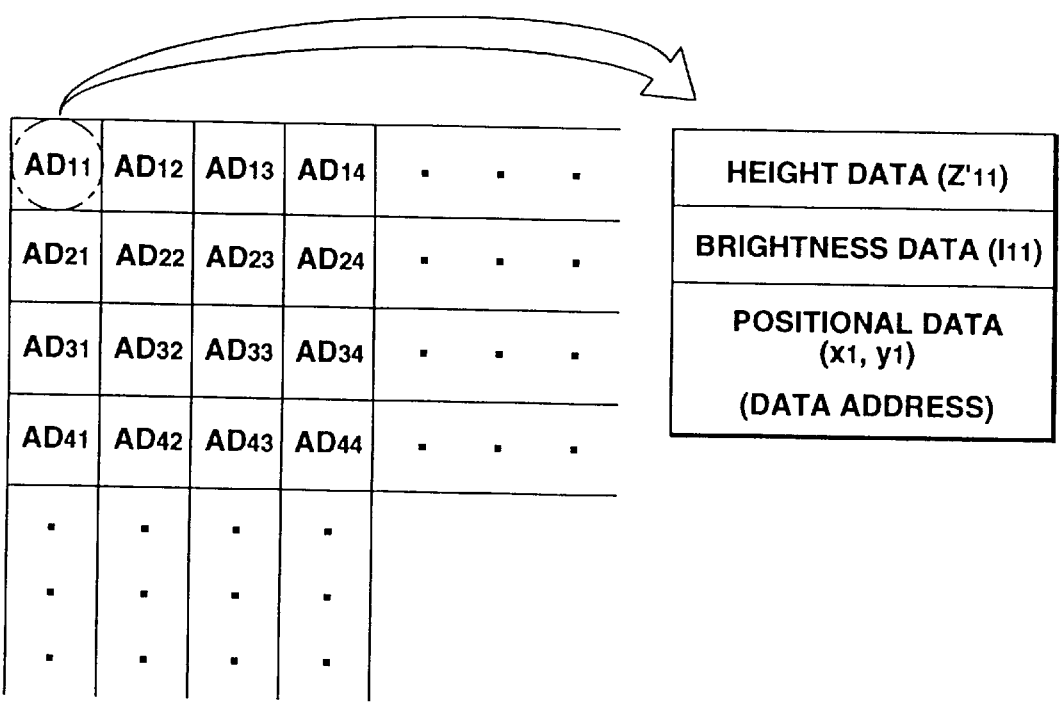

Then, as shown in FIG. 10, by storing in the correction data group storing section 94c a deviated amount Δd on the basis of an inclination angle of each surface of the polygon mirror 16 and fixing from the above described value of $X_{ABS}$ the surface of the polygon mirror 16 which is in use, a deviation amount Δd corresponding to the mirror surface in use is read (S203 in FIG. 25). At step S204 in FIG. 25, from the deviation amount Δd are obtained the correction value in the y-direction and the correction amount of the height level Z". The thus corrected coordinate values and height level are formed into a group AD of corrected coordinate values (x', y') and height level Z' in the inspection surface coordinate system and stored in the form of being correspondent to each scanning point (its stored condition is shown in FIG. 12B), and the positional data analyzing process is completed. In the meantime, the corrected coordinate values (x, y) are associated with each picture element or pixel in a display screen of a monitor (display device) 98 which will be described later, so they can be substituted for a data address corresponding to each picture element in the corrected data memory section on the assumption that the picture elements are arranged at constant intervals.

Figure 26:
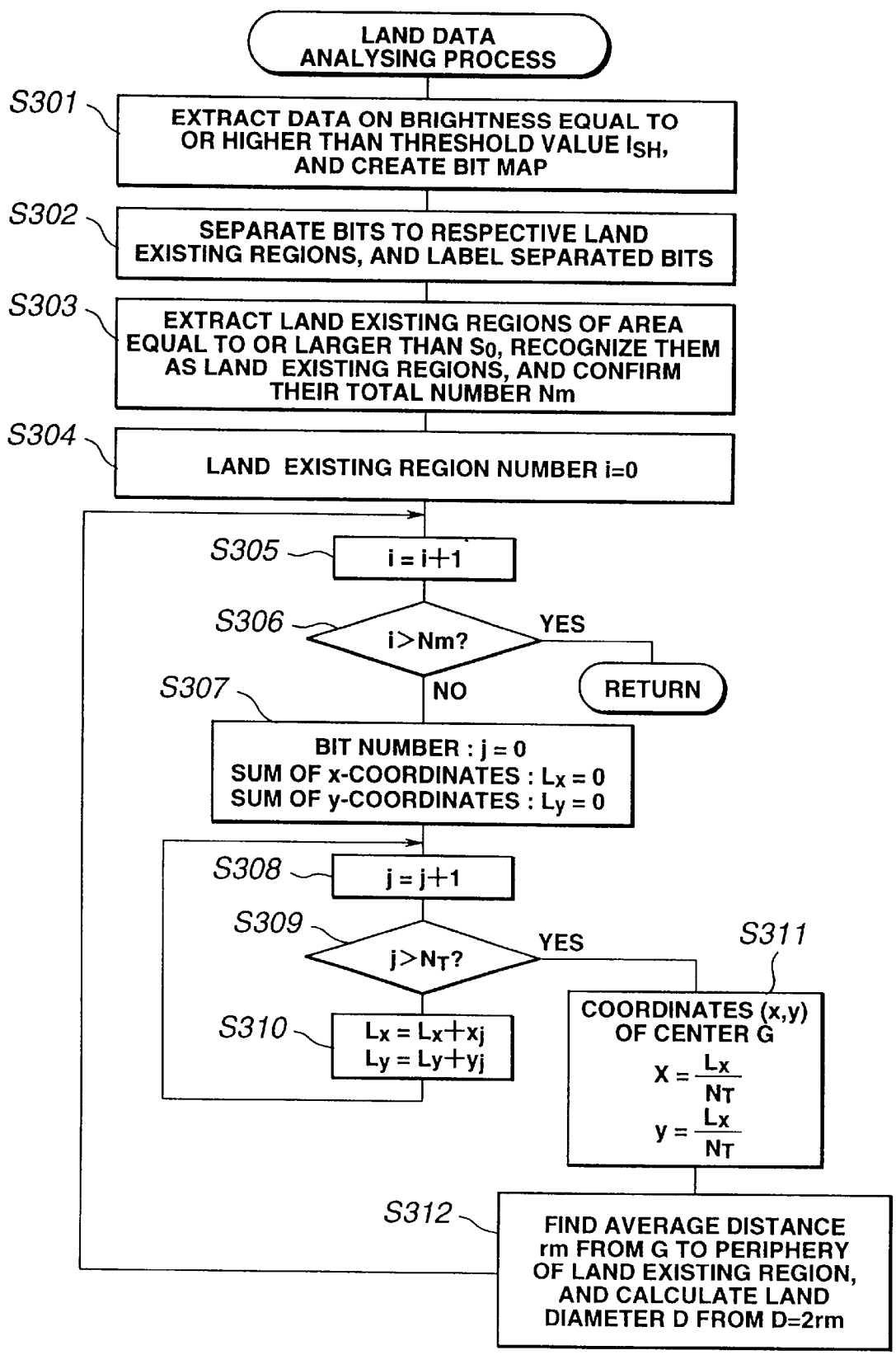
FIG. 26 is a flowchart of details of the land data analysis process of FIG. 24.

Returning back to FIG. 24, the process then proceeds to the land data analyzing process step at S3. FIG. 26 shows the detail of its flow. Firstly, at S301, the position coordinate (x, y) of each data group is associated one by one with each bit of a data bit plane set within, for example, an address space of the RAM 88 (refer to FIG. 5), and a bit map data is prepared on the basis of whether the brightness I is equal to or higher than a threshold value $I_{SH}$.

Figure 8:
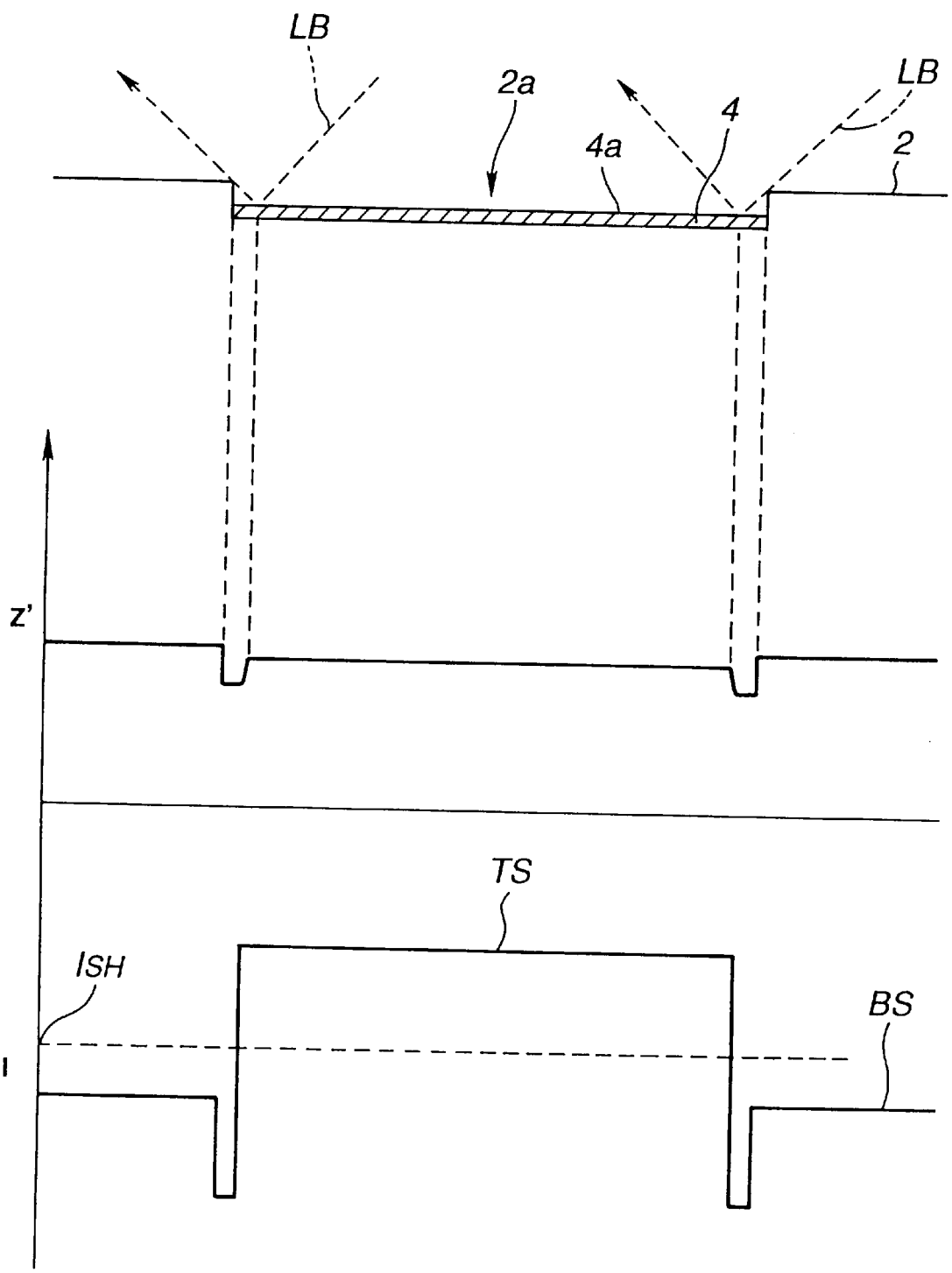
FIG. 8 is an illustration of a height level and a profile of brightness obtained by scanning a land crosswise with a laser beam.
Figure 9:
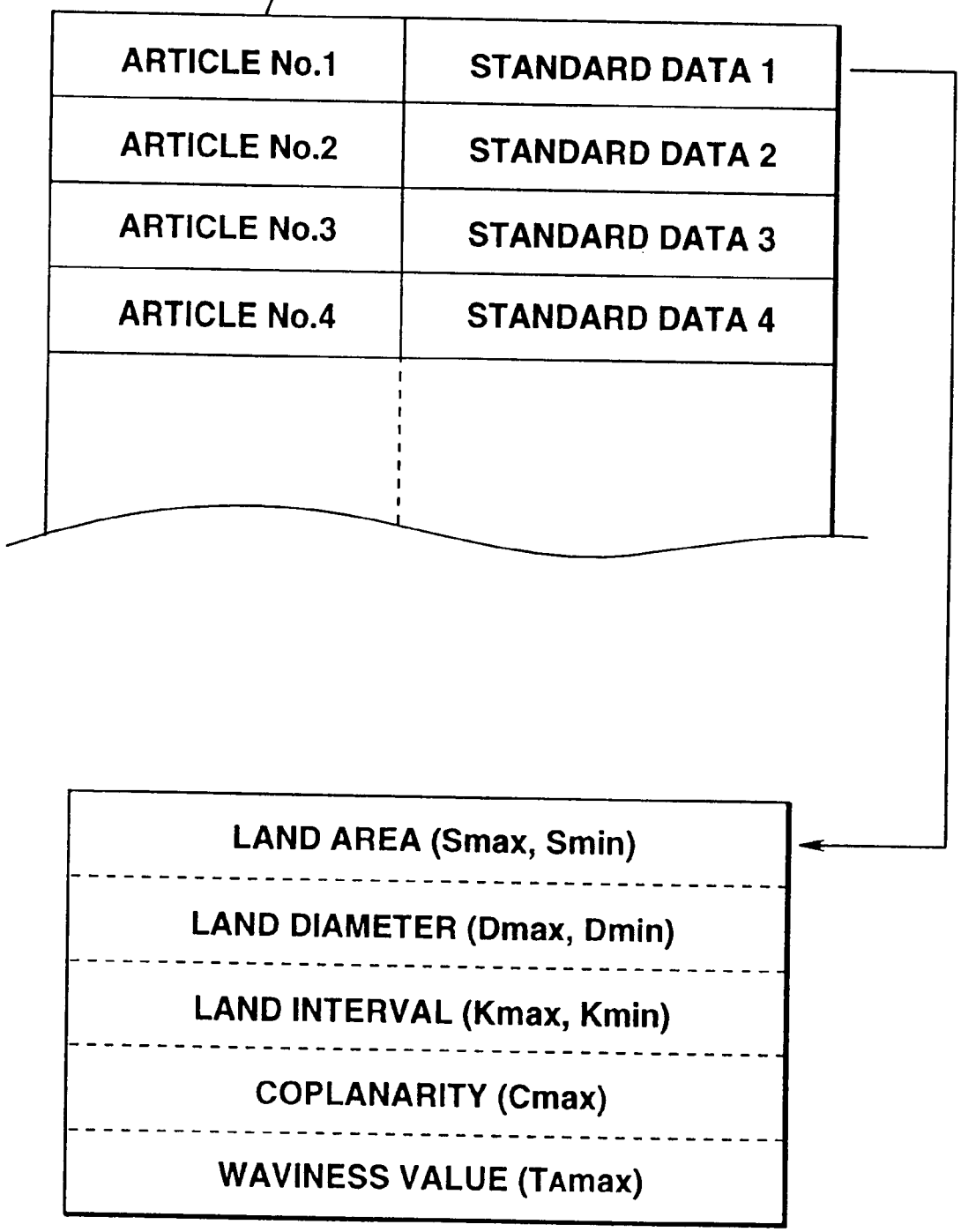
FIG. 9 is an illustration of a data stored in an inspection standard data memory section of the control system of FIG. 5.

FIG. 8 shows an example of profile of a height level Z' and of a brightness I, which is obtained by scanning the laser beam LB across the land 4. That is, the substrate 2 made of a resinous material is lower in the reflectance than the metallic land 4, so that the brightness I is higher at a region TS corresponding to the surface of the land 4 and lower in a region where the circuit board substrate 2 is exposed, i.e., at a background region BS around each land. The above described threshold value $I_{SH}$ is set so as to be higher than an average brightness level of beam reflected from the surface of the circuit board substrate 2 when a laser beam of a predetermined intensity is incident onto the surface of the circuit board substrate 2. In the meantime, if the surface condition of the land 4 is the same, the same level of brightness I results even when the land height level Z' becomes lower.

Figure 14:
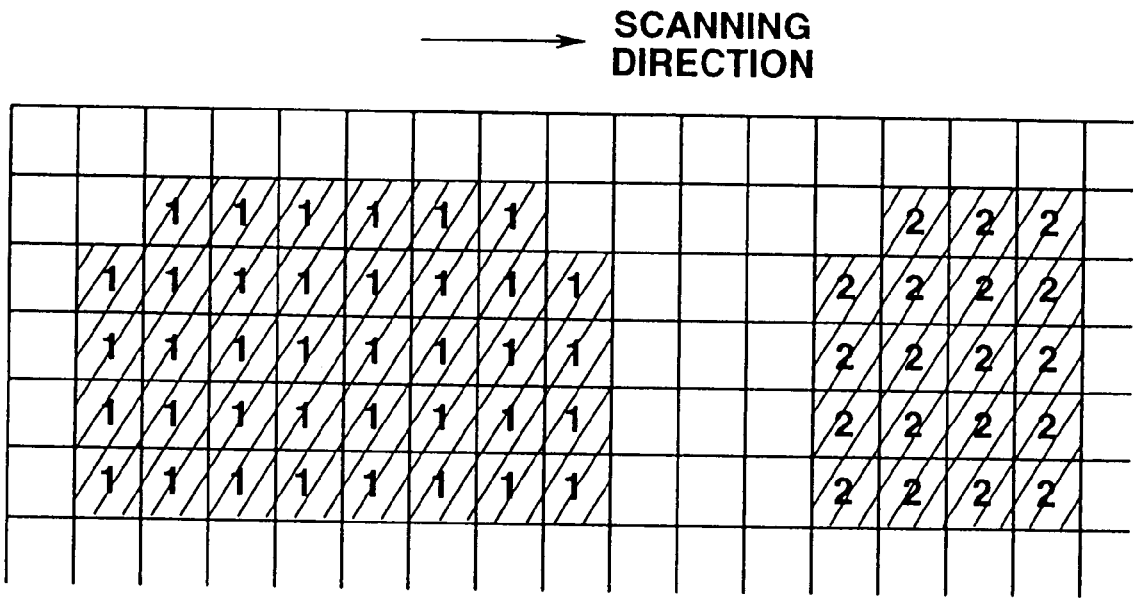
FIG. 14 is an illustration of a method of determining land existing regions by the use of bit map data.

Thus, by setting the threshold value $I_{SH}$ for the brightness of the reflected beam, a land 4 existing region on the inspection surface can be fixed on the basis of the above described bit map data. For example, as shown in FIG. 14, assuming that a bit that is higher than the threshold value $I_{SH}$ is represented by "1" (bit that is hatched) and a bit that is not is represented by "0" (bit that is not hatched), an region where the bits "1" appear collectively represents the land existing region. Hereinlater, in this embodiment, a bit for a land existing region is represented by "1" and an region other than the land existing region is represented by "0".

As shown in FIG. 8, in this embodiment, each land 4 is formed within the shallow depression 2a so its surface 4a is set back from the outer opening end of the depression 2a. Accordingly, by the outer peripheral portion of the surface 4a of the land 4 is caused little a reflected beam since the laser beam LB incident obliquely onto the outer peripheral portion of the surface 4a is blocked or interrupted by the inner circumferential surface of the depression 2a, etc., thus causing a silhouette region SA whose brightness I is very small. This region SA causes little a reflected beam, so the data on the height level is in the form of being lost or missing (in actual processing, they can be considered as being a value approximating to zero). However, in this embodiment, the depth by which the surface 4a of the land 4 is set back from the outer surface of the substrate 2 is fairly smaller than the diameter of the land 4 (e.g., the depth is 15 μm for the diameter of the land is 600 μm), so the silhouette region SA is judged as being negligible in, for example, calculation of the size or area of the land which will be described hereinlater.

Then, the process proceeds to S302 in FIG. 26 to perform a process for separating the bits to the respective land existing regions on the basis of the bit map data. That is, as shown in FIG. 14, the bit map data is scanned in a predetermined direction, e.g., in the x-direction, and a label mark (in this embodiment, a numeral such as 1, 2, . . . , and so on) is put to each bit, while making a distinction between the bit that constitutes the same land existing region and the bit that constitutes another land existing region on the basis of whether a break in the continuation of bits "1" that is so large as to correspond to a predetermined number of bits "1" (e.g., 3 bits) or more occurs or not. In the meantime, when, in scanning along the second scanning line or row and onward, a bit detecting condition is changed from that detecting a bit "0" to that detecting a bit "1", the labeling condition of, for example, eight bits surrounding that bit "1" at that moment is detected so that the same label mark is put to that bit when a label mark of a bit having already been recognized is detected and a new label mark is put to that bit when nothing is detected. The aggregate sets of bits which are different in the label mark are recognized as different land existing regions.

For example, in the case of the data set in which the height level data Z' is distributed as shown in FIG. 13A and the brightness data I is distributed as shown in FIG. 13B, the land existing region appears on the bit map data as shown in FIG. 13C by setting the brightness threshold value $I_{SH}$ to 7 (however, it is represented in FIG. 13C by writing the values Z' at the respective positions in the corresponding bits). In the meantime, for use as the brightness threshold value $I_{SH}$, suitable one of those stored in, for example, the correction data group memory section 94c is read and used.

Figure 16A:
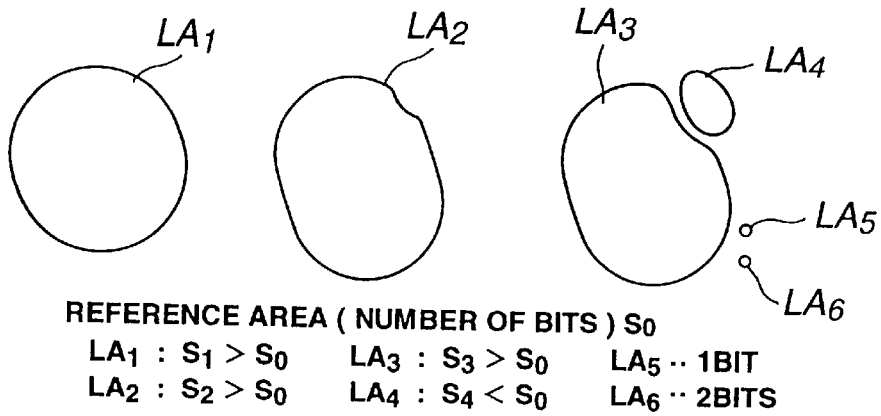
FIGS. 16A to 16D are illustrations of a way of determining a land existing region.

Returning to FIG. 26, at S303, the land existing regions of the area equal to or larger than a suitably set reference area $S_0$ are extracted from those which are separated from each other, as shown in FIG. 16A, and recognized as a land existing region which is an object to be inspected (LA1–LA3 in FIG. 16A). The area of each region can be found by the number of bits belonging to that region. In the meantime, the region the number of bits of which is smaller than a certain threshold value (e.g., 3 bits) which is smaller than the number of bits corresponding to the reference area S0, is excluded as noise (for example, LA5, LA6 in FIG. 16A).

Figure 15:
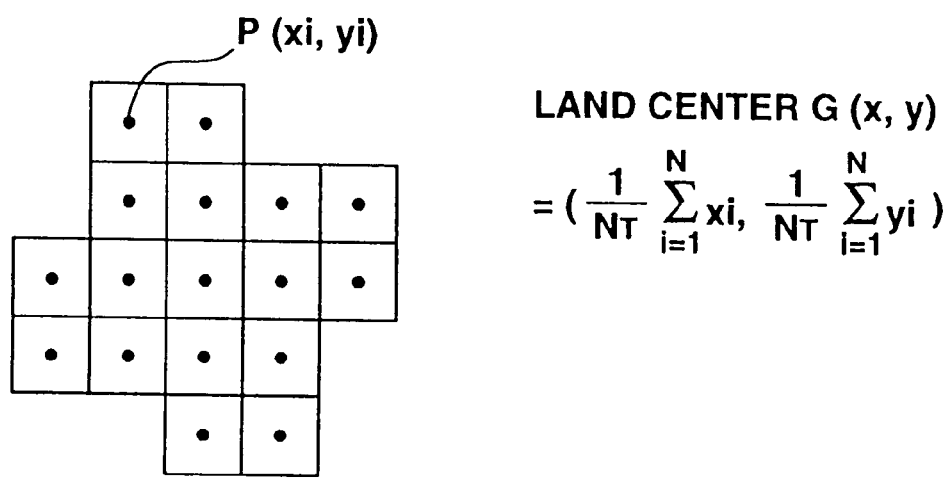
FIG. 15 is an illustration of a method of obtaining coordinates of a center of each land.

Then, at S307 to S311 in FIG. 26, the coordinates of the geometric center of gravity of each extracted land existing region are calculated, and a process for determining the calculated coordinates as the coordinates of the center G of each land. More specifically, as shown in FIG. 15, the coordinates of the center G can be obtained by calculating the sum of the x-coordinate values and y-coordinate values of the points P on the inspection surface, each point P corresponding to each bit, i.e., calculating the sum of the coordinate values for all the bits within the region, and dividing the sum (Lx) of the x-coordinates and the sum (Ly) of the y-coordinates by the total number $N_T$ of bits.

Figure 50:
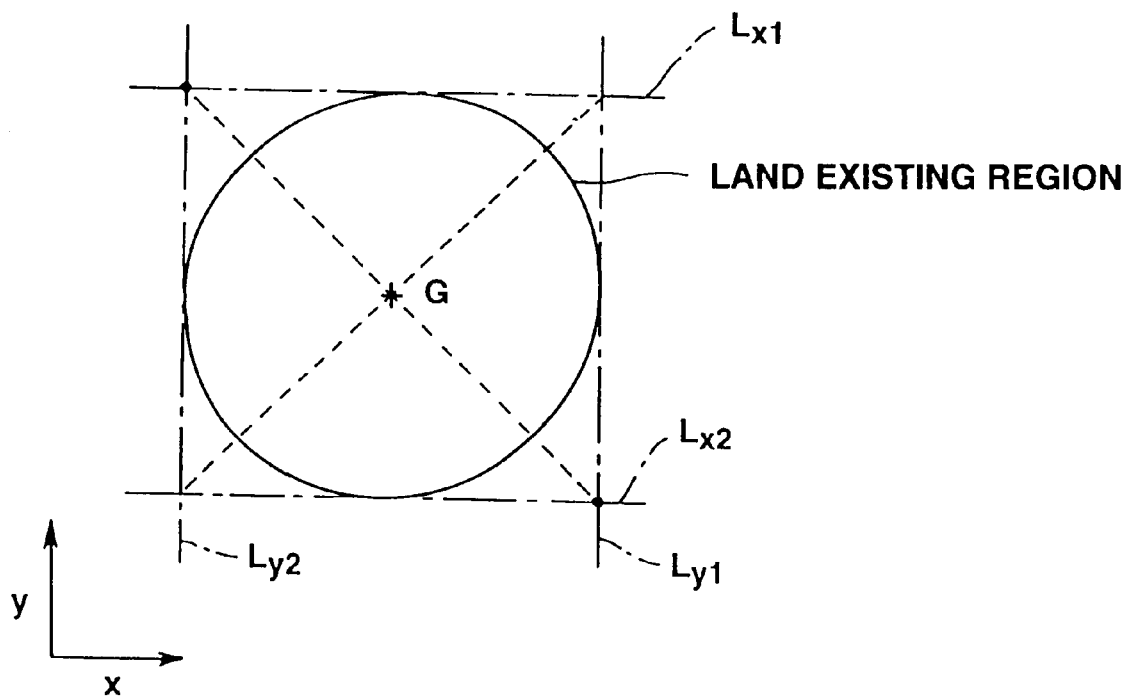
FIG. 50 is an illustration of a variant of a method of calculating coordinates of a center of a land.

In the meantime, as shown in FIG. 50, the coordinates of the center G of the land can be calculated by first obtaining a quadrilateral region circumscribed about the land existing region and then obtaining an intersecting point of diagonal lines of the quadrilateral region. In this instance, for example, a line elongated in the x-direction is moved in parallel with the y-axis, whereby to determine two straight lines Lx1 and Lx2 that touches the land existing region at points. Then, a line elongated in the y-direction is moved in parallel with the x-axis, whereby to determine two lines Ly1 and Ly2 that touches the land existing region at points. By this, the above described quadrilateral is set as a rectangular region, and the coordinates of the point of intersection of its diagonal lines can be obtained by calculation of the coordinates of the middle point of one of the diagonal lines. By doing so, calculation of the x-coordinate and y-coordinate of each bit can be dispensed with, thus making it possible to simplify the process of calculating the coordinates of the center of the land.

Figure 52:
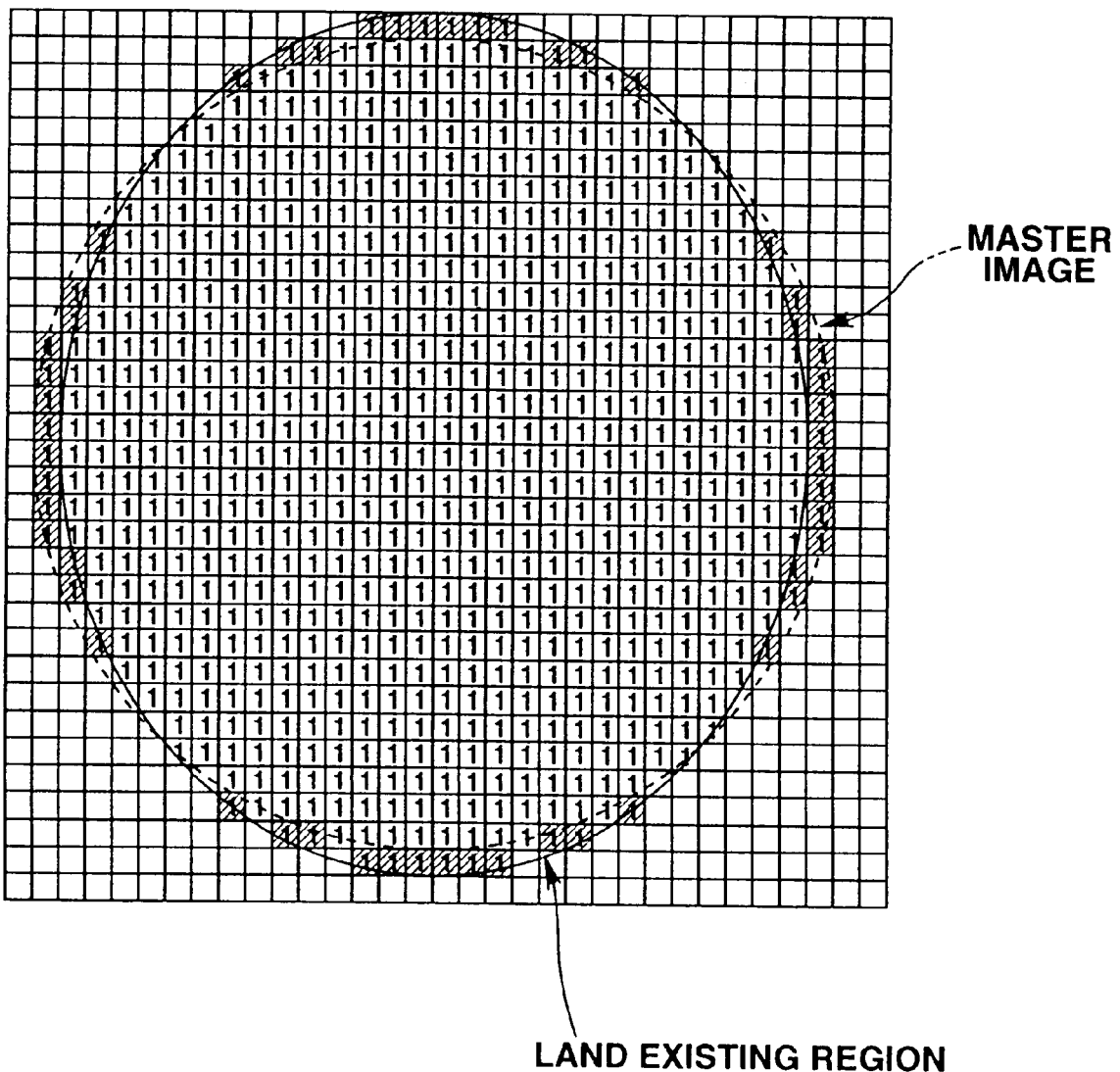
FIG. 52 is an illustration of another variant of a method of determining a center position of a land.

Further, as shown in FIG. 52, the coordinates of the center G of the land can be calculated by first moving a master image which is an imaginary circle prepared in advance, in the x-direction and y-direction to determine a position where the number of pixels which are not common to the master image (the external shape is represented by the dotted line) and the land existing region (the external shape is represented by the sold line) becomes minimum, and then calculating the coordinates of the geometric center of gravity of the master image at that position for use as the coordinates of the center G of the land (in FIG. 52, the image of the land existing region is a binary image wherein the output of the pixel located within the land existing region is "1" and the pixel outside the land existing region is "0". In this instance, the master image can be determined as a circle with the same area as the land existing region LA or a circle which is obtained from any three points on a boundary between the land existing region LA and a background surface. In case the circle obtained from any three points on that boundary is used as the master image, the calculation process is relatively easy so improvement in the process speed can be attained.

Figures 53A, 53B:
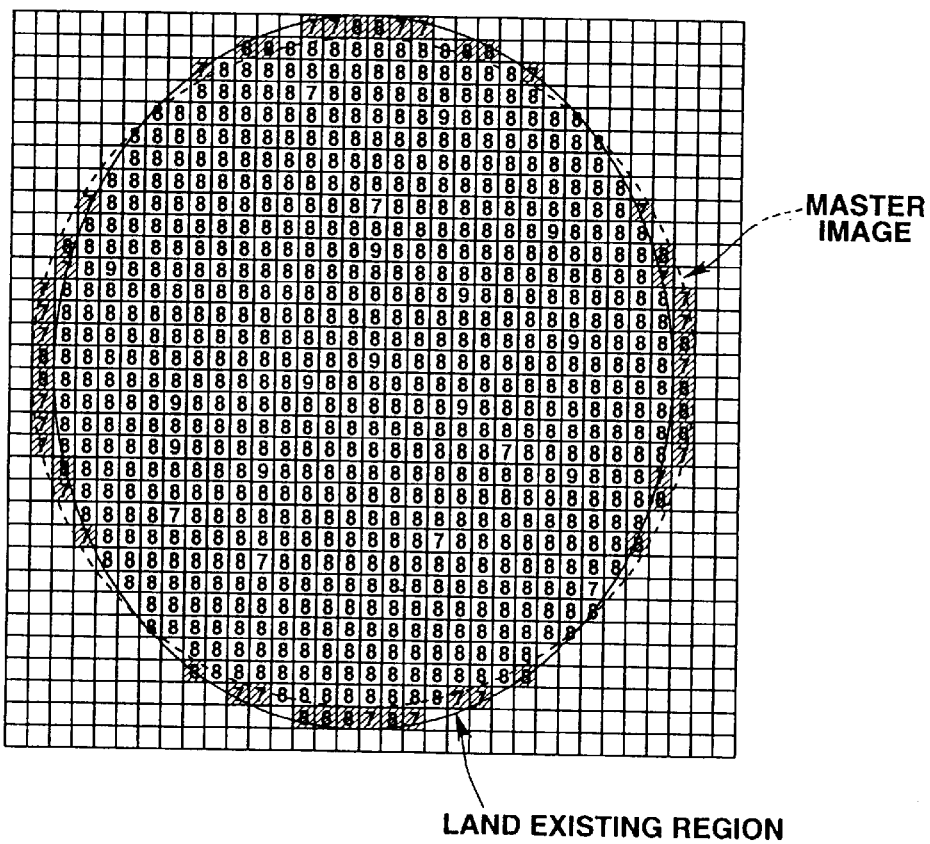
FIGS. 53A and 53B are illustrations of a further variant of a method of determining a center position of a land.

On the other hand, as shown in FIG. 53A, an image resulting from a combination of a plurality of pixels which can be set to produce an intermediate output (e.g., a gray scale image or color image) can be used as an image indicating a land existing region and a master image (in the figure, within the cell of each pixel is described in figures a set output value). In this instance, a standard picked-up image of a land can be prepared in advance for use as the master image. As shown in FIG. 53B, an absolute value of a difference in the set output value between the corresponding pixels of the master image placed in a predetermined position through movement in the x-direction and y-direction and the image indicating the land existing region and placed upon the master image (assuming that the set output value of each pixel indicating the master image is m and the set output value of each pixel indicating the land existing region is w, |mij−wij|) is calculated and then the sum (or the average) of the absolute values is calculated. Then, the position of the master image where the above described calculated total of the absolute values becomes minimum is found, and by determining the geometric center of gravity of the master image at that position as the center of the land, the coordinates of the center G of the land are calculated.

Figure 17:
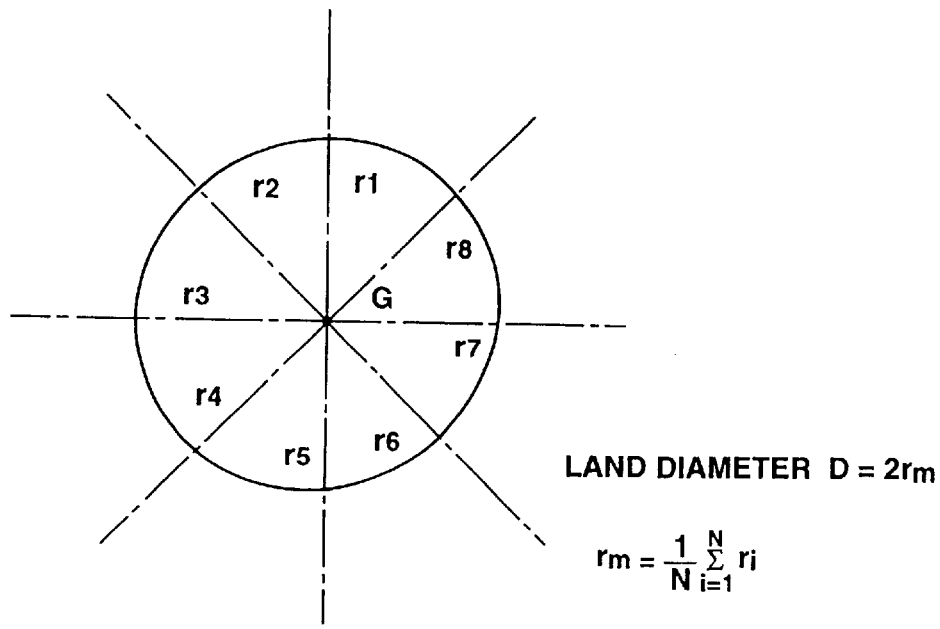
FIG. 17 is an illustration of a method of obtaining a distance from a center to a peripheral boundary of a land existing region.
Figure 19:
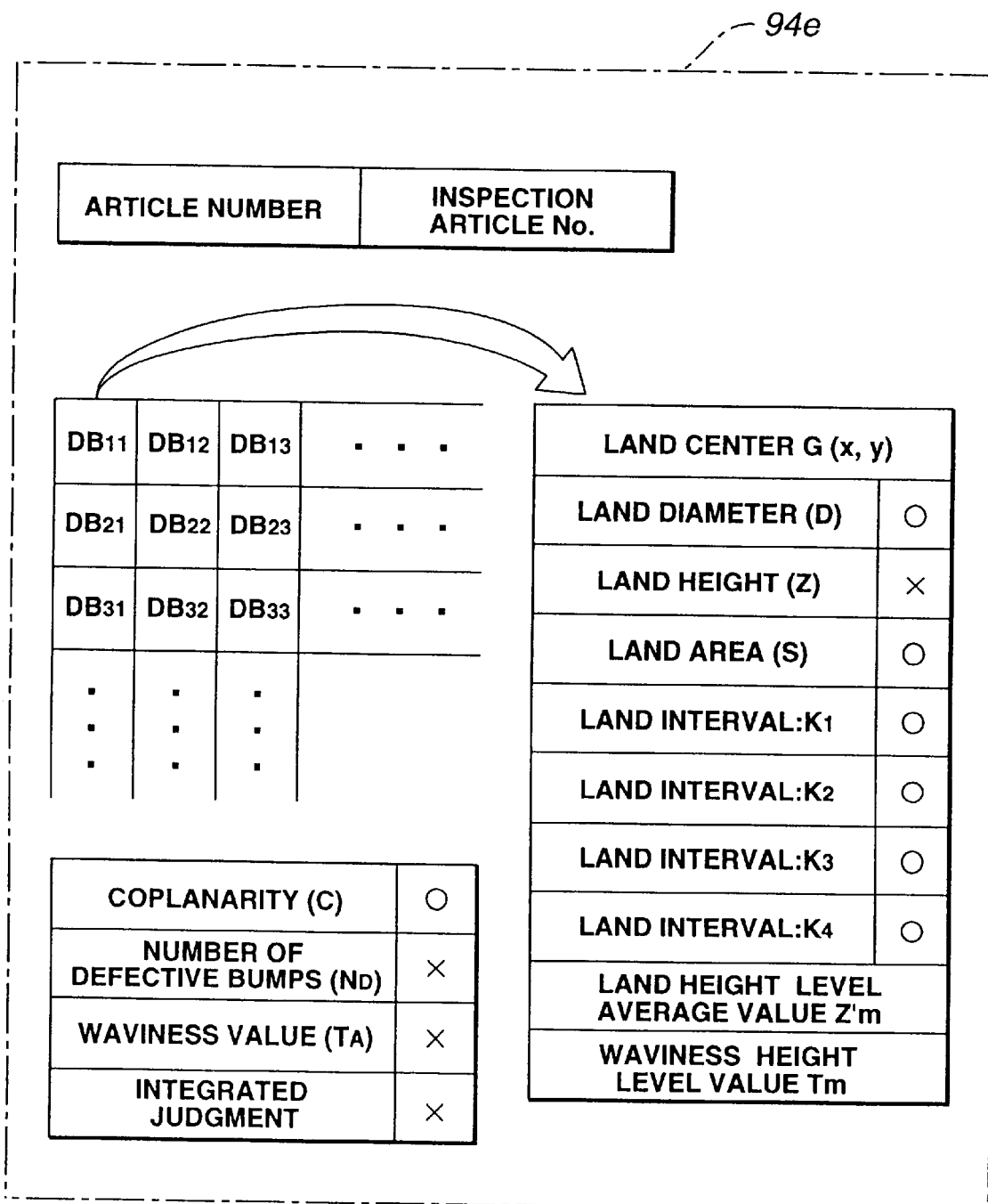
FIG. 19 is an illustration of a content of an inspection result data memory section of the control system of FIG. 5.

Returning to FIG. 26, after calculation of the coordinates of the center G of each land, the process proceeds to S312 to perform a process step of calculating the diameter D of the land. That is, as shown in FIG. 17, an average distance rm from the center G of the land existing region to its periphery (in this embodiment, an average of the distances in the eight directions arranged at regular intervals) is found, and then the land diameter D is calculated from 2 rm. This step is repeated for the land existing regions (S304 to S306 in FIG. 26). In the meantime, the determined coordinates of the center G and land diameter D are stored in the inspection result data memory section 94e (its detail is shown in FIG. 19). In the meantime, the land diameter D can be calculated by finding the area of the land existing region from the number of bits within the land existing region and determining the diameter of a circle of the same area as the land existing region as the land diameter D.

Figure 16B:
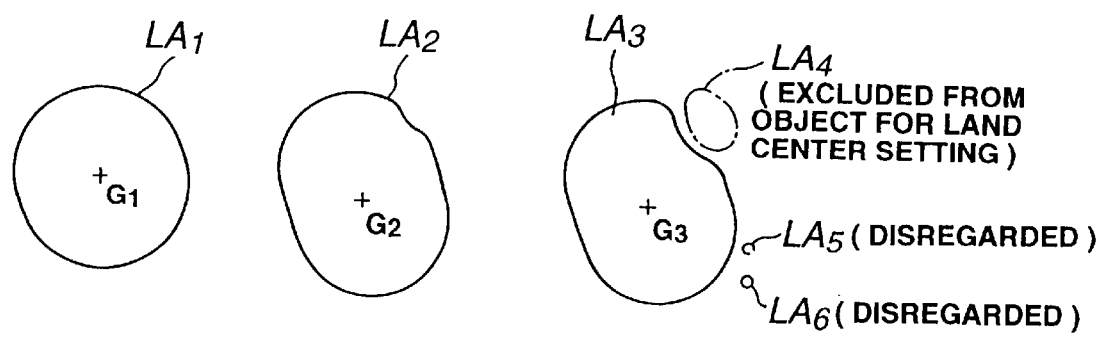

In this instance, in the event that the land is nearly normal as shown in FIG. 16A, the land existing region nearly reflects the shape of the land. On the other hand, in case the surface of the land is rough or the land is partially chipped, there can possibly occur such a case in which two or more land existing regions resulting from the same land are present as indicated by LA3 and LA4. In this instance, only the Land LA3 whose area is equal to or larger than a reference area S0 is regarded as a land existing region as shown in FIG. 16B, and the chip LA4 whose area is smaller than the reference area S0 is excluded from the object about which the process of determining the center of the land is to be carried out. By this, there can be avoided such a trouble that the chip LA4 is erroneously regarded as another land. On the other hand, in case the land existing regions resulting from the same land are all smaller than the reference area S0, no land existing region is recognized with respect to that land. However, such a result is caused due to the fact that the surface condition or the like of the land is not good from the first, so by utilizing the result reversely it becomes possible to assume existence of a defective land.

In FIGS. 21A and 21B, an example of a method of carrying out such an assumption about existence of a defective land is shown. As shown in FIG. 21B, a group of position tolerance defining windows PW for defining the tolerance or permissible range of the position where each land is formed is set on the inspection surface CP of the land-attached circuit board 1. An area of a land existing region (high brightness region) LA located within each position tolerance defining window PW is calculated, whereby it becomes possible to judge, in case the ratio of the thus calculated area to the area of the window PW is equal to or smaller than a predetermined ratio, that a defective land exists within the window PW. In the meantime, the set position of the group of position tolerance defining windows PW on the inspection surface is the same so long as the land-attached circuit board 1 is of the same kind. Thus, as shown in FIG. 21A, a target mark for determining a positional relation between a window group PWG formed by a group of windows PW and the inspection surface CP is formed on the land-attached circuit board 1 previously, whereby at the time of inspection alignment or positioning of the window group PWG can be attained by the use of the target mark.

Figure 54:
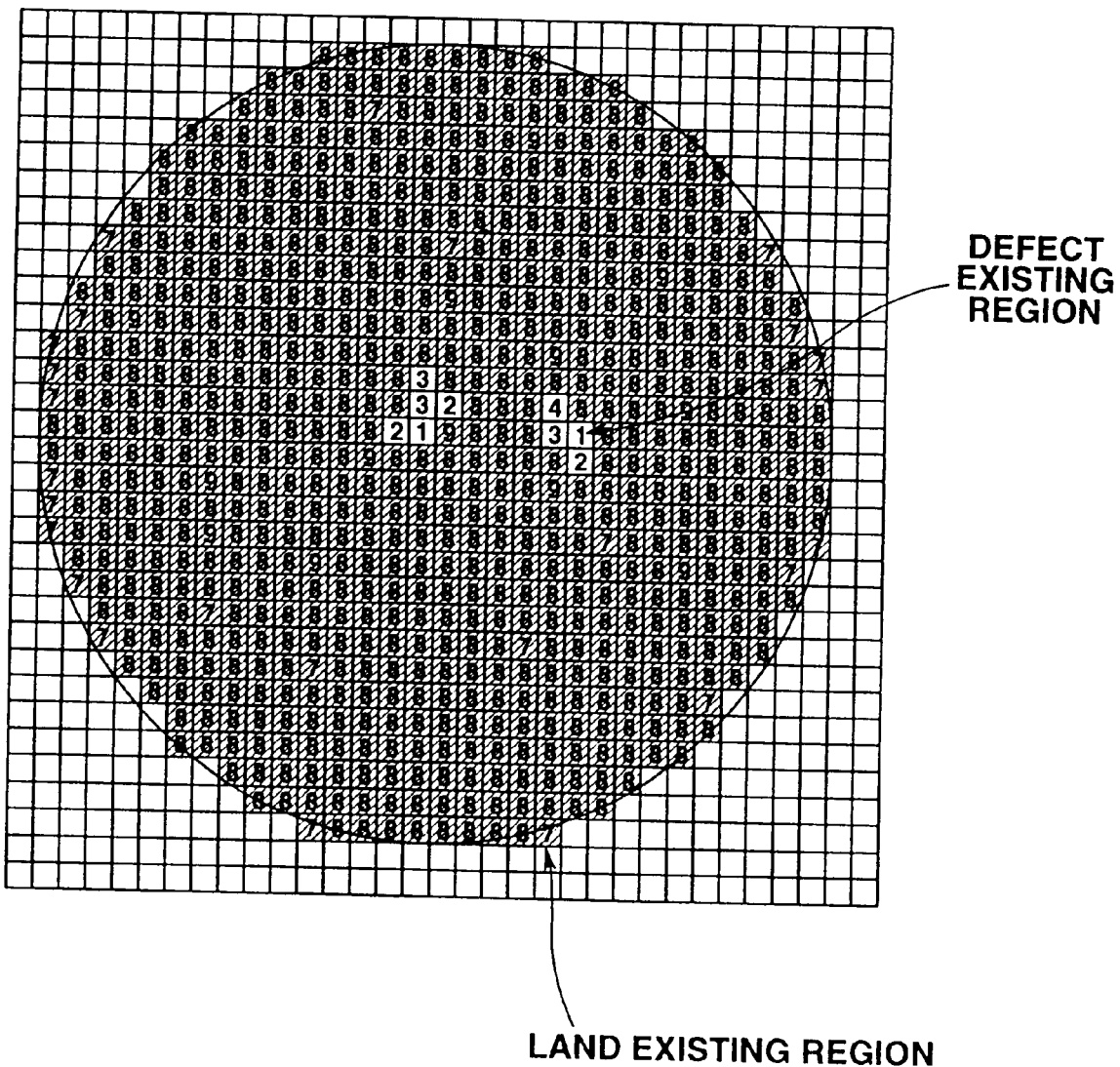
FIG. 54 is an illustration of a method of determining a defect existing region.

FIG. 54 shows an example of a method of estimating existence of a defective land in case the surface of the land has a flaw or the like defect. That is, on the basis of reflected beam brightness data I, a threshold value with respect to the inspection surface CP of the land-attached circuit board 1 is set, and then the land existing region LA is determined in the above described manner. If there is any flow or the like defect within the land existing region LA, the portion having such a defect is low in the value concerning the reflected beam brightness date I, thus causing a missing of data at the time of determination of the land existing region LA. Accordingly, in case a missing of some bits within the land existing region LA is recognized, it can be judged that a defect is present within the land existing region LA.

In the meantime, in place of the target mark, the window group PWG may be positioned in place by utilizing the centers of particular lands on the land-attached circuit board 1 (for example, the centers of four lands at the four corners of the land-attached circuit board 1).

Figure 27:
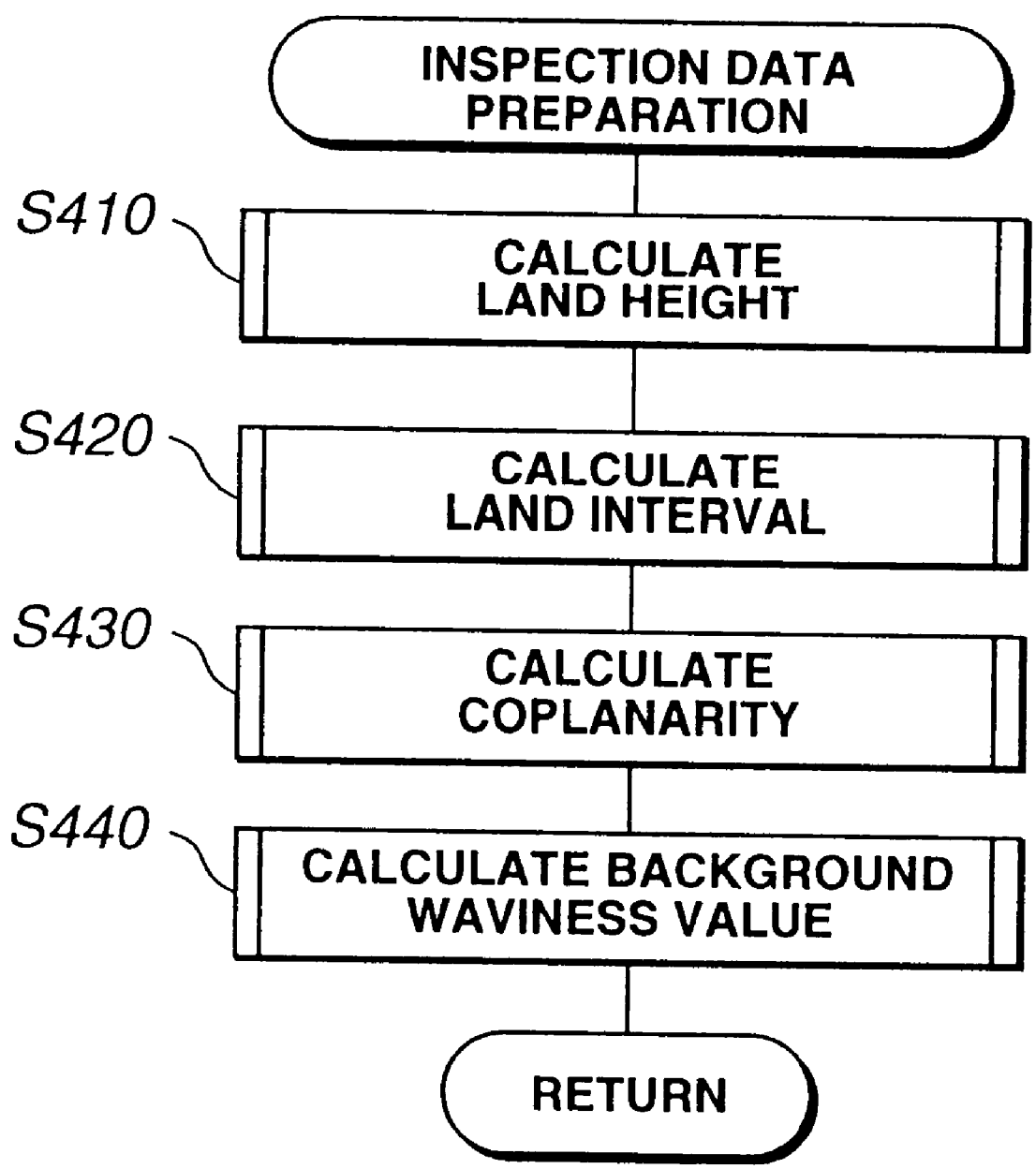
FIG. 27 is a flowchart of details of the inspection data preparing process of FIG. 24.

By the forgoing steps, the land data analyzing process is completed and the process proceeds to S4 shown in FIG. 24 for carrying out a process for inspection data preparation. As shown in FIG. 27, the inspection data preparing process in this embodiment consists of four steps, i.e., a land height calculating step (S410), a land interval calculating step (S420), a coplanarity calculating step (S430), and a background waviness value calculating step (S440).

Figure 16C:
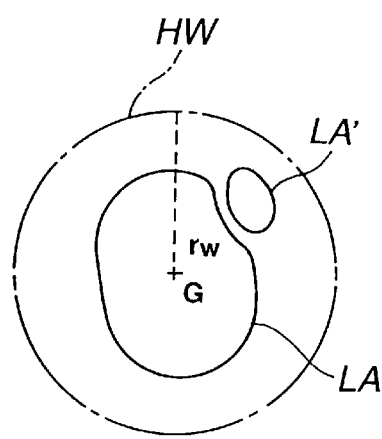
Figure 16D:
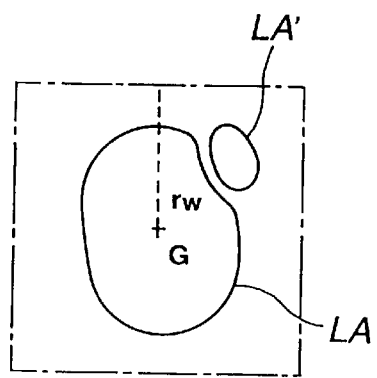
Figure 28:
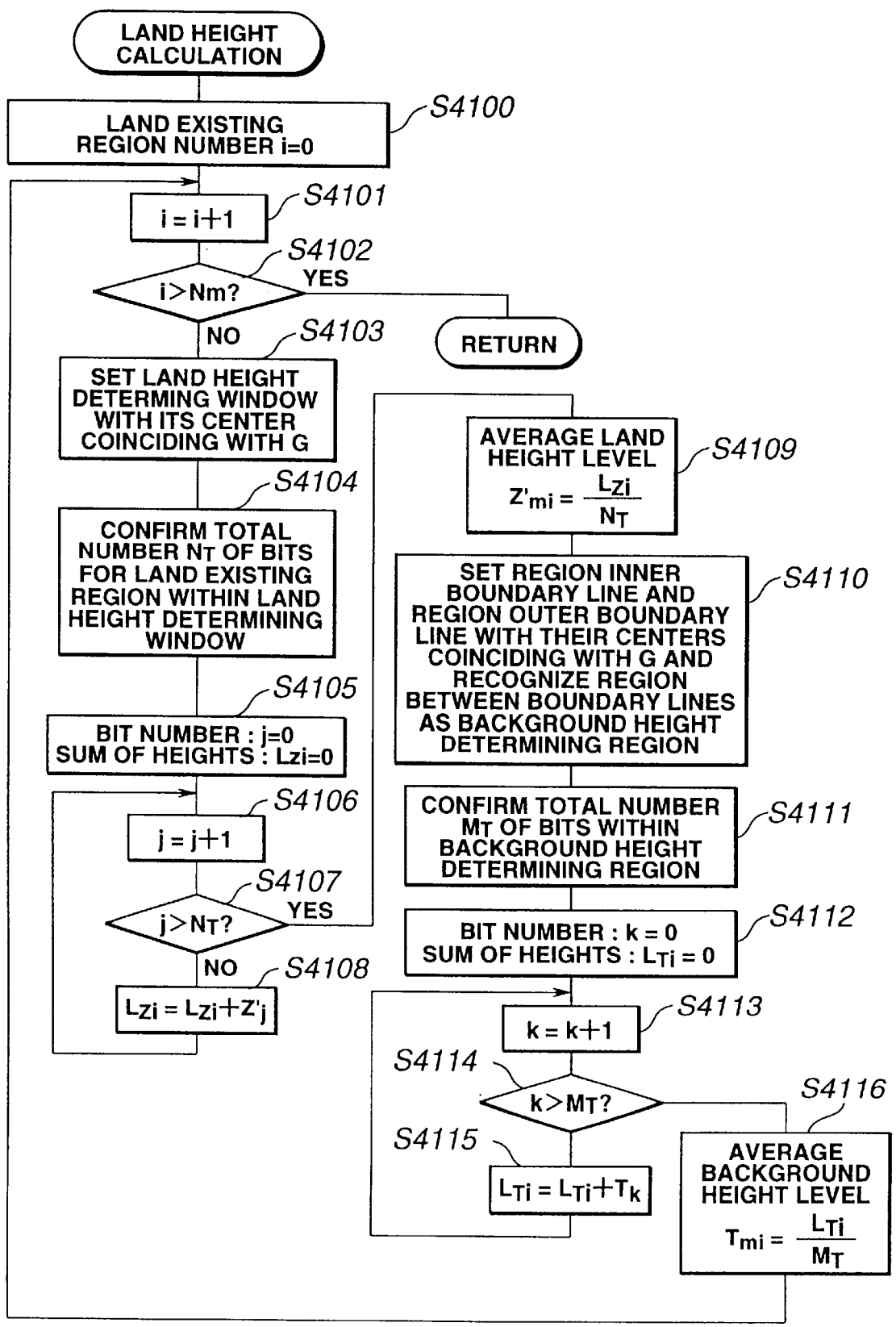
FIG. 28 is a flowchart of details of the land height level calculating process of FIG. 27.

FIG. 28 shows a control flow of the land height calculating process. A principal portion of the process resides in the steps S4103–S4116. At S4103, for the determined land existing region described above, a land height determining window (land height level determining region) with its center coinciding with G is set to be of such a size as to include therewithin the land existing region. For example, in the example shown in FIG. 16C, the land height level determining window HW is set to be of such a circle of a predetermined radius rw that is larger in size than the land existing region. Further, as shown in FIG. 16D, the land height level determining region can be formed into a quadrilateral or square. In the following steps S4102–S4109, by performing, for all of the land existing regions located within the above described land height level determining window HW (LA and LA' in FIG. 16C), addition of the height levels Z' each corresponding to each bit and by dividing the thus added-up value Lz by the total number of bits $N_T$, an average height level $Z'm=L_z/N_T$ of the surface of each land is found.

In this instance, the surface of the circuit board substrate 2 is not always perfectly flat but a variation of the height level of the land surface or the background surface may possibly occur. Particularly, in case the circuit board substrate is made of a resinous material, warping or the like surface defect is liable to be caused, as shown in FIG. 33, due to the difference in the coefficient of thermal expansion between the high polymer material constituting the substrate 2 and a metal constituting a metallic wiring disposed inside the substrate 2 when the substrate 2 is subjected to heating during the manufacturing process.

Figure 18:
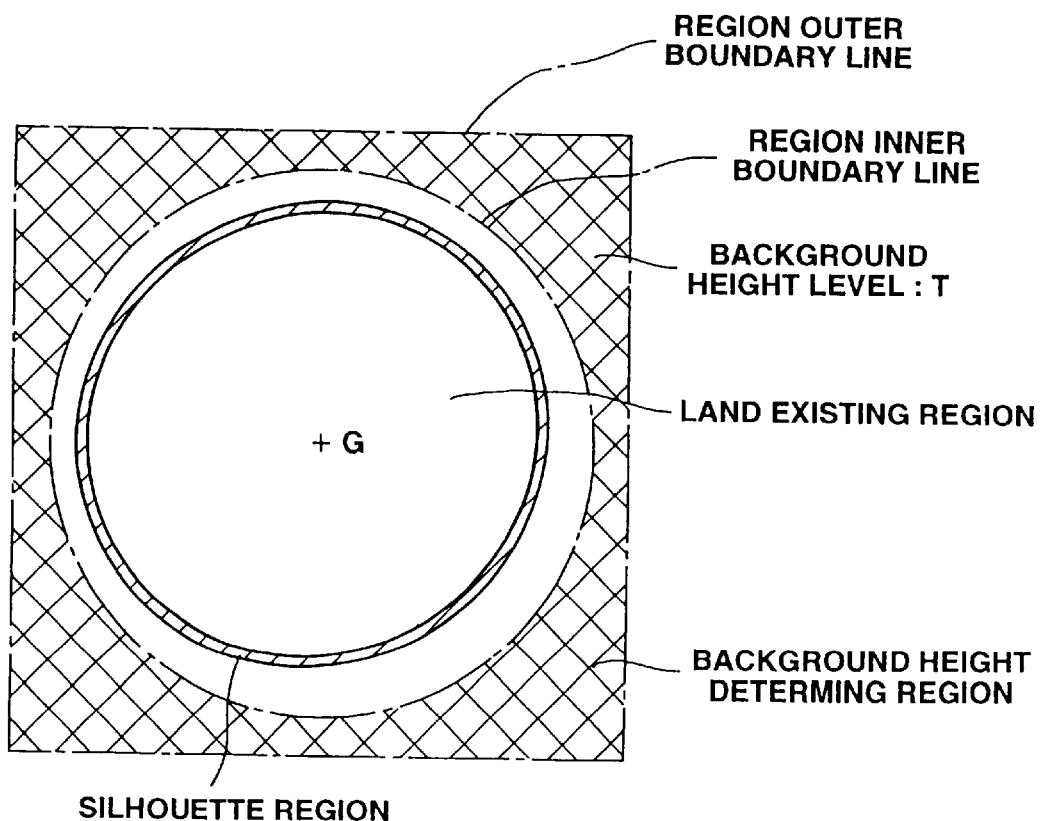
FIG. 18 is an illustration of a background height determining region.

Thus, in the flow of the process of FIG. 28, the average height level Tm (hereinafter will be referred to as "waviness height level") of the background surface around each land is calculated at steps S4110 to S4116 in the following manner. That is, as shown in FIG. 18, it is set an inner boundary line outside the land existing region (or a silhouette region) caused around the land existing region and in a manner as to surround these regions, and it is further set an outer boundary line which is located more outside than the inner boundary line. The region located between those boundary lines is set as a background height level determining region (S4110). In this embodiment, the inner boundary line is formed into a circle concentric with the center G of the land existing region, and the outer boundary line is formed into a square shape with an intersecting point of its diagonal lines being coincident with the center G (however, they are not limited to those shapes, for example, the outer boundary can be formed into a circle).

The height levels T corresponding to the respective bits within the background height determining region are added up to obtain $L_T$, and the waviness height level $T_m$ is obtained by dividing the calculated value $L_T$ by the total number MT of bits, i.e., can be calculated from the following expression (S4112–S4116).

$$Tm=LT/MT \quad (3)$$

In the meantime, the above described process is carried out repeatedly for the respective land existing regions (S4100–S4102). The average height level Z'm and waviness height level Tm of each land 4 obtained in the above described manner is stored in the inspection result data memory section 94e of FIG. 5 and FIG. 19.

Figure 20:
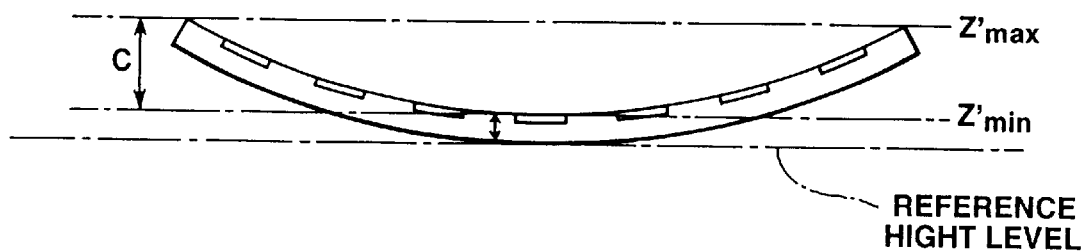
FIGS. 20A and 20B are illustrations of a coplanarity of a circuit board and a process for fixing a state of land array, respectively.
Figure 20B:
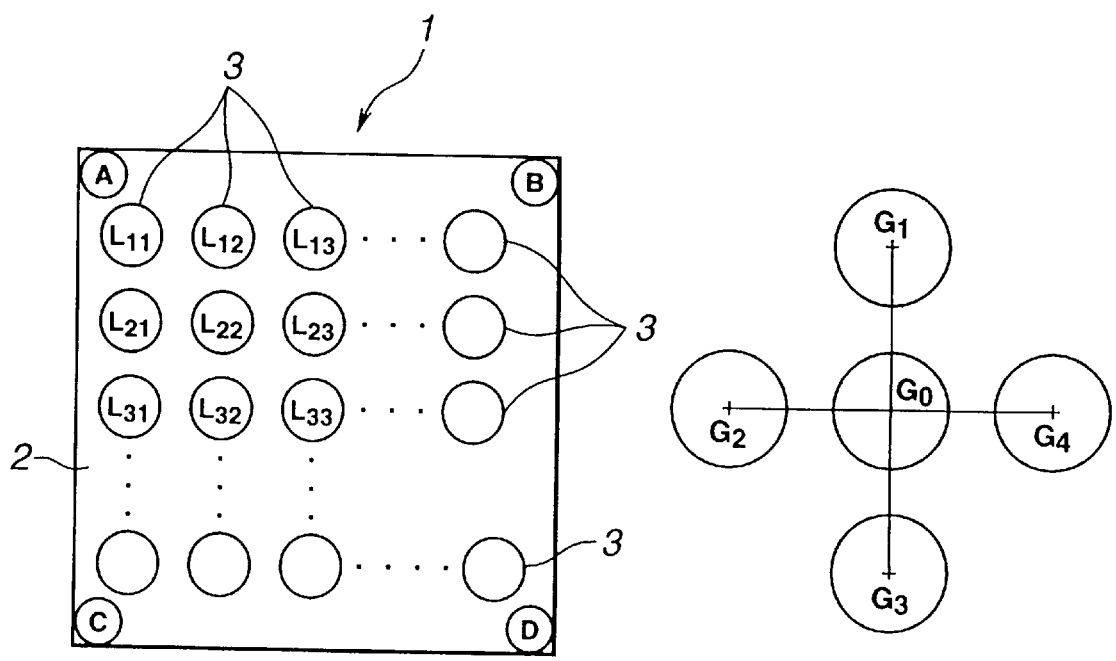
Figure 29:
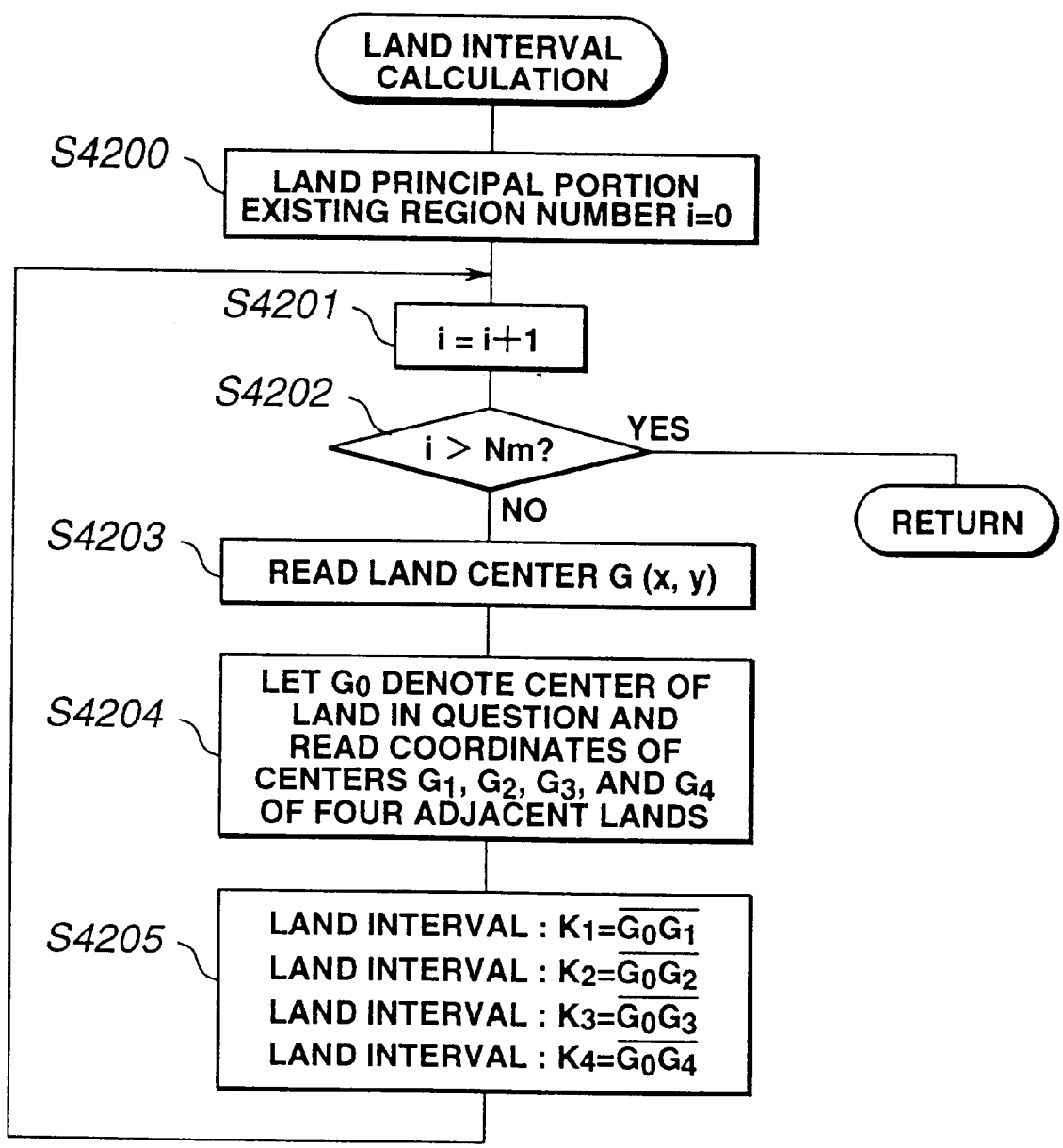
FIG. 29 is a flowchart of details of the land interval calculating process of FIG. 27.

Then, as shown in FIG. 20B, the array or arrangement (L11, L12 . . . etc.) of the lands 4 on the circuit board 1 can be fixed by the aforementioned, fixed center G of each land existing region. FIG. 29 shows a flow of a land interval calculating process. A principal portion of the process resides in the steps S4203–S4205, and at S4203 the coordinates of the center G of the land which is watched at present is read. Then, at S4204, let $G_0$ denote the center of the watched land, and the coordinates G1–G4 of the centers of four lands adjacent the watched land are read. At S4205, the distance between that watched land and each of its adjacent lands is represented by the distance between the centers thereof (K1–K4) and calculated. The thus obtained land distance K1–K4 for every each land (or, land existing region) is stored in the inspection result data memory section 94e shown in FIG. 5 or FIG. 19. In the meantime, the above described process is carried out repeatedly for treatment of each land existing region (S4100–S4102).

Figure 30:
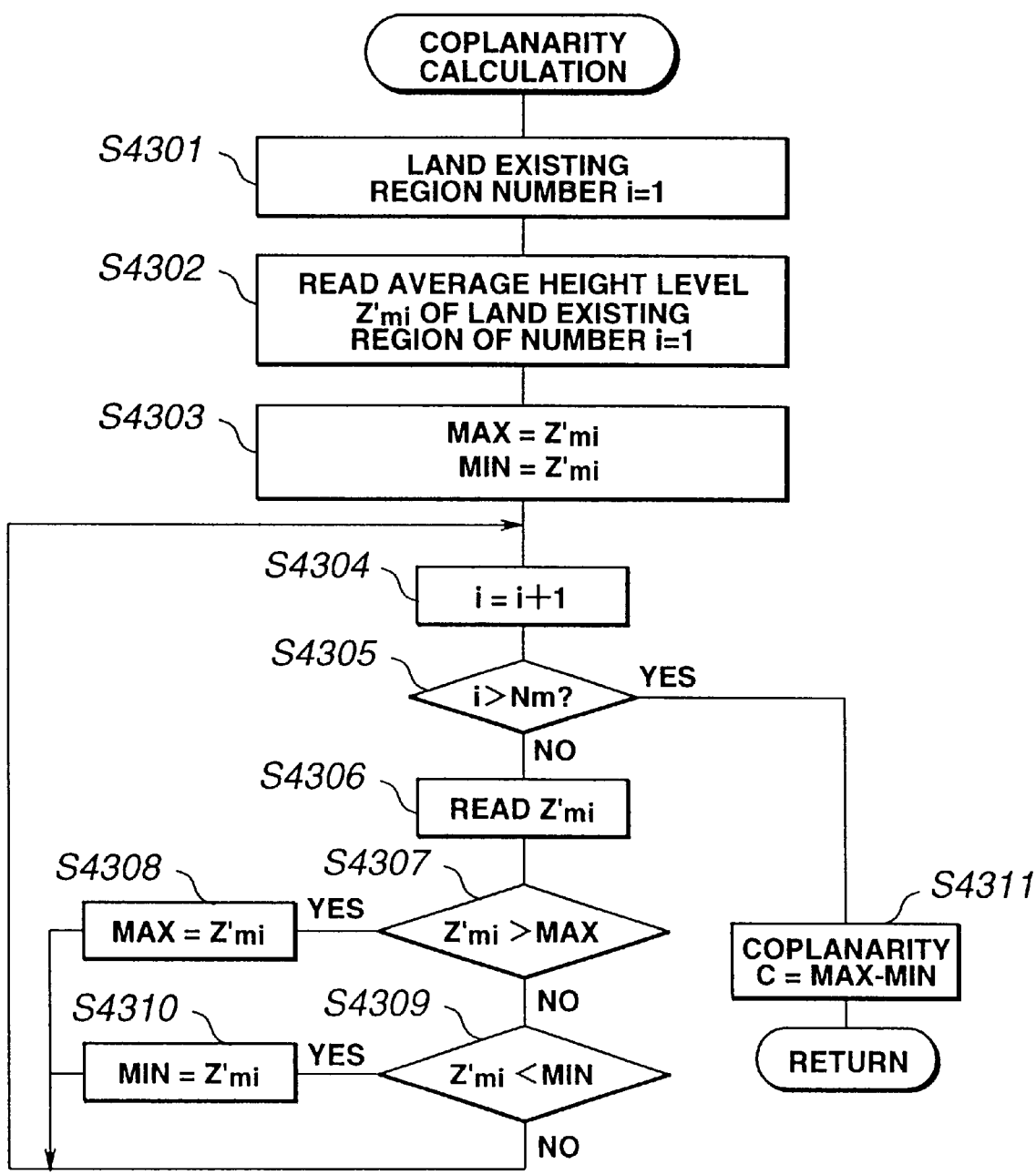
FIG. 30 is a flowchart of details of the coplanarity calculating process of FIG. 27.

FIG. 30 shows a flow of the coplanarity calculating process. At the steps S4301–S4310 of this process, the average land height levels Z'm of the land existing regions are compared one after another to obtain its maximum value MAX and its minimum value MIN. At S4311, the difference (MAX–MIN) is calculated and is used to represent the coplanarity C. This value is stored in the inspection result data memory section 94e shown in FIG. 5 and FIG. 19.

Figure 51A:
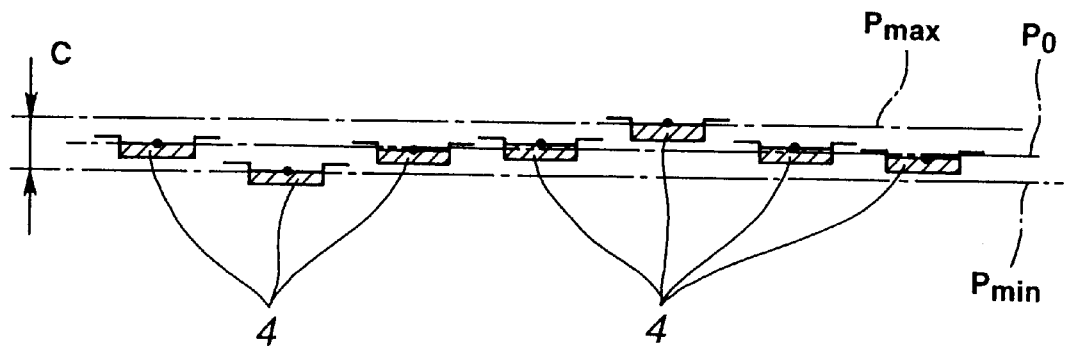
FIGS. 51A and 51B are illustrations of some other concepts of a coplanarity C.

In the meantime, the coplanarity C can be obtained by calculation of the following value. For example, as shown in FIG. 51A, let a least squares plane corresponding to the surface center of each land 4 be a top reference surface P0, let $P_{max}$ be a plane parallel to the top reference surface P0 and in contact with the surface center of the land 4 which is maximum in height, and let $P_{min}$ be a plane parallel to the top reference surface P0 and in contact with the surface center of the land 4 which is minimum in height, the coplanarity C is can be represented by the distance between the planes $P_{max}$ and $P_{min}$. In the meantime, in place of the surface center of the land 4, three-dimensional coordinates (x, y, z) of the maximum height level position within the land existing region can be used.

Figure 51B:
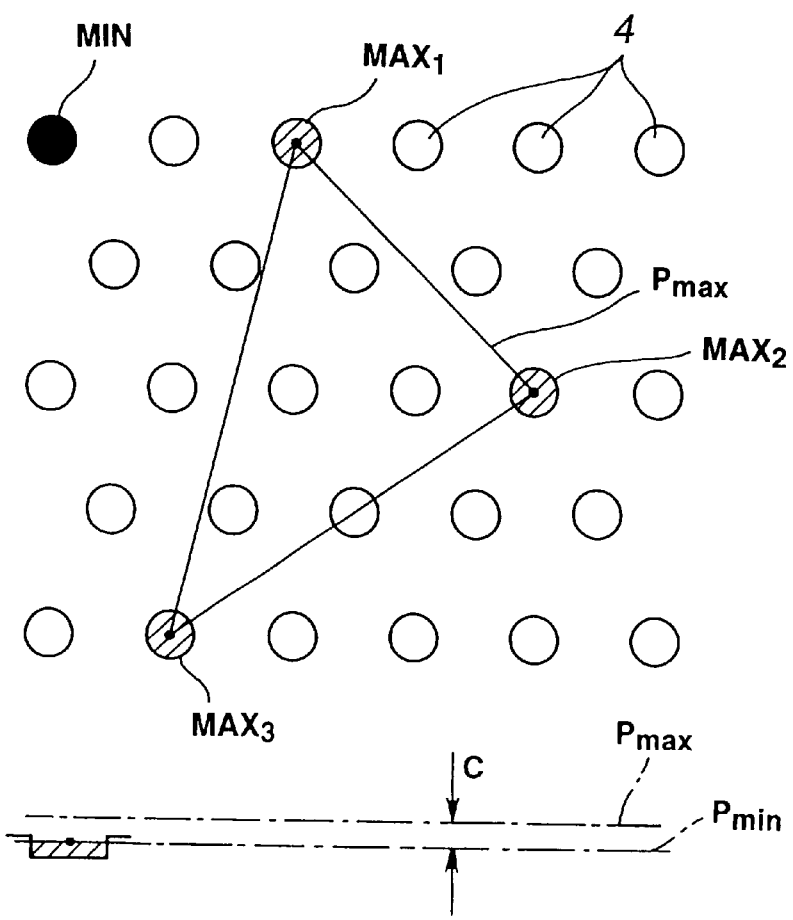

On the other hand, as shown in FIG. 51B, when three land height levels MAX1, MAX2, MAX3 are selected in order of height including the maximum, the coplanarity C can be determined by the distance from the plane $P_{max}$ which is determined by the surface centers of three lands to the surface center of the land which is minimum in height (or the distance between $P_{max}$ and $P_{min}$ where $P_{min}$ is a plane parallel to the plane Pmax and in contact with the surface center of the land which is minimum in height). Further, on the contrary, when three land height levels MIN1, MIN2 and MIN3 are selected in order of height including the minimum, the coplanarity C can be determined by the distance from the plane Pmin which is determined by the surface centers of the three lands to the surface center of the land which is maximum in height (or by the distance between $P_{max}$ and $P_{min}$ where $P_{max}$ is a plane parallel to the $P_{min}$ and in contact with the surface center of the land which is maximum in height).

In the meantime, the coplanarity C can be calculated by the use of the height levels of all the lands on the circuit board 1 or for simplicity calculation may be made by the use of the height levels of only part of the lands 4.

Figure 31:
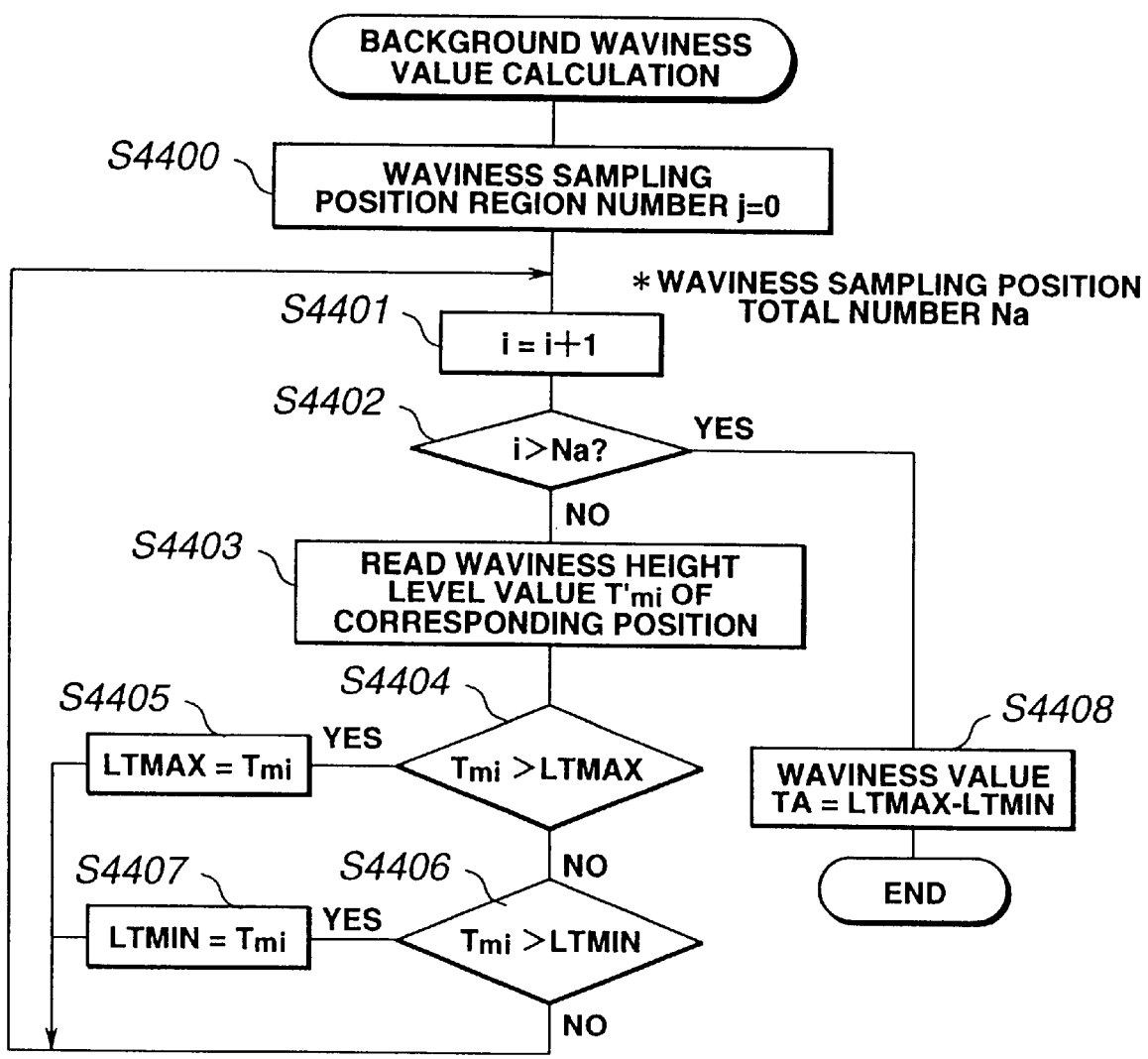
FIG. 31 is a flowchart of details of the background waviness calculating process of FIG. 27.

FIG. 31 shows a flow of a background waviness value calculating process. In this process, a plurality of predetermined waviness sampling positions are set on the background surface section of the inspection surface. A waviness height level Tm corresponding to each sampling position is read, and a waviness value TA (surface waviness information) is calculated by using the thus read waviness height level Tm. Herein, the number of the sampling positions is determined by way of example as Na, the waviness height levels obtained by sampling are compared with each other one by one to obtain the maximum value LTMAX and the minimum value LTMIN, and at step S4408 the waviness value TA is obtained by calculating the difference between them, i.e., LTMAX−LTMIN (S4400−S4408). Larger TA means that the degree of waviness or warping of the circuit board substrate (or inspection surface CP) is larger.

In the meantime, the following value can be calculated for use as a waviness value TA. For example, let a least squares plane corresponding to each sampling position be a reference surface LPO, let $LP_{max}$ be a plane parallel to the reference surface LPO and in contact with the sampling position which is maximum in height, and let $LP_{min}$ be a plane parallel to the reference surface LPO and in contact with the top of the sampling position which is minimum in height, the waviness value TA can be represented by the distance between the planes $LP_{max}$ and $LP_{min}$.

Further, the waviness value TA may be calculated from the sum of the waviness height levels Tm obtained by sampling. For example, as shown in FIG. 22, sampling positions may be set on the inspection surface CP in a way as to correspond to the lands A, B, C and D at four corners of the inspection surface CP, and the waviness value TA may be calculated from the average value of the waviness height levels TmA, TmB, TmC and TmD which are obtained at the respective peripheral regions.

Further, the waviness value may be calculated from the following expressions (4) and (5), i.e., a center line average waviness may be calculated from the expressions (4) and (5) for use as a centerline average waviness. In the expressions, Na is the number of sampling positions and Tmi is the waviness height level corresponding to No. i of those sampling positions.

$$T_A = \frac{1}{Na}\sum_{i=1}^{Na}|Tmi - \mu_{Tm}| \quad (4)$$

$$\mu_{Tm} = \frac{1}{Na}\sum_{i=1}^{Na}Tmi \quad (5)$$

Returning to FIG. 24, the inspection data preparing process is completed by the above. The memory contents of the inspection data memory section 94e under this condition is as shown in FIG. 19. Firstly, an article number is used for fixing the kind of work, and an inspection article number is used for fixing a plurality of works (inspection articles) individually. Both of them are inputted to the inspection data memory section 94e from the input section 100 (refer to FIG. 5) prior to processing. Inspection data $DB_{11}$, $DB_{12}$ . . . ,etc. is stored, one for each land (or each land existing region). Each inspection data includes coordinates of land center G, land diameter D, land height Z, land region S (area of land existing region), and land intervals K1−K4. Further, the calculated coplanarity C with respect to the land array on the circuit board 1 is also stored.

Figure 32:
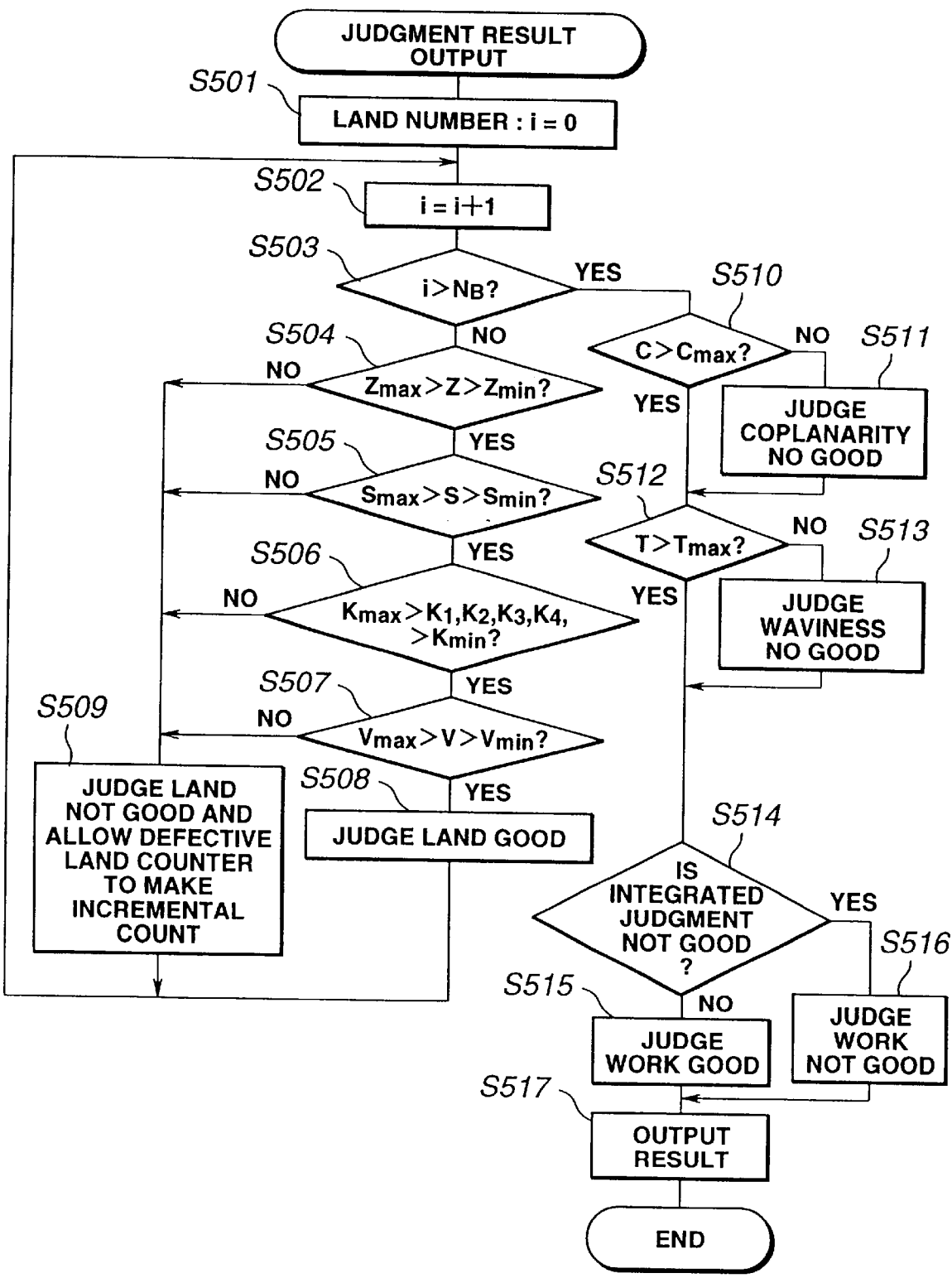
FIG. 32 is a flowchart of details of the judgement/result output process of FIG. 24.

In FIG. 24, the control proceeds to the judgment/result output process at S5. The flow of the process is shown in FIG. 32. Firstly, since data on acceptance ranges of various inspection parameters which are the objects of judgment (herein, D, S, K1−K4, C, TA) are stored in the inspection standard data memory section 94d, one for each circuit board 1 article number, so the data for a corresponding article number is read. In the process steps S501−S509 in FIG. 32, when the parameters D, S, K1−K4 and V of the aforementioned inspection parameters obtained for all of the lands of the work are within the acceptance range, it is judged that the land is good or non-defective (S508)), and when not, it is judged that the land is not good or defective (S509). The result of judgment is stored in the inspection result data memory section 94e in FIG. 19 in such a manner as to be associated with the data of each land (in FIG. 19, good or non-defective is indicated by ◯ and not good or defective is indicated by x). Further, at S509, the number of defective lands detected is counted by the use of a defective land counter ND and is stored in the inspection data memory section 94e. The work with a defective land or lands which are of such a number equal to or larger than a predetermined value (in this embodiment, for example, 1) is judged as bad (x), and the work with a land or lands which are of such a number less than the predetermined value is judged as good (◯).

When such judgment as described above is carried out on all of the lands and completed, the process proceeds from S503 to S510 to carry out judgment on the coplanarity. That is, in case the coplanarity C measured with respect to the work exceeds a tolerance $C_{max}$, it is judged that the work is no good or defective (x), whereas in case the coplanarity C does not exceed the tolerance $C_{max}$ it is judged that the work is good (◯). The result of judgment is stored in the inspection result data memory section 94e. Then, the process proceeds to S514 to carry out integrated evaluation or judgment. In this connection, in case the work has been decided as good on both the number of defective land or lands and the coplanarity its integrated judgment is acceptance (◯), whereas in case it has been decided as bad on either of the judgments its integrated judgment is rejection. The result is also stored in the inspection result data memory section 94e. The above results are outputted from, for example, a monitor 98 or printer 102 in FIG. 5 on the basis of memory contents of the inspection data memory section 94e (S517). By the above process steps, the judgment/result output process is completed. Such process steps S1−S7 in FIG. 24 are carried out for each of the inspected works in sequence, and when the process steps for all the works are finished the data analysis/inspection judgment process is completed.

Referring now to FIGS. 35 to 38B and FIGS. 43 to 49, a display of an inspection result will be described. Firstly, the display is executed by means of the monitor 98 shown in the block diagram of FIG. 5. The CPU 86 carries out the display control by way of a monitor control section 96 on the basis of a display control program stored in a memory section 94f of the memory 94. In the meantime, the monitor 98 functions as a height level value distribution display means, an individual land mapping image enlarged display means, an inspection information content display means, a detection information-by-position display means, and a work arrangement display means. Further, the CPU 86 functions a land quality (good/no good) judging means, a defective land position display control means, a defective land existing region enlarged display means, a work quality (good/no good) judging means, a defective work display control means, and a measurement system drive control means. Further, the mouse (pointing device) 100*b* serves, together with the CPU 86, as a defective land existing region selecting means and an individual land selection region setting means.

Figure 34A:
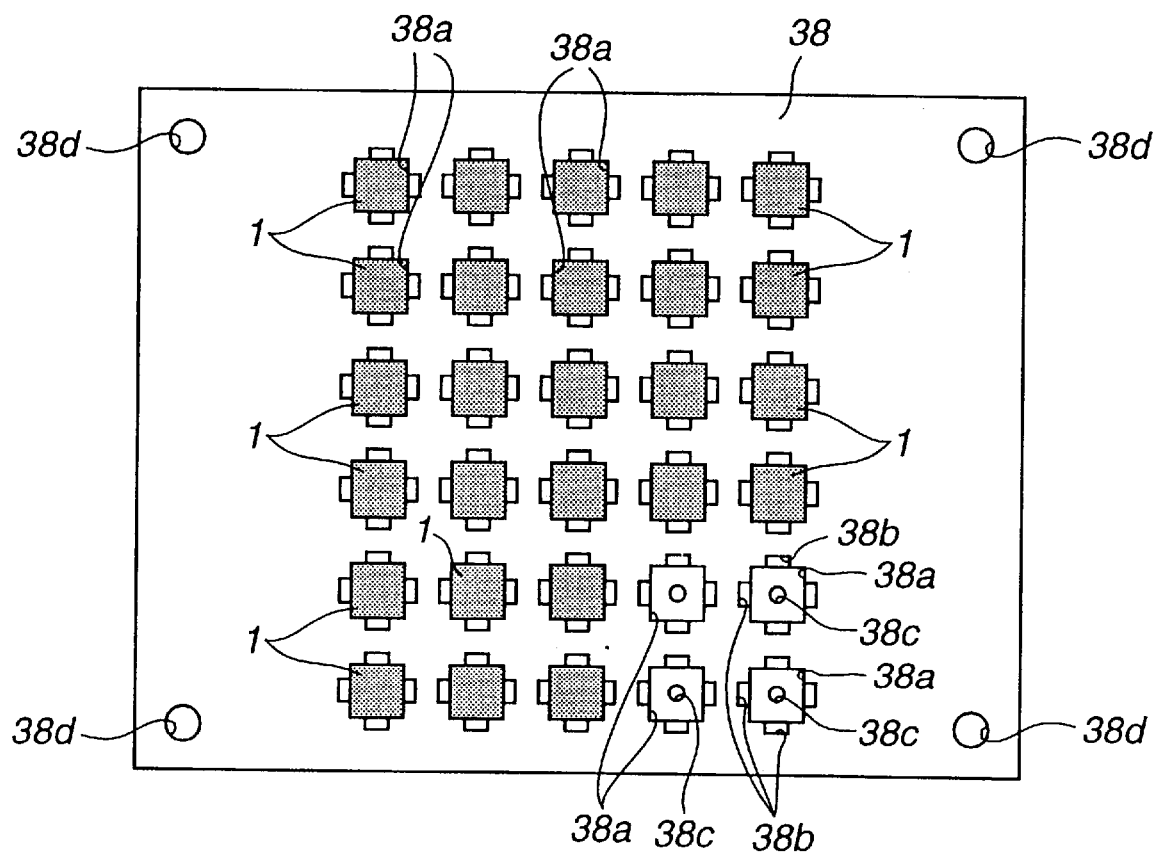
FIG. 34A is a plan view of a work holder in a state of having installed thereon works.
Figure 34B:
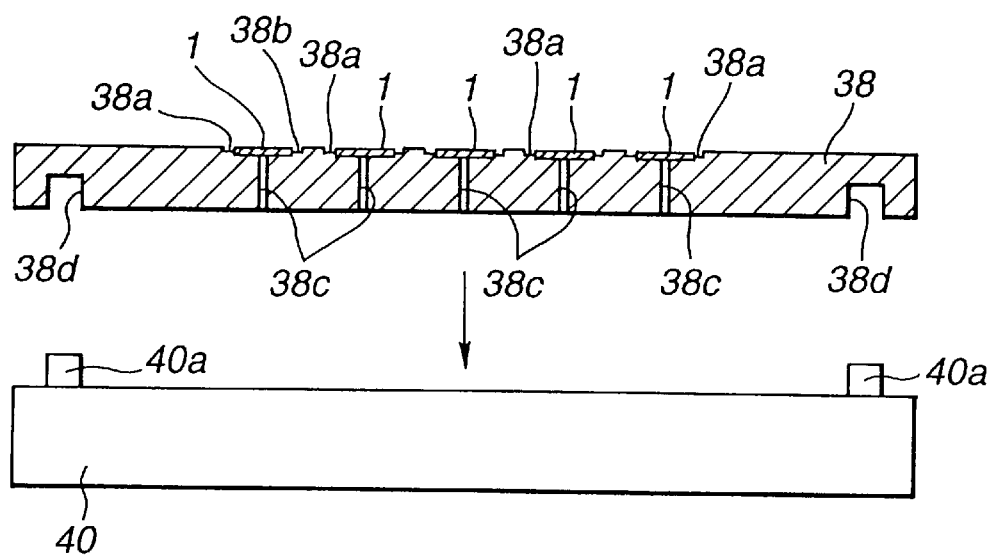
FIG. 34B is a cross sectional view of the work of FIG. 34A, together with an x-y table of FIG. 4.
Figure 43:
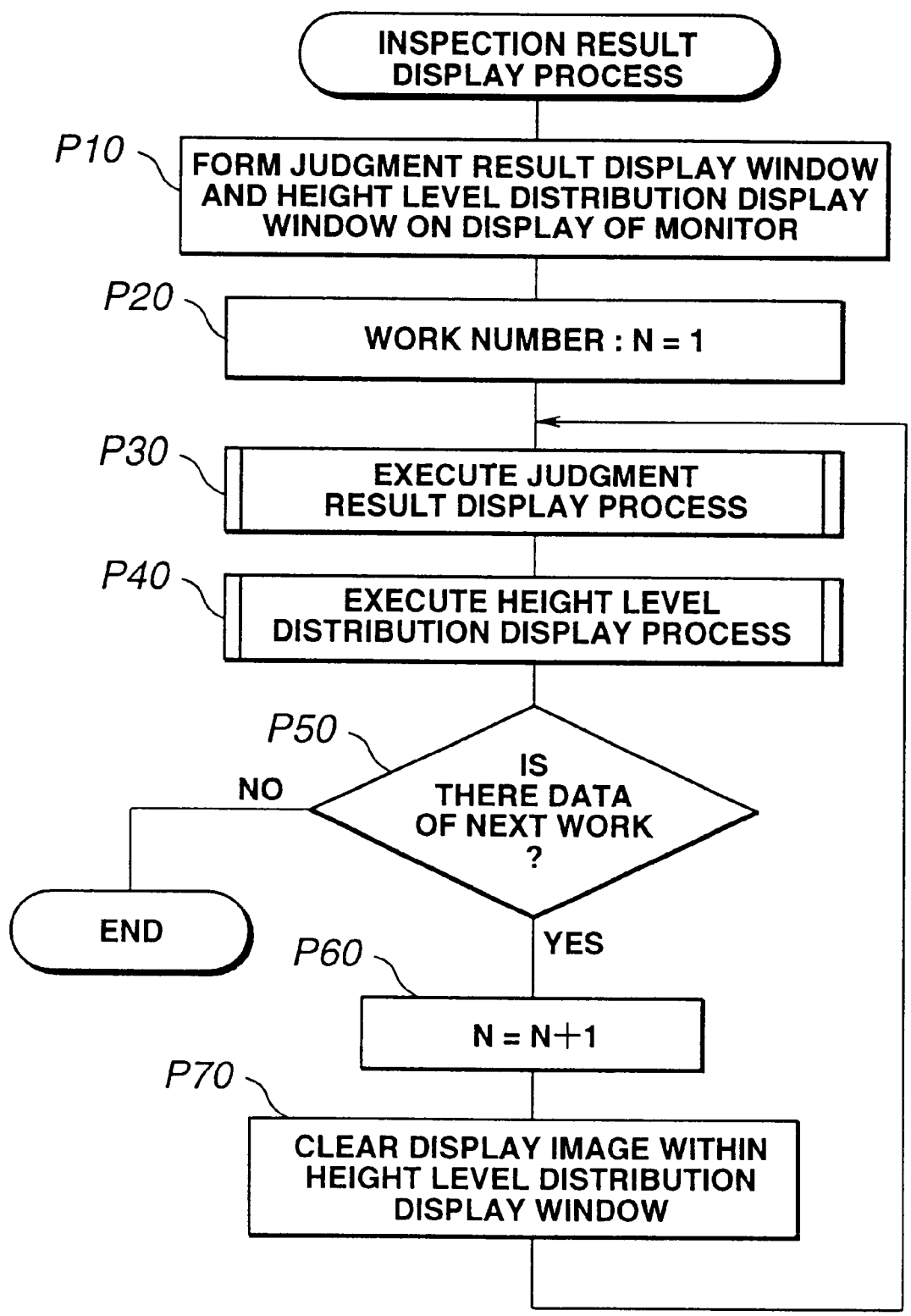
FIG. 43 is a flowchart of an inspection result display process.

FIG. 43 is a flowchart showing a flow of an inspection result display process. Firstly, at P10 and as shown in FIG. 36, a judgment result display window 300 and a height level value distribution display window 301 are displayed on the screen of the monitor 98. The judgment result display window 300 serves as a work arrangement display means, and the height level value distribution display window 301 serves as a height level value distribution display means. The judgment result display window 300 consists of display cells 300*a* which are in one-to-one correspondence to depressions 38*a* of the work holder 38 shown in FIGS. 34A and 34B (i.e., works 1) to serve as individual display sections and arranged in a gridiron or checkered pattern.

Figure 36A:
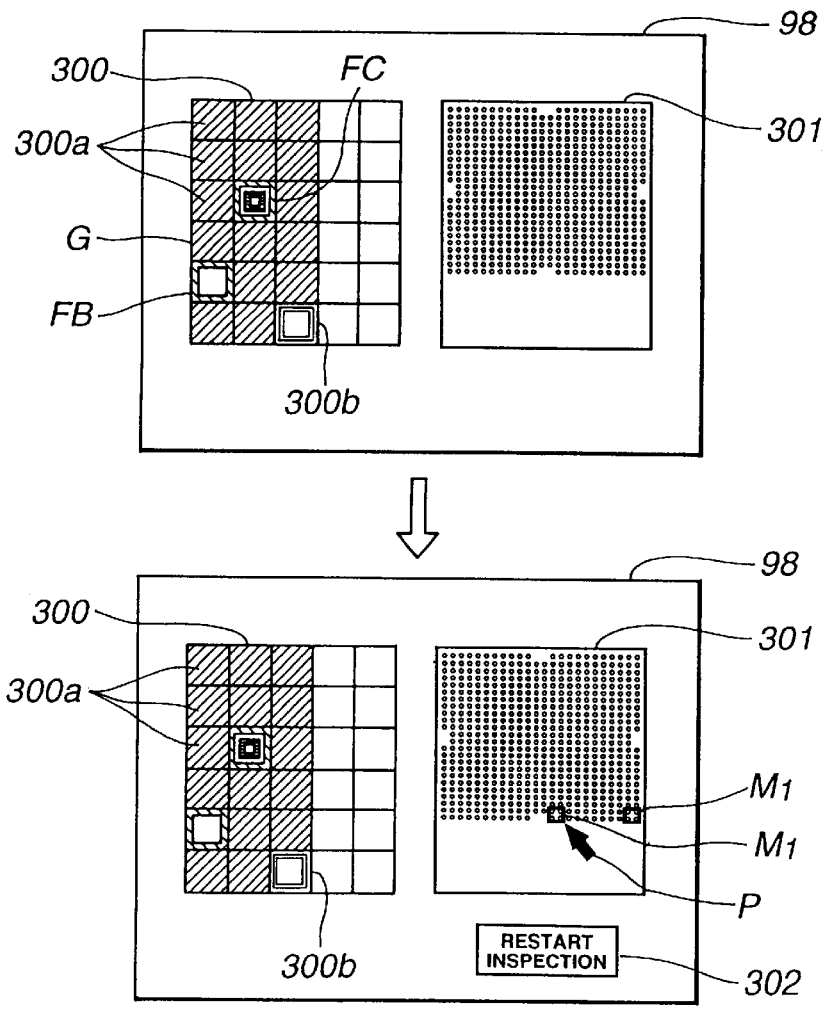
FIGS. 36A and 36B are illustrations of a display format of a judgment result display window and a height level value distribution display window.
Figure 44:
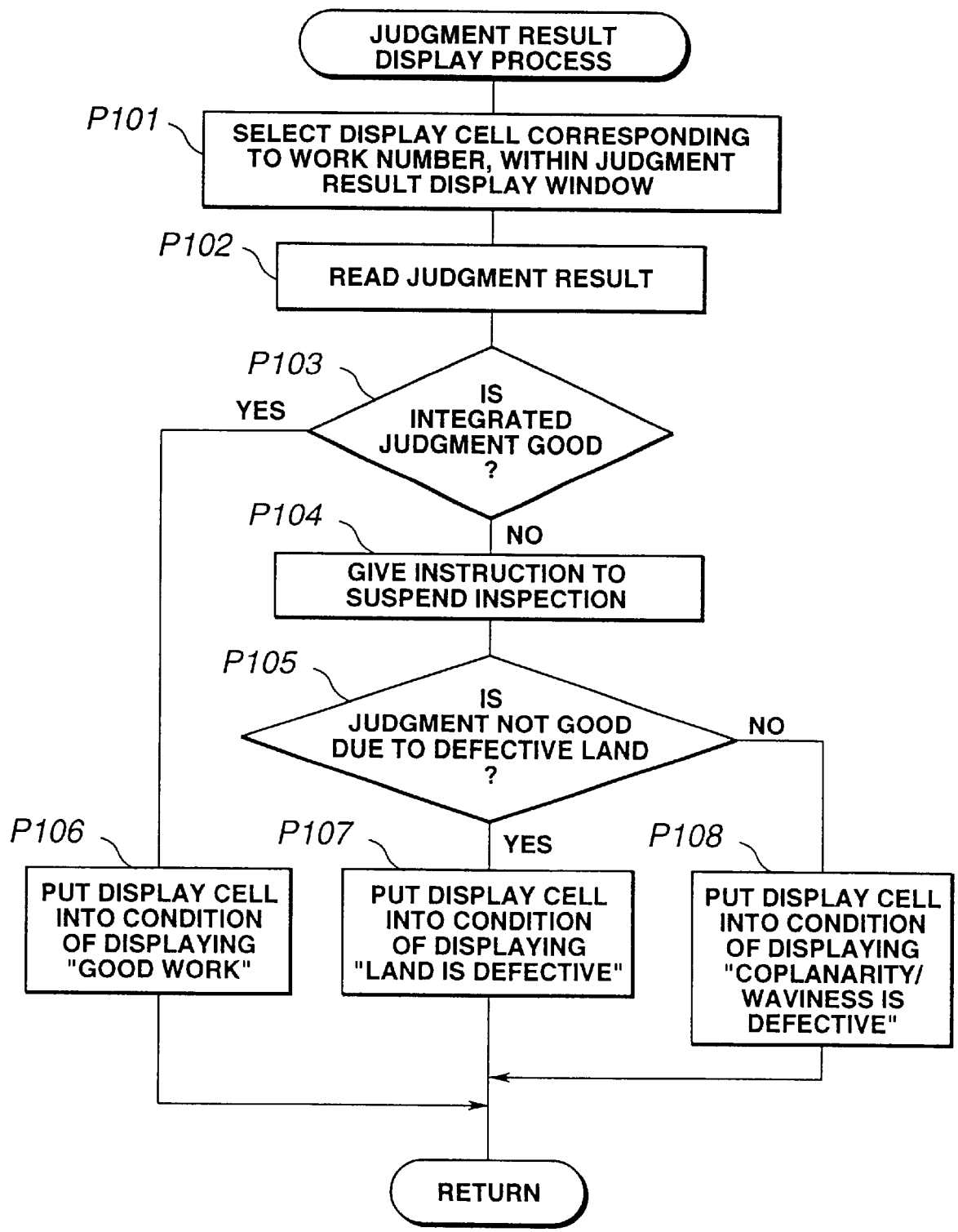
FIG. 44 is a flowchart of a judgment result display process.

FIG. 44 is a flowchart showing a flow of a judgment result display process. Firstly, at P101, one of the display cell s 300*a* within the judgment result display window 300, which corresponds to an object to be processed at the present time (hereinafter will be referred to as current work), is selected. In this embodiment, in case the result of judgment on the current work is not known, a marker 300*b* is displayed within the selected display cell, as shown in FIG. 36A, so that the position of the current work can be discriminated from others with ease.

Then, the process proceeds to step P102 of FIG. 44. At step P102, when the judgment result has been produced, it is read from the inspection result data memory section 94*e*. In the event the integrated judgment is acceptance (○), the process proceeds to step P106 where the display cell is put into a display condition of indicating "good work" (i.e., in FIG. 36A, a display condition indicated by G, for example, a display condition attained by painting out the display cell bright green). On the other hand, in the event the integrated judgment is no good (X), the process proceeds to step P104 where an instruction to suspend inspection is transmitted to the measurement system control section 51 of FIG. 5.

Figure 23:
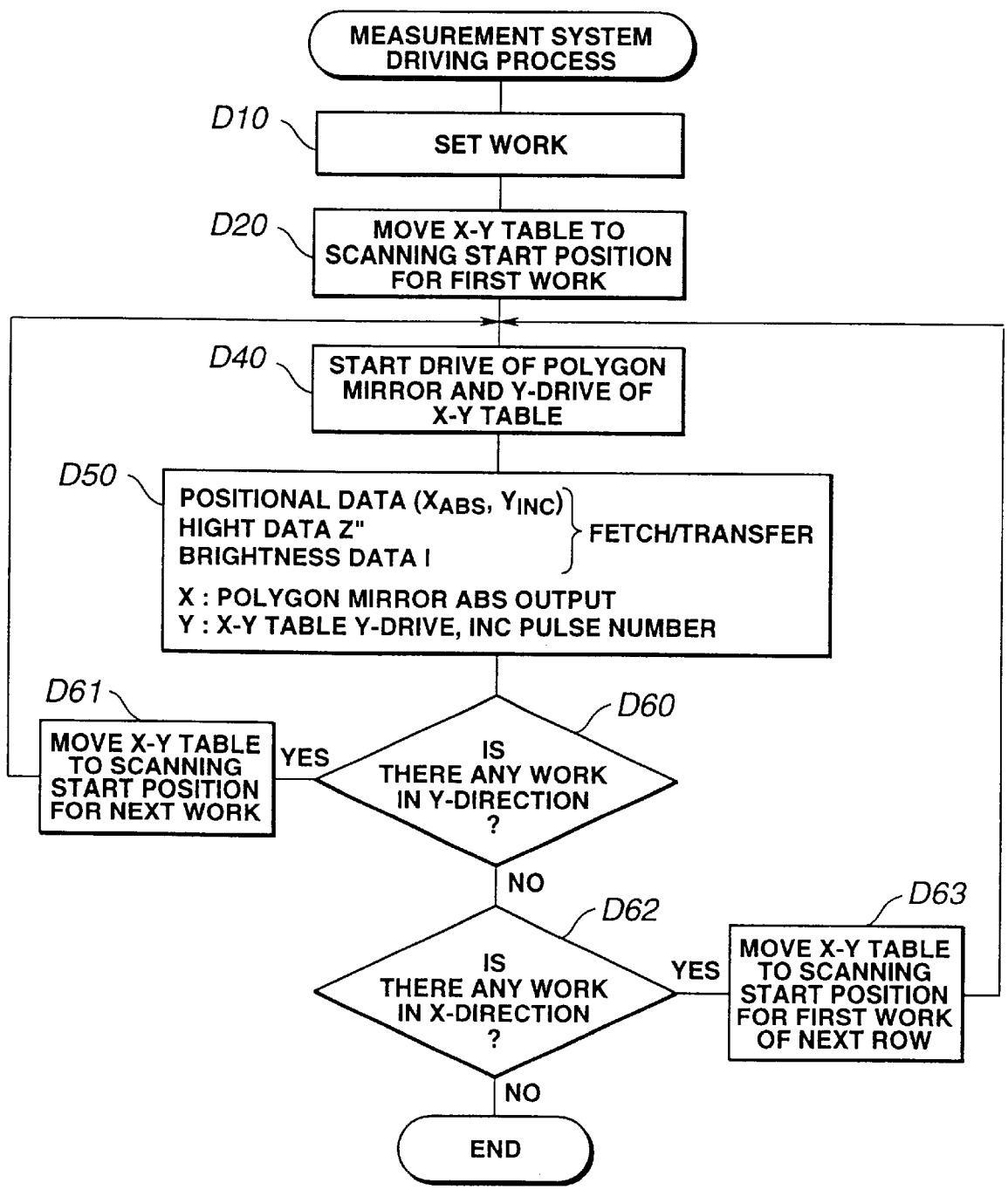
FIG. 23 is a flowchart of a control process for a drive section of the measurement system of FIG. 2.
Figure 49:
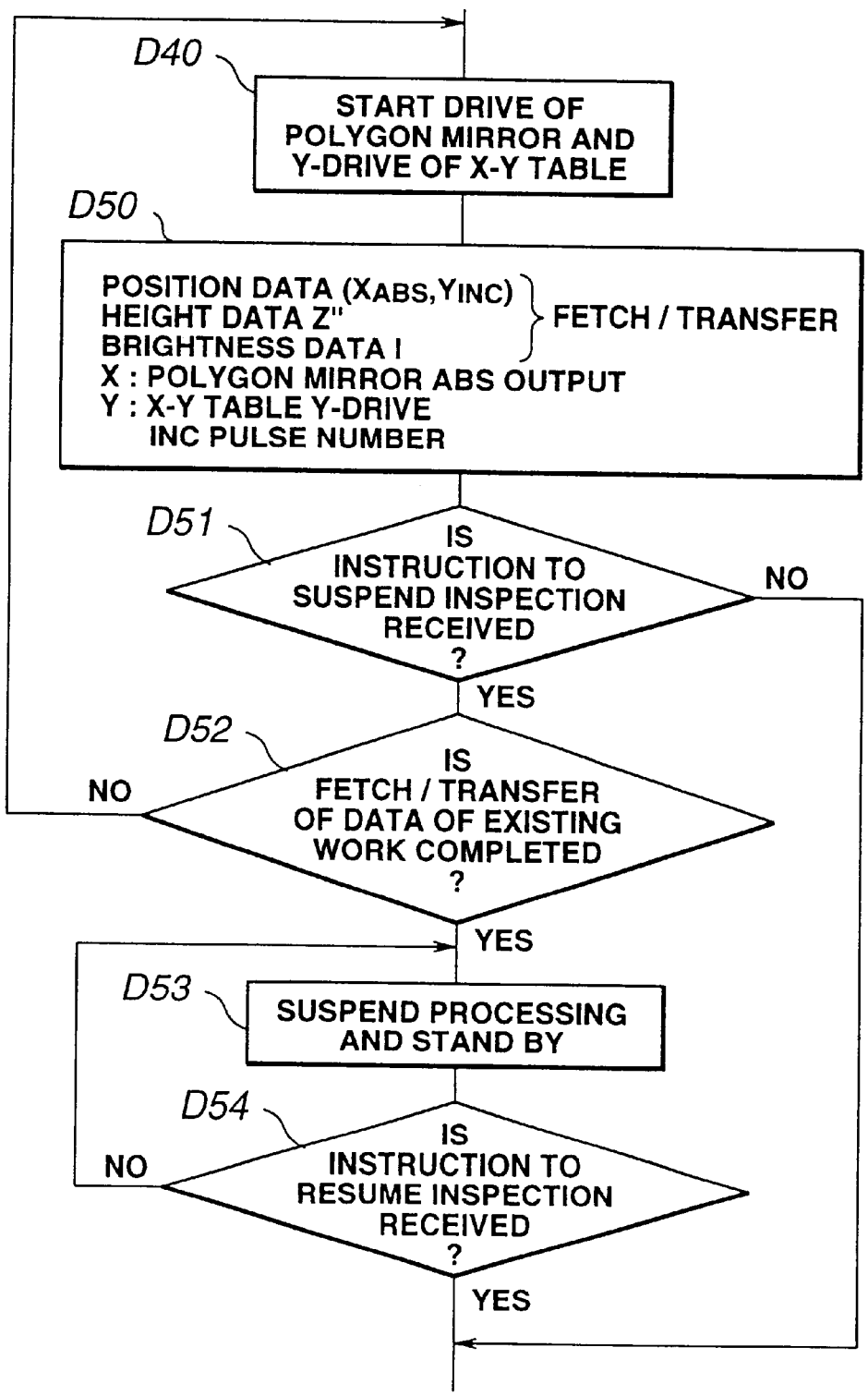
FIG. 49 is a flowchart which is a modified portion of the measurement system driving process of FIG. 23 and which is executed for suspending an operation in case a defective work is found.

In response to the instruction, there is executed on the measurement system control section 51 side such a process that is substantially similar to that shown in FIG. 23 except that the steps D40 and D50 are replaced by the steps D40 to D54 of the process of FIG. 49. That is, at D51, when the instruction to suspend inspection is received, the polygon mirror drive and y-drive of the x-y table 40 (refer to FIG. 4) for beam scanning at D40 and the data fetch/transfer process at D50 are continued until the process for the work now subjected to measurement is finished, and then the process proceeds to step D53 for standby. At step D54, the suspended condition is maintained until an instruction to restart inspection is received. In the meantime, at D51, in case an instruction to suspend inspection is not received, the steps D52 to D54 are skipped and the process proceeds to step D60 in FIG. 23 onward.

Returning to FIG. 44, at step P105, it is confirmed on the basis of the judgment result data in the inspection result data memory section 94*e* whether the integrated judgment of no good is due to occurrence of a defective land or not. When it is due to occurrence of a defective land, the process proceeds to step P107 where the corresponding display cell 300*a* is put into a display condition of indicating "land is defective" (i.e., in FIG. 36A, a display condition indicated by FB, for example, a condition in which the cell is surrounded by a red frame). On the other hand, in case the integrated judgment of no good is not due to occurrence of a defective land but due to occurrence of a defect of a coplanarity, background (circuit board substrate surface) or waviness value, the process proceeds to step P108 where the display cell 300*a* is put into a display condition of indicating "coplanarity/waviness is defective" (i.e., in FIG. 36A, a display condition indicated by FC, for example, a dual-frame consisting of a blue frame section and a red frame section is displaced in the cell).

Figure 45:
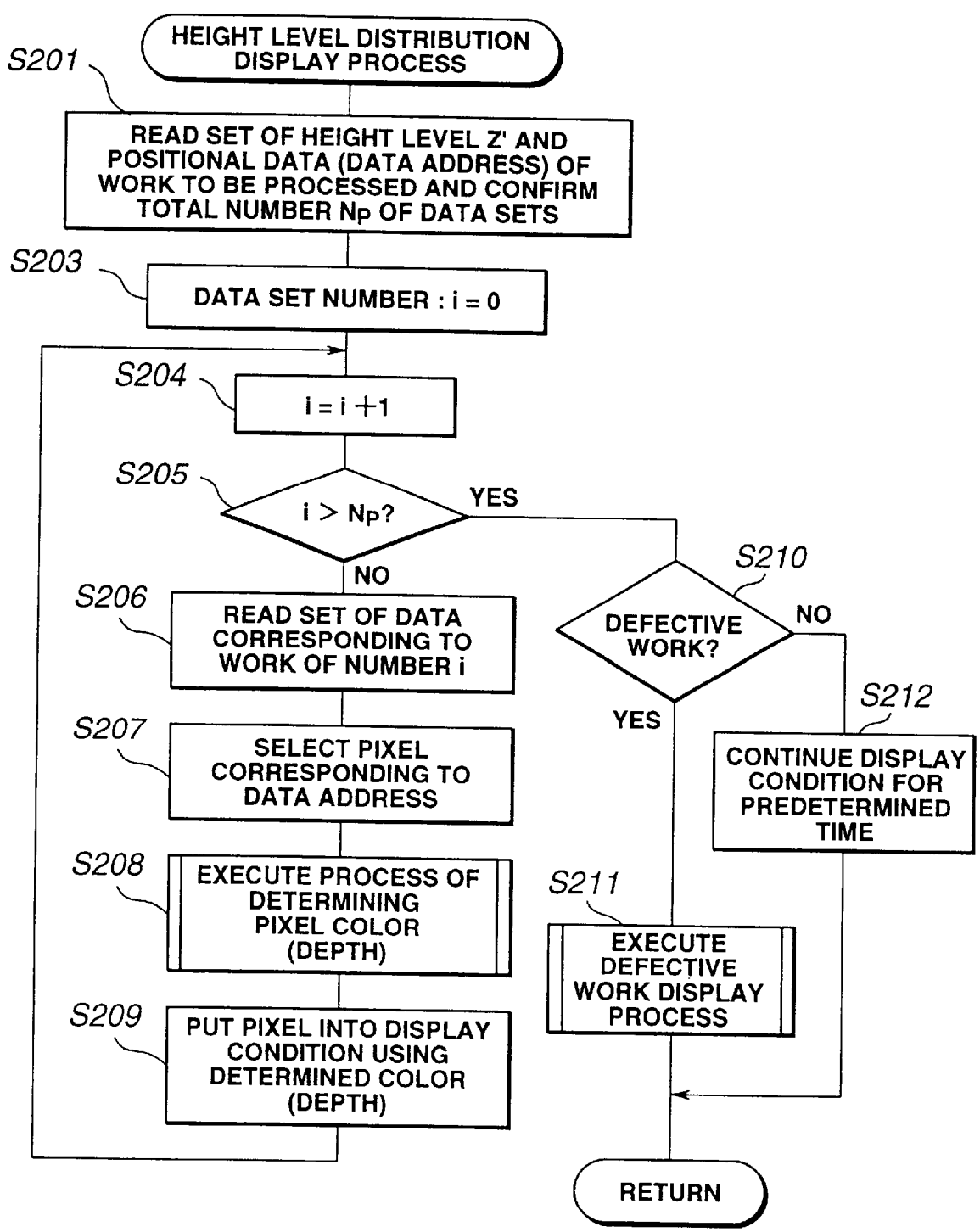
FIG. 45 is a flowchart of a height distribution display process.

Then, the height distribution display process in FIG. 45 is executed. Firstly, the corrected height level value data Z' (FIG. 12B) of the work which is an object to be displayed, is read in a way as to form a data set together with the position data described in the form of data address, sequentially (P206). One of the pixels within the height level distribution value display window 301, which corresponds to the data address of the read data set, is selected (P207), and it is determined, in case, for example, the monitor 98 is a color monitor and is set to a color display mode, the color of the pixel (P208). However, the display can be done on the basis of light and dark (i.e., density) of gray color, and in such a case the density or brightness of the pixel is determined at step P208. Hereinbelow, description will be made by way of example to a color display.

Figure 35:
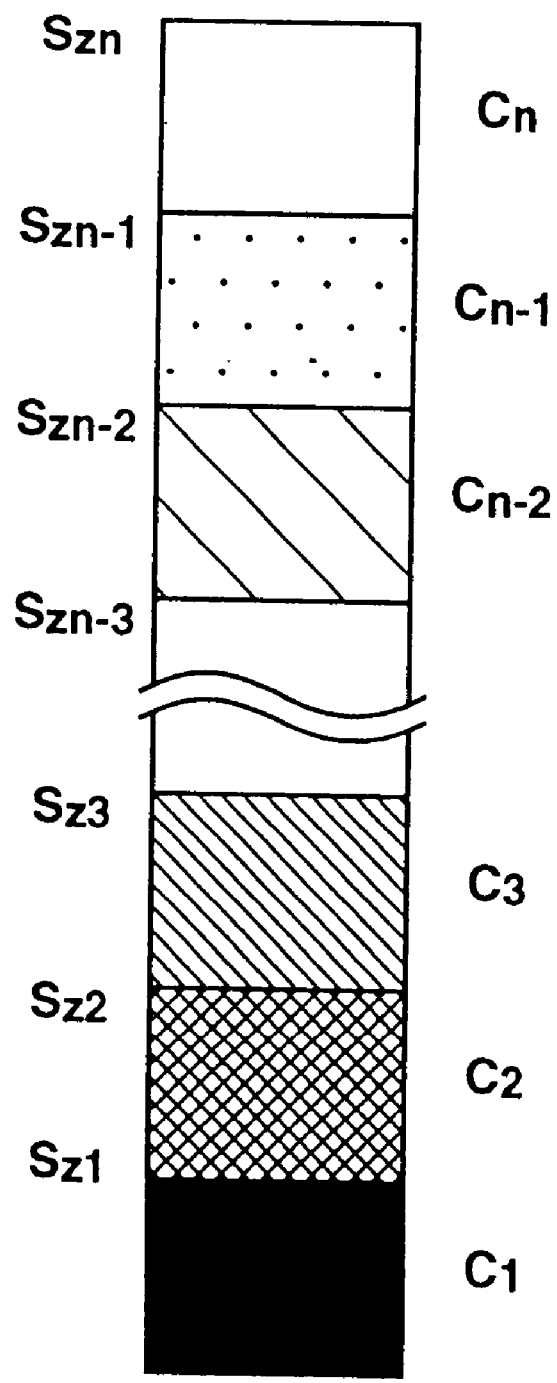
FIG. 35 is an illustration of a relation of threshold levels set for height ranges and predetermined colors of pixels.
Figure 46:
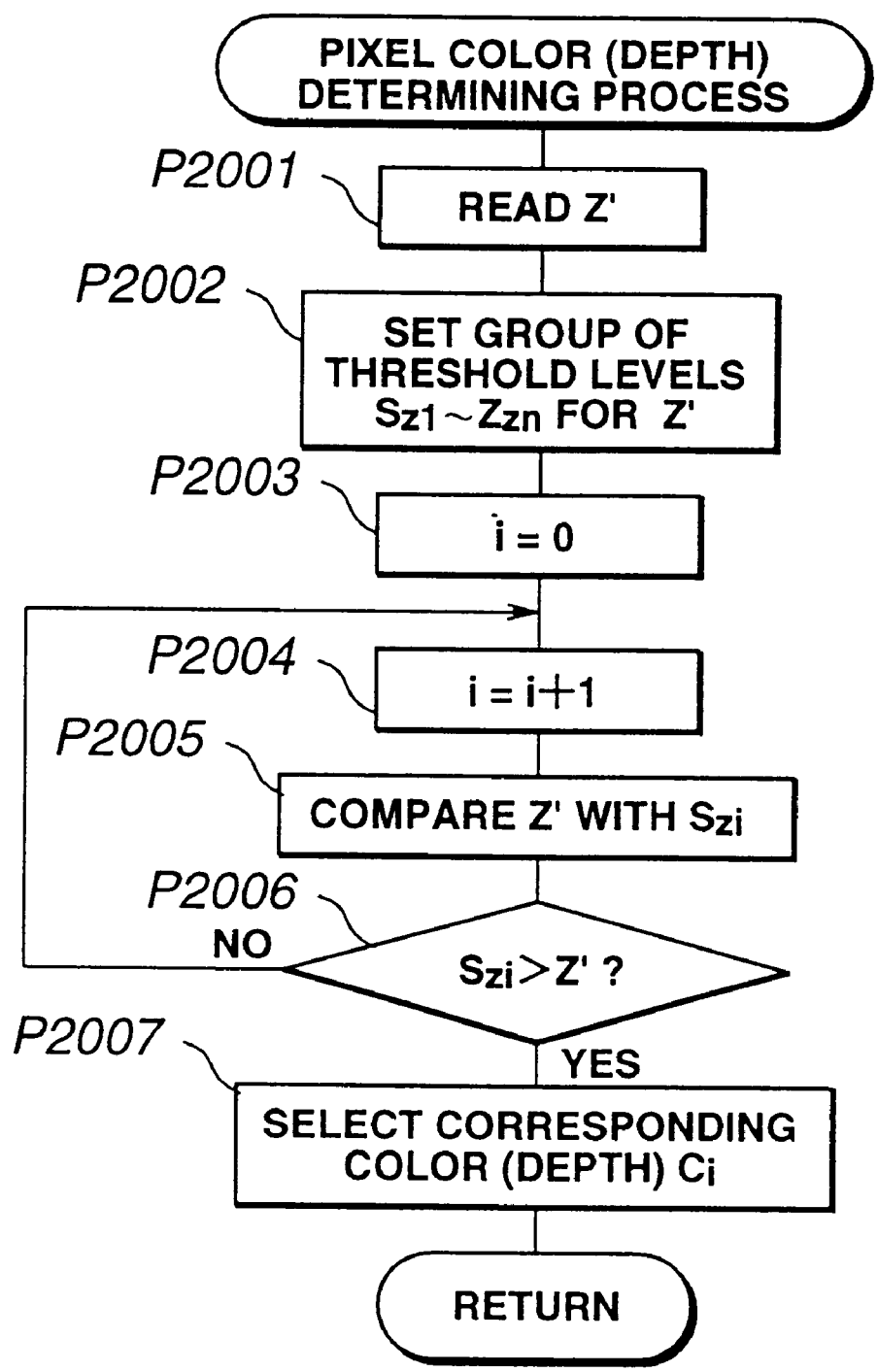
FIG. 46 is a flowchart of a pixel color (depth) determining process.

FIG. 46 is a flowchart showing a flow of a pixel color determining process. That is, as shown in FIG. 35, the ranges of height level values are defined by setting a group of threshold levels Sz1, Sz2, . . . Szn (P2002), and colors (density) C1, C2 . . . Cn different from each other are allotted to the height level value ranges, each of which is defined between adjacent two of threshold levels. At P2001, the height level value Z' is read, while at the same time the read value is compared with the threshold levels sequentially to find a corresponding height level value range and a corresponding color (P2003–P2006).

Figure 37A:
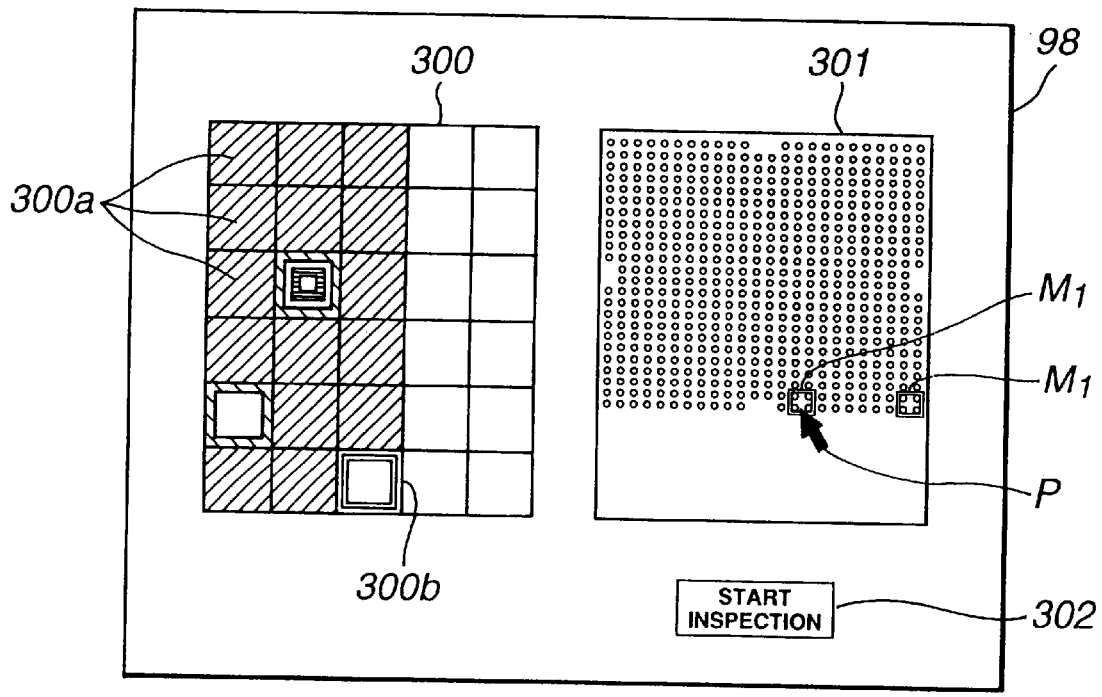
FIGS. 37A and 37B are illustrations of an operation for instructing enlargement on a height level value distribution display window and an enlarged display of mapping image.

Returning to FIG. 45, the pixel is put into a condition of display by means of a determined color (P209). This process is repeated for the data sets which are read in sequence, whereby as shown in FIG. 36A or 37A, the distribution of height levels at respective positions within the inspection surface are displayed by color mapping within the height level distribution value display window 301. In the meantime, in FIG. 37A, within the height distribution value display window 301, the mapping image is displayed in such a magnification that the entire inspection surface CP can be displayed.

Then, the process proceeds to step P210. At step 210, when the work is defective (e.g., defective in land or in coplanarity/waviness value), the control proceeds to step P211 where the monitor 98 is put in a defective work display mode. On the other hand, when the work is good, the process proceeds to step P212 where a process of continuing the display condition of displaying the mapping image for a predetermined time. In this connection, since the step P104 in FIG. 44 for giving an instruction to suspend inspection is skipped, the measurement process is continued as it is, to allow , if the next work to be processed exists, the process to proceed, in FIG. 43, from P50 to P70 by way of P60 to clear the display within the height distribution value display window 301. Thereafter, the process returns to P30 to repeat the process P30 onward.

Figure 42A:
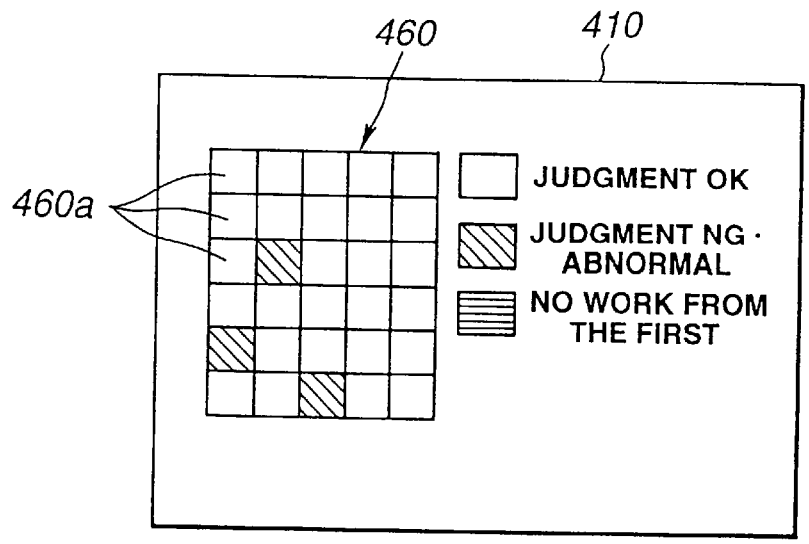
FIGS. 42A and 42B are illustrations of a display of work quality (good/no good) judgment result by a monitor of the sorting unit of FIG. 49.
Figure 47:
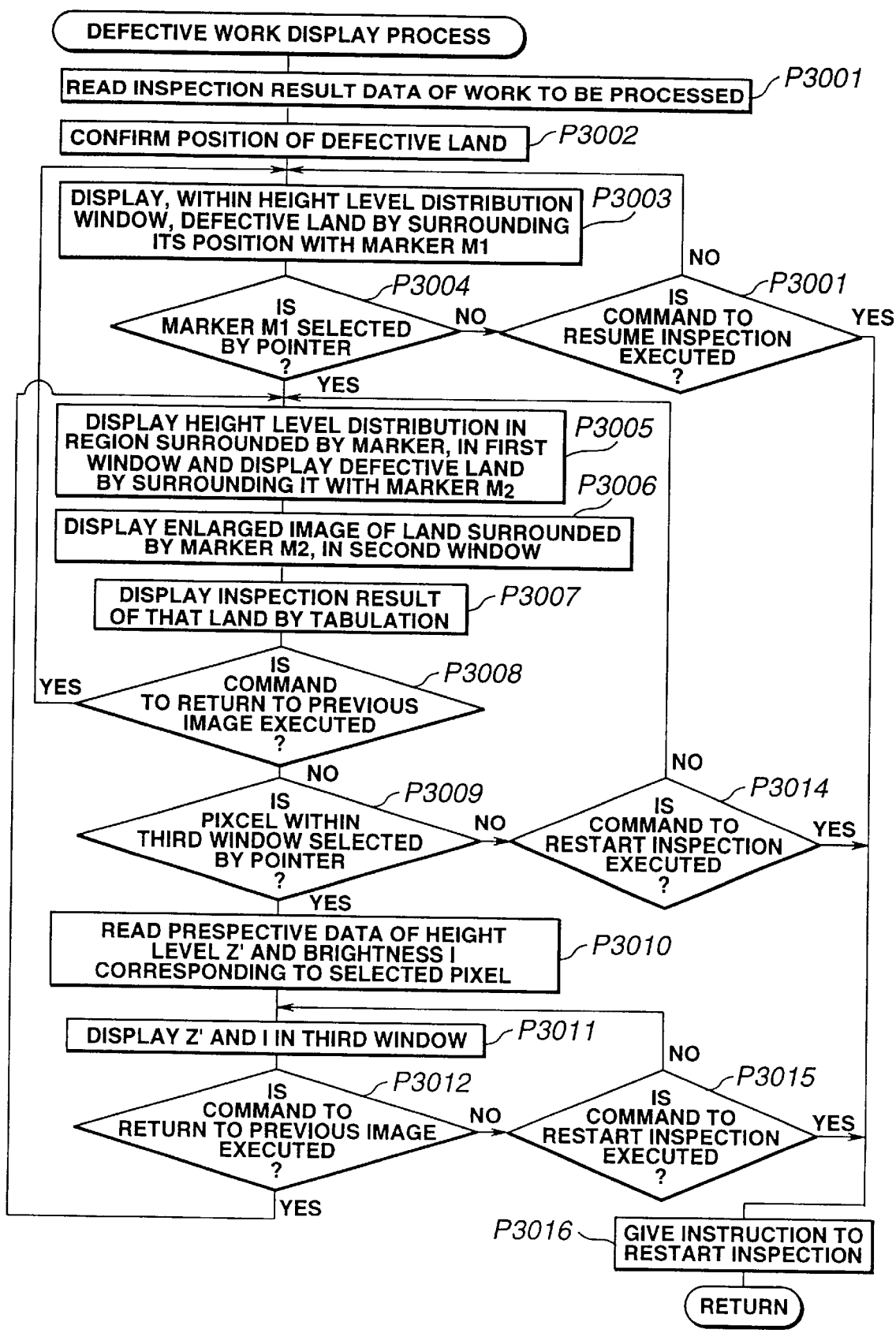
FIG. 47 is a flowchart of defect display process.

On the other hand, in case the defect display process at P211 is executed, various manipulations of image shown in FIG. 47 can be attained under the condition where the measurement process is suspended. Firstly, at P3001 the inspection result data of the corresponding work is read from the inspection result data memory section 94e (FIG. 19), and at P3002 a position of a defective land is confirmed. Then, the process proceeds to step P3003 where, as shown in FIGS. 41A and 42A, a region of a predetermined area including the position of the defective land is surrounded by a maker M1 on the mapping image displayed in the height distribution value display window 301, for thereby displaying the position of the defective land. In the illustrated example, defective lands are caused at two places, and the region surrounded by each marker M1 corresponds to an enlargement designating region. In the meantime, in place of or in addition to surrounding the region by the marker, inversion of the display color within the region or the like method of changing the display condition can be done. On the other hand, a pointer P which is movable on a display or screen by the operation of the mouse 100b in FIG. 5 is displayed within the height distribution value display window 301.

Then, in order to display an enlarged defective land, the position indicated by the pointer P is put within the marker ML and a selection command is executed by clicking a mouse button which is not shown (P3004). By this, the process proceeds to step P3005, the display image of the monitor 98 is cleared and changed into one shown in FIG. 37B. In this display image, there are shown three windows, i.e., a first window 303, second window 304 and a third window 305.

Within the first window 303 of those, there is displayed the region (enlargement designating region) surrounded by the marker M1 in the previous display image (FIG. 37A), which is enlarged, for example, in such a manner as to occupy almost all of the display region of the window 303, and further there is displayed a region of a defective land which is surrounded by a marker M2 (P3005). The region surrounded by the marker M2 corresponds to an individual land selection region. On the other hand, within the second window 304, there is displayed a mapping image of the region surrounded by the M2 and therefore a mapping image of the land within that region, which is enlarged in such a manner as to occupy almost all of the display region of the window 304 (P3006). Within the third window 305, there is displayed an inspection data of the land represented by the thus enlarged mapping image, which is read from the inspection result data memory section 94e (FIG. 19), e.g., numerical values such as the above described D, Z, S, K1–K4, C, TA, etc. are read from the inspection result data memory section 94e and shown (P3007). In the meantime, a judgment result may be displayed in addition to such numerical values.

For example, description being made by way of example to the second window 304, the height levels at the respective positions on the inspection surface can be known or recognized on the basis of the color or density of the respective pixels within the window, for example, a land existing region is represented by a display region which is nearly equal in color since a variation of the height level within the region is not so large if the land is normal. Further, around the land existing region, there is formed a silhouette region which lacks a data of height level value as described before (in the illustrated example, the silhouette region is shown as a region whose height level is nearly zero). Outside the silhouette region, there appears a background region, which is a little higher in height level than the land surface, in the color different from that of the land surface. In this manner, from the color distribution on the mapping display, the land existing region and the background region can be distinguished from each other with ease.

Further, in case the height level of the land surface is too high or too low, the region of the corresponding land appears in the color different from that of other normal land, so such abnormality can be distinguished or recognized with ease. On the other hand, in case the land is abnormal in the area or diameter, the corresponding land existing region appearing on the mapping image differs in the area or diameter from that of a normal land, so such abnormality can be distinguished with ease. Further, in case an abnormality due to a flaw or the like occurs in the land top face, the abnormal portion appears in the same kind of color as the silhouette region since irregular reflection of the inspection beam occurs at that abnormal portion to cause the abnormal portion to lack the data of height level values, so such abnormality can be also distinguished with ease.

Further, since display of the height level values by mapping is also made as to the surface of the circuit board substrate, i.e., the background region, even macroscopic warping or waviness of the circuit board substrate surface can be recognized with ease on the basis of the difference in color when the surface of the circuit board substrate is displayed in such a condition by means of the height level distribution value display window 301 of the low magnification as shown in FIG. 40A. In this manner, the height level values at respective positions are displayed by color mapping, so it becomes possible to grasp quite intuitively the information on the land formed condition and waviness of the circuit board substrate surface.

In case of inspection of a circuit board of the kind in which a land surface is nearly flush with a substrate surface, the difference in the height level between the land surface and the background surface is nearly zero. Accordingly, by such mapping of the height level distribution as described above, it is difficult to distinguish the land existing region from the background surface. To solve this problem, reflected beam brightness can be employed for mapping in place of height level distribution, whereby distinction between the land existing region and the background surface can be attained with ease even in such a case. This however does not reflect the information on warping or the like surface regularities of the circuit board substrate. Thus, it is convenient to construct so that both the mapping image of height level distribution and the mapping image of reflected beam brightness can be used according to the necessity (e.g., the both images can be displayed selectively by switching).

Figure 37B:
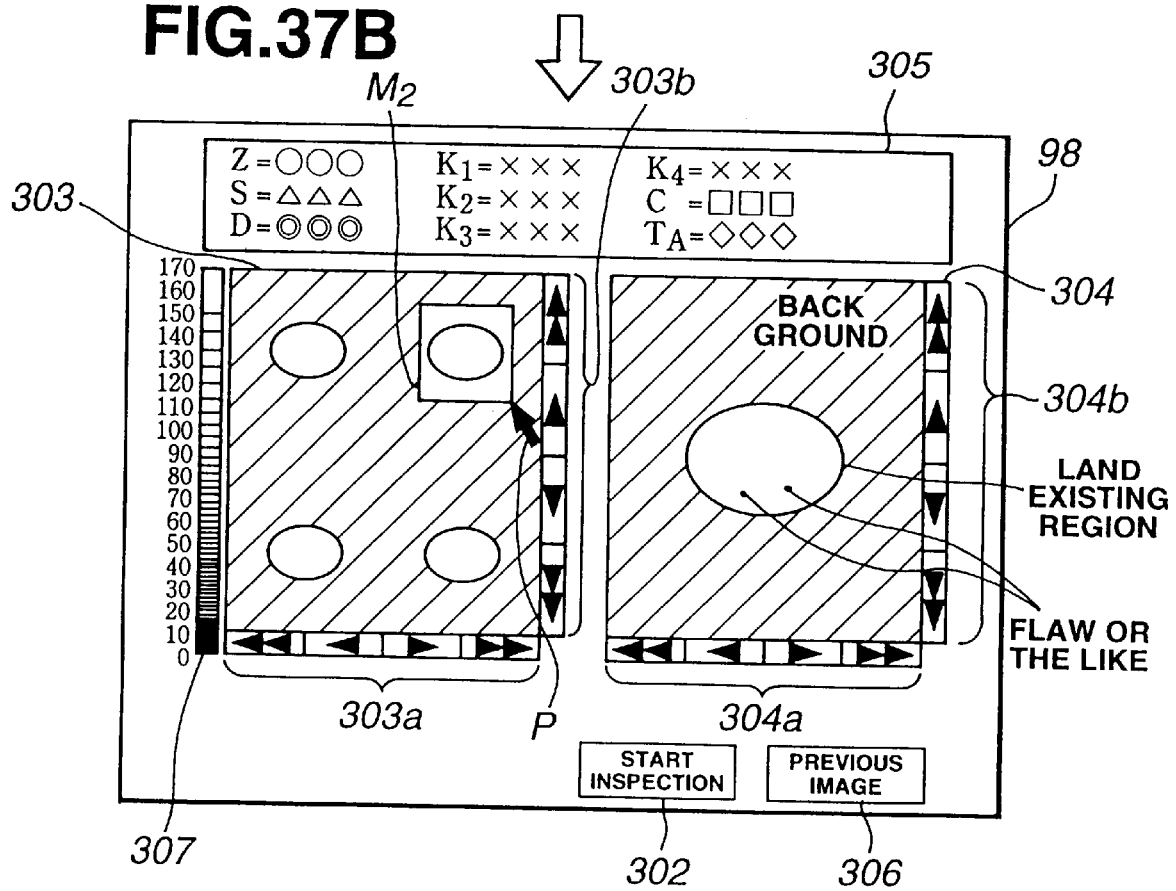

In the meantime, in FIGS. 37A and 37B, the data sampling distance in the y-direction is made larger than that in the x-direction, for thereby reducing in number the fetch data sets, while on the other hand the display on the screen is constructed so that the number of pixels per unit length so as to be the same both in the x-direction in which the sampling interval is dense and in the y-direction in which the sampling interval is course, so the silhouette region and the land existing region corresponding to each land appears in the form of an oval shape which is contracted in the y-direction. However, by making larger the magnification of display in the y-direction, it becomes possible to attain a circular display form corresponding to an original land plane figure.

In the meantime, as shown in FIG. 37B, in order to enable, for either of the first window 303 and the second window 304, scroll of a mapping image within the window, there are provided scroll buttons 303a, 303b, 304a and 304b which are operated by mouse click by way of a pointer P, for the purpose of convenience of an operator who makes reference to the condition around the defective land. Further, it is displayed a height level scale 307 which represents a relation between the display color of the respective regions on the mapping image and the height level.

Figure 38A:
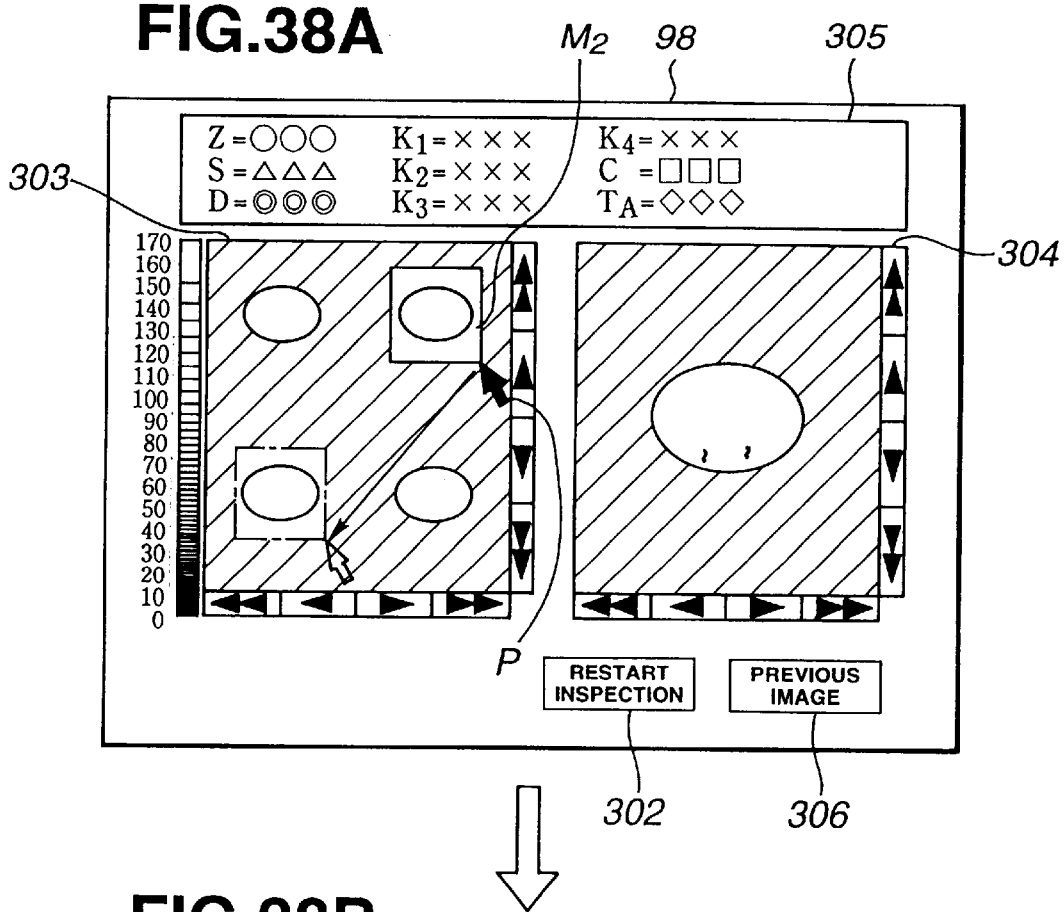
FIGS. 38A and 38B are illustrations of an operation for moving an enlarged display region and display of data by clicking a pixel on a mapping image.
Figure 38B:
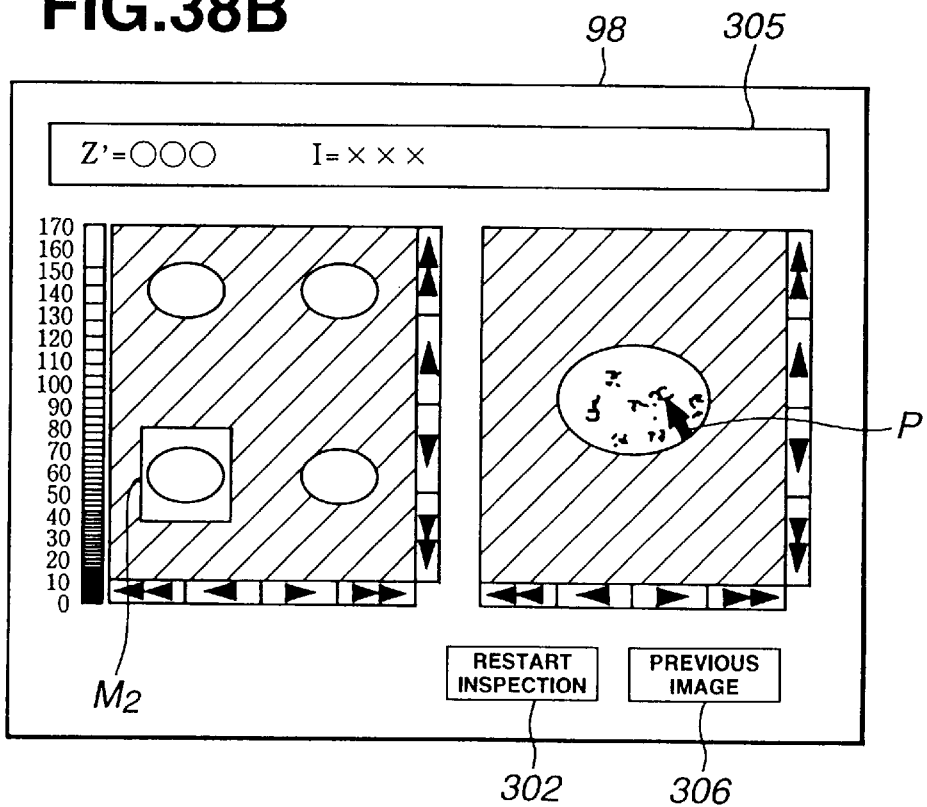

Further, as shown in FIGS. 38A and 38B, it is adapted that the marker M2 within the first window 303 can be moved into a position on the mapping image, where the marker surrounds a desired land, by a drawing operation of the mouse 100b (FIG. 5). Though such a drawing operation is a known technique, it can be carried according to the following process. Firstly, the position indicated by the pointer P is positioned within the marker M2 by the operation of the mouse. Under this condition, by pushing a mouse button which is not shown, it is established a condition where the marker M2 is selected. Then, by moving the mouse with its button being held pushed, an image display processing is performed so as to allow the marker M2 to move following the pointer P. When the marker M2 is moved into a desired land region, the mouse button is released, whereby the marker M2 is placed at that position and definitely held thereat.

As the marker M2 moves, an enlarged mapping image of an area indicated by the marker M2 having moved or having shifted its position is displaced within the second window 304. By this, a mapping image of a desired region within the first window 303 (i.e., a desired land) can be displaced while enlarging it.

Further, it is adapted that, as shown in FIG. 38B, in the enlarged image within the second window 304 (individual land selection region), the pixels corresponding to the respective data sets can be selected by means of the pointer P individually. This selection can be executed by, for example, placing the position indicated by the pointer P upon a desired pixel position and performing mouse click. By this operation, there is displayed within the third window 305 the height value Z' and the reflected beam brightness I which are read from the corrected data memory section 94b in FIG. 5 or FIG. 12B (P3009–P3011 in FIG. 47).

In the meantime, on the display image of the monitor 98 shown in FIG. 37B, there is formed a previous image selecting button 306. By operating this button, a previous or preceding image command is executed to enable returning to the image shown in FIG. 42A at any time (P3008, P3012 in FIG. 47). Further, each display image is formed with an inspection restart or resuming button 302. By performing mouse click of this button, a command to restart inspection is executed (P3013–P3015 in FIG. 47), and at P3016 an instruction to restart inspection is transmitted to the measurement system control section 51 to finish the defect display process in FIG. 47. At the same time, the height level distribution display process in FIG. 45 is finished, and the process returns to P50 in FIG. 43. The process onward is the same as that for the normal work. In the meantime, when the measurement system control section 51 receives an instruction to restart inspection at D54 in FIG. 49, it is released from the processing suspension/standby condition at D53 to restart the process onward.

Figure 36B:
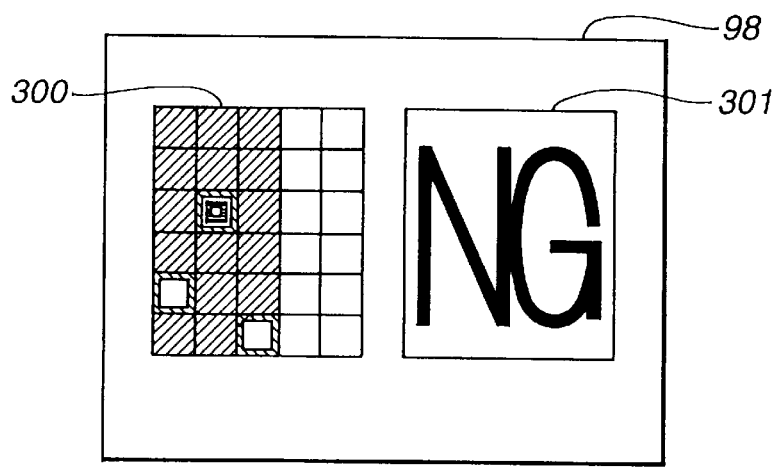

The works 1 on the work holder 38 are subjected to the above described judgment result display process in FIG. 43 (P30 and P40) in order as having finished the data analysis/ inspection judgment process in FIG. 24. When the above processing of all of the works 1 on the holder is completed, the process is finished. In the meantime, it will do to continue the operation of the measurement system 10 at the time of detection of a defective work without suspending it and give only a warning of occurrence of defect. For example, it can be done, as shown in FIG. 36B, that the display within the height level distribution value display window 301 is cleared and in place therefor a message (NG) indicating occurrence of defective work, or the like is displayed. Further, it will do to make a speaker (not shown) produce a warning sound. In this instance, the defect display process of FIG. 47 is executed by reading, after the inspection has been completed, a set of height level value and position data (FIG. 12B) and an inspection result data (FIG. 19) of a desired work.

Figure 39:
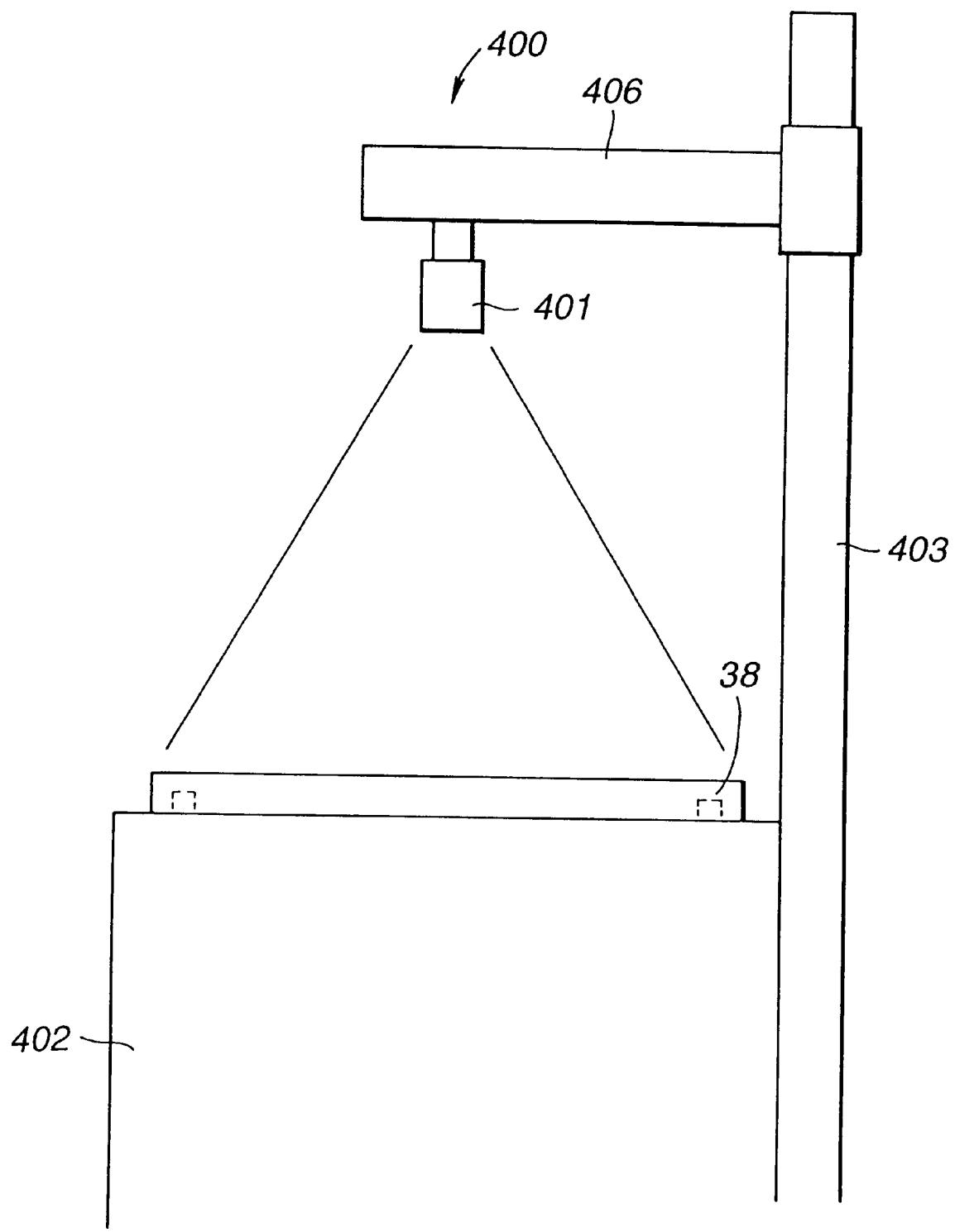
FIG. 39 is a schematic side elevation of a sorting unit.

The work holder 38 having finished the inspection is removed from the x-y table 40 (FIG. 4) and is mounted on a sorting unit 400 shown in FIG. 39. The sorting unit 400 consists of a light source box 402 on which the work holder 38 can be detachably mounted, and a CCD camera 401 attached to the light source box 402 by means of a vertical support post 403 and a horizontal arm 406.

FIG. 40 shows an internal structure of the light source box 403. The light source box 403 includes a box main body 402' having an opening 402'b on the upper surface side, and a light source 404 such as a fluorescent lamp disposed within the box main body 402'. The work holder 38 is position on the upper surface of the box main body 402' and attached thereto by allowing protruded engagement portions 402'a formed on the box main body 402' side to engage in engagement holes 38d formed in the work holder 38 so that the regions for arrangement of the respective works are positioned inside the opening 402'b. In the meantime, at a predetermined position on the upper surface side of the box main body 402', there is disposed a work holder orientation detecting sensor 405 which is constituted by a proximity switch or the like. On the other hand, at a predetermined position on the lower surface side of the work holder 38 which is made of, for example, a resinous material, there is disposed a detected metal piece 38s. Only when the work holder 38 is mounted on the box main body 402' in such a manner that its orientation relative to the box main body 402' is correct, i.e., in such a manner as to face correctly relative to the box main body 402', the detected metal piece 38s is detected by the work holder orientation detecting sensor 405, whereby it can be detected whether the orientation of the mounted work holder 38 is correct or not.

FIG. 41 shows is a block diagram of an electrical structure of the sorting unit 400. Its control portion 450 includes an I/O port 449, and a CPU 451, RAM 452 and ROM 453 which are connected to the I/O port 449, as major components. To the I/O port 449 are connected a sensor output control section 411, camera output control section 412, monitor control section 413, D/A converter 414, memory 454 such as a hard disk, the computer 82 of the data analysis section 81 and the central control unit 52 of the measurement control section 51. To the sensor output control section 411 is connected the work holder orientation detecting sensor 405. To the cameral output control section 412 is connected the above described CCD camera 401. To the monitor control section 413 is connected is a monitor 410 which serves as a work good/no good judgment result display means. To the D/A converter 414 is connected by way of an amplifier 415 a speaker 416 which serves as a warning output means. In the meantime, the CPU 451 functions as a measurement system operation control means on the basis of a control program 454a stored in the memory 454.

Hereinafter, the operation of the sorting unit 400 will be described by using the flowchart of FIG. 48. Firstly, at Q101, the inspection result data corresponding to the respective works 1 of the work holder 38 to be mounted, is received from the computer 82 of the data analysis section 81. At Q102–Q103, judgment on the orientation of the mounted work holder 38 is made on the basis of the detection output of the work holder orientation detecting sensor 405. When the orientation is incorrect, a warning sound is produced by the speaker 416.

Then, at Q105, a judgment result display window 460 is displayed, as shown in FIG. 42A, on the monitor 410 on the basis of the received inspection judgment result and in nearly the same format as the judgment result display window 300 already shown in FIGS. 36A and 36B. By this, the position of a defective work on the work holder 38 can be recognized. At the same time, at Q106, an operation suspending instruction (or operation inhibiting instruction) is transmitted to the central control unit 52 of the measurement system control section 51 for suspending the process when the measurement of that work holder is finished even though there is a new work holder installed on the x-y table of the measurement system 10.

Figure 42B:
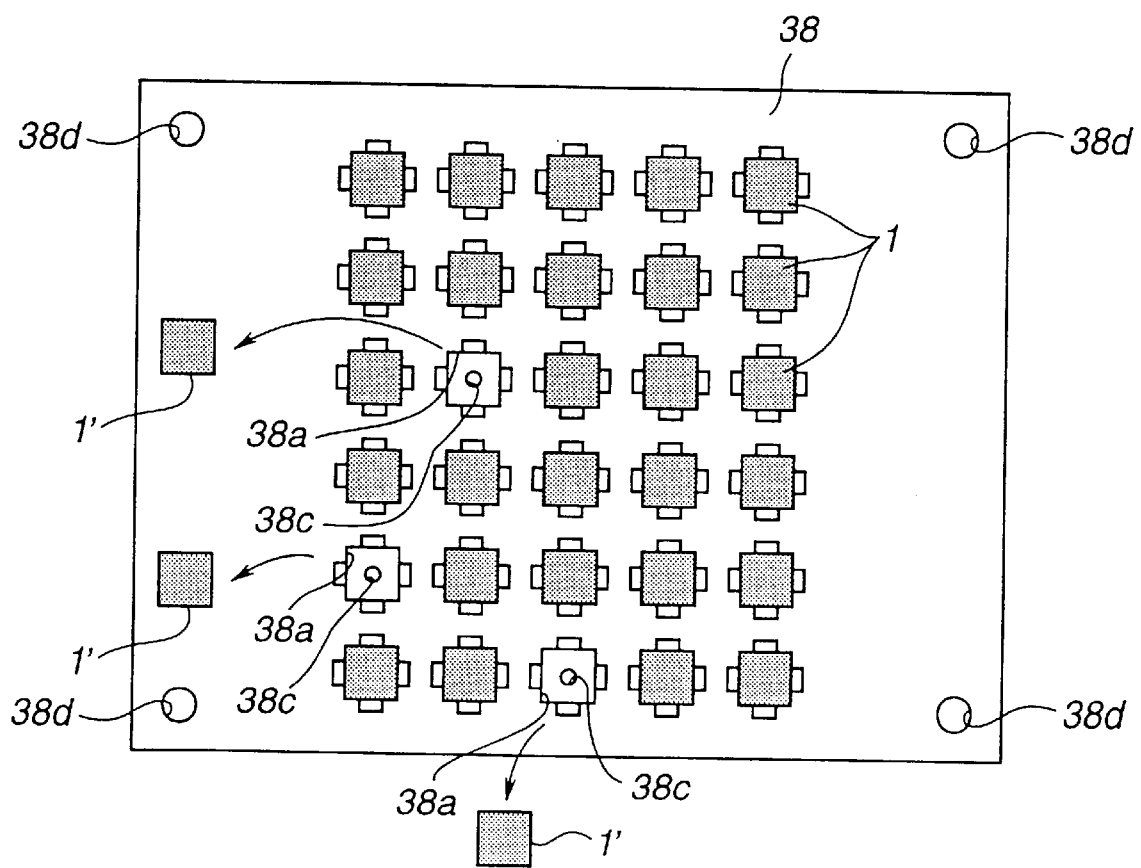

The operator removes manually or by hand a defective work from the work holder 38 as shown in FIG. 42B while looking at the judgment result display window 460 on the monitor 410. Then, as shown in FIG. 40, at the depression 38a from which a work is removed, a light from the light source 404 penetrates the through hole 38c to leak to the upper side of the work holder 38 and is detected by the CCD camera 401 (FIG. 39). In this connection, since it is already known which one of the works 1 on the work holder 38 is defective, so judgment on whether all of the defective works are removed correctly can be done by reference to whether leaking light is detected at the positions corresponding to the defective works and at the same time the leaking light is not detected at the positions corresponding to all of the normal works.

Figure 48:
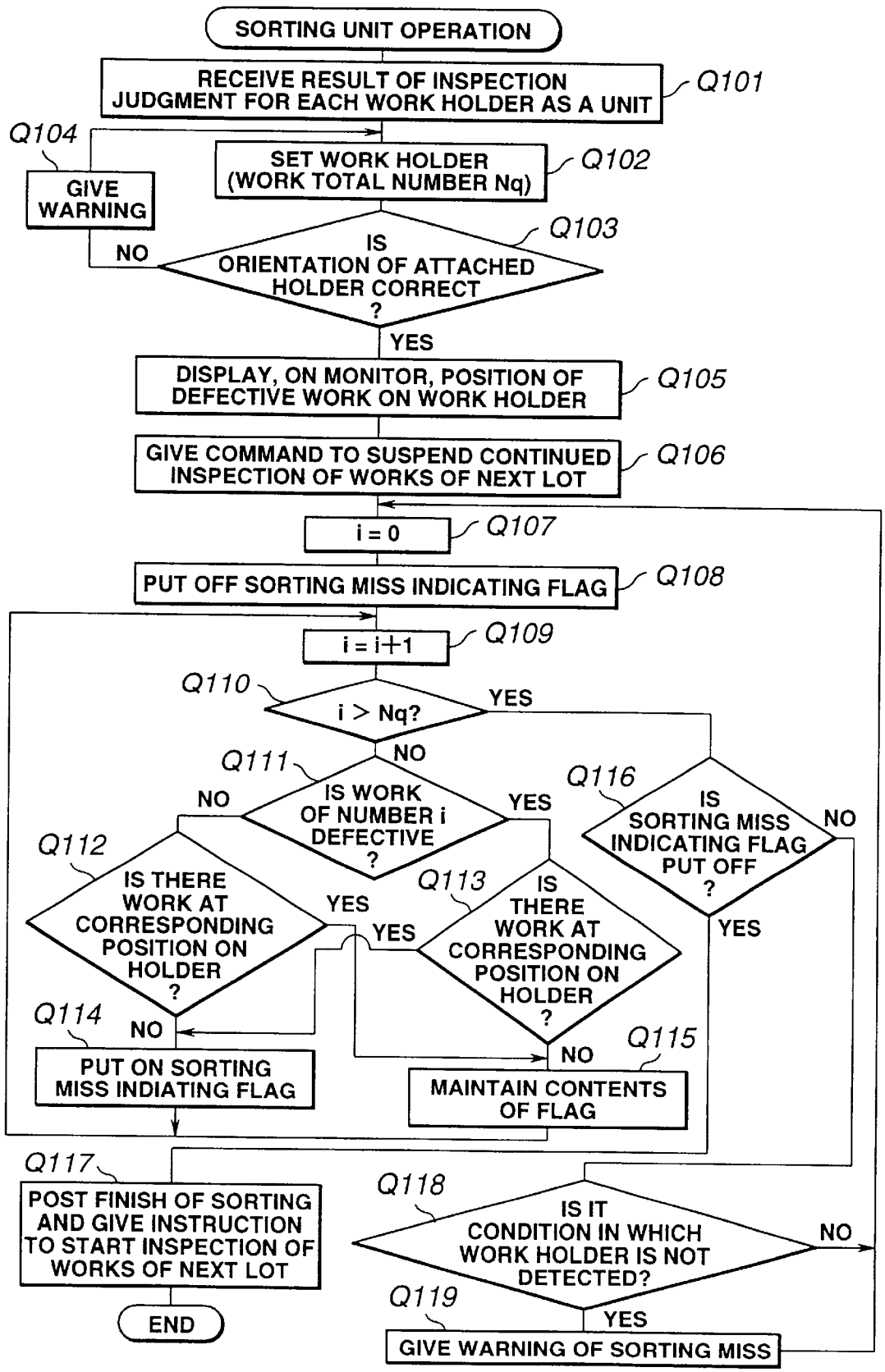
FIG. 48 is a flowchart of an operation of the sorting unit of FIG. 39.

In the process of FIG. 48, a check on whether leaking light is detected is made sequentially at the respective work mounted positions, while at the same time if there is an inconsistency about a leaking light detected condition, a sorting miss indicating flag 452a formed in the RAM 452 is put on. This process steps are repeated until the inconsistency about leaking light detected condition is eliminated, i.e., until a condition where the sorting miss indicating flag 452a is put off at the time when a check at all of the work mounted positions is finished, is obtained (Q108–Q116). When such a condition is obtained, the process proceeds to step Q117 where it is made to post finish of sorting, and an instruction to allow operation is transmitted to the central control unit 52 of he measurement control section 51, and thereafter the process is finished. By this, it becomes possible for the measure system 10 to start inspection of the works of the next lot. On the other hand, in case the work holder orientation detecting sensor 405 is put into a condition of not detecting a work holder though the sorting miss indicating flag 452a is put on at Q116 (i.e., the work holder 38 is removed from the sorting unit 400), the process proceeds to step Q119 to give a warning by means of a warning sound produced by the speaker 416.

While the present invention has been described and shown as above, this is not for the purpose of limitation but various modifications and variation can be made thereto without departing from the appended claims.

For example, while the present invention has been described and shown as being applied to inspection of a flip-chip circuit board, it can be applied to another kind of circuit boards so long as it has lands.

What is claimed is:
1. An apparatus for inspecting a circuit board with a plurality of lands disposed on one side of a circuit board substrate two-dimensionally, which side has at a place other than a place provided with the lands, an exposed portion constituting a background surface which is different in reflectance from a surface of each of the lands, the apparatus comprising a measurement system including:

a beam source for supplying an inspection beam obliquely onto an inspection surface of the circuit board, said inspection surface including a surface region where the lands are disposed;

a beam receiving section for receiving a reflected beam resulting from the inspection beam and reflected from the inspection surface, and producing a detection output which varies according to a reflected beam brightness and a reflected beam received position at said beam receiving section;

beam scanning means for scanning the beam within the inspection surface two-dimensionally;

height level information preparing means for preparing height level information which is information on height level at respective positions within the inspection surface, on the basis of the detection output indicative of the reflected beam received position at said beam receiving section; and reflected beam brightness information preparing means for preparing reflected beam brightness information which is information on reflected beam brightness at respective positions on the inspection surface on the basis of the detection output of said beam receiving section;

the apparatus further comprising:

land existing region fixing means for fixing, within the inspection surface, land existing regions where the respective lands exist, on the basis of the difference in the reflected beam brightness represented by the reflected beam brightness information, between the background surface and the surface of each of the lands;

inspection information preparing means for preparing inspection information including land height level information which is information relating to surface height levels of the respective lands, on the basis of the height level information at respective positions within the land existing regions fixed by the land existing region fixing means; and inspection information output means for outputting the inspection information prepared by said inspection information preparing means;

wherein said inspection information preparing means comprises land center calculating means for calculating a center of each of the land existing regions and determining the calculated center as a center of a corresponding one of the lands, and land arranging interval calculating means for calculating a land arranging interval on the basis of a distance between the centers of the lands calculated by said land center calculating means.

2. An apparatus according to claim 1, wherein said substrate is made of a low reflectance material whose outer surface is lower in reflectance with respect to the inspection beam than the surface of each of the lands, and said land existing region fixing means fixes said land existing regions by regarding, within the inspection surface, regions which enable detection of a reflected beam brightness equal to or higher than a predetermined threshold value which is set so as to be higher than a reflected beam brightness level at a surface of the low reflectance material, as said land existing regions.

3. An apparatus according to claim 2, wherein said low reflectance material is one of a high polymer material and a ceramic material.

4. An apparatus according to claim 1, wherein said substrate is made of a high reflectance material whose outer surface is higher in reflectance with respect to the inspection beam than the surface of each of the lands, and said land existing region fixing means fixes said land existing regions by regarding, within the inspection surface, regions which enable detection of a reflected beam brightness equal to or lower than a predetermined threshold value which is set so as to be lower than a reflected beam brightness level of the outer surface of the low reflectance material, as said land existing regions.

5. An apparatus according to claim 4, wherein said high reflectance material is one of a high polymer material and a ceramic material.

6. An apparatus according to claim 1, wherein said inspection information preparing means comprises land height level calculating means for calculating the land height levels on the basis of the height level information at respective positions within the land existing regions, said land height level calculating means calculating one of an average height level which is obtained by averaging height levels at respective positions within each of the land existing regions, a maximum height level which is a maximum of the height levels at said respective positions, a minimum height which is a minimum of the height levels at said respective positions and a most frequent height which is the most numerous one of the height levels at said respective positions, and determines calculated one of them as a height level of corresponding one of the lands.

7. An apparatus according to claim 6, wherein:
the inspection beam is cast onto the inspection surface while holding the circuit board in place by means of a circuit board holder;
said height level calculating means calculates a height level of each of the lands above a reference height level having a constant relation with a circuit board holder and determines the calculated height level as said height level of corresponding one of the lands; and
said inspection information preparing means includes coplanarity information preparing means for preparing coplanarity information reflecting an irregularity of heights of the lands of the circuit board, on the basis of a maximum Z'max and a minimum Z'min of the height levels calculated by said land height level calculating means.

8. An apparatus according to claim 1, wherein said inspection information preparing means prepares land size information reflecting an area and/or other dimensions of each of the lands on the basis of an area and/or other dimensions of corresponding one of the land existing regions.

9. An apparatus according to claim 1, wherein said land center calculating means calculates a geometric center of gravity of each of the land existing regions and determines the calculated geometric center as the center of corresponding one of the lands.

10. An apparatus to claim 1, wherein said land center calculating means calculates a point of intersection of diagonal lines of a quadrilateral region circumscribed about each of the land existing regions and determines the calculated point of intersection as the center of corresponding one of the lands.

11. An apparatus according to claim 1, wherein said inspection information preparing means comprises land defect information preparing means for preparing information reflecting a defect within each of the land existing regions, on the basis of said reflected beam information at respective positions within the land existing regions.

12. An apparatus according to claim 1, further comprising:
background height level determining region setting means for setting, at locations outside of the respective land existing regions, background height level determining regions for obtaining the height level of the background surface around each of the lands; and
background height level calculating means for calculating a height level of each of the lands on the basis of the information on height level at respective positions within each of the background height level determining regions;
said inspection information preparing means including surface waviness information preparing means for preparing surface waviness information reflecting a waviness condition of the background surface on the basis of the height levels, which height levels are calculated by said background height level calculating means, of the background surface at the background height level determining regions which are set at different positions on the inspection surface.

13. An apparatus according to claim 1, wherein said inspection information output means comprises height level distribution display means for causing a display device to produce a mapping output representing a height level distribution on the inspection surface by dividing a range of height level by one or more threshold values and associating divided range sections of height level with respective depths and/or colors of each of pixels of the display device one to one for thereby associating depths and/or colors of pixels corresponding to the respective positions on the inspection surface with height levels at the respective positions, which are indicated by said height level information.

14. An apparatus according to claim 13, further comprising:
land quality judging means for judging good/no good of each of the lands on the basis of whether the formed condition of each of the lands, which formed condition reflects on said inspection information, satisfies a predetermined judgement condition or not; and
defective land position display control means for controlling so that said display device displays an existing position of a defective land which is judged, on a mapping output display of said height level distribution, as being defective by said land quality judging means.

15. An apparatus according to claim 14, further comprising:
defective land existing region selecting means for selecting, on the mapping output display of the height level distribution, the existing region of the defective land whose position is indicated; and
defective land existing region enlarged display means for displaying an enlarged mapping image of a height distribution of the selected defective land existing region.

16. An apparatus according to claim 13, further comprising:
a work holder for detachably holding thereon a plurality of works which are arranged on a plane, each of the works being a land-attached circuit board which is an object for inspection; and
work holder drive means for driving said work holder to move relative to the beam source for thereby moving the arranged works sequentially into an inspection position to which the inspection beam is cast;
wherein said measurement system performs detection of height level at respective positions within an inspection surface of each of the works which are moved into the inspection position, and said inspection information preparing means prepares inspection information of each of the works on the basis of corresponding one of said height level information.

17. An apparatus according to claim 16, further comprising:
work arrangement display means for displaying arrangement of the works on the work holder;
work quality judging means for judging good/no good of each of the works on the basis of said inspection information; and
defective work display control means for controlling said work arrangement display means and making it display, in relation to the arrangement of the works, a position of a defective work which is judged as having a defective land or lands by means of said work quality judging means.

18. An apparatus according to claim 16, further comprising measurement system operation control means for suspending measurement operation of said work holder drive means and said measurement system in case a work is judged as being defective by said work quality judging means in the middle of detection of the height level at the respective positions within the inspection surface, which is carried out sequentially for the works.

19. An apparatus according to claim 16, further comprising:
work quality judgment result display means for displaying a result of judgment on whether each of the works on he work holder is a defective work or normal work;
work detecting means for detecting individually whether the works are attached to respective work attaching positions on the work holder;
sorting result judging means for judging whether a work sorting operation is carried out correctly or not, on the basis of a detection content of said work detection means with respect to the work holder which is subjected to a work sorting operation for removing a defective work and leaving a normal work, while looking at a display content of said work quality judgment result display means; and
judgment result output means for outputting a result of judgment by said sorting result judging means.

20. An apparatus according to claim 19, wherein said work detecting means detects whether the works are attached to the work attaching positions, with respect to the work holder in a state of being removed from said measurement system, and the apparatus further comprising measurement system operation control means for controlling said work holder drive means and said measurement system in a way as to inhibit them from performing a measurement operation for a next work holder, in response to an output of said judgment result output means in case the work sorting operation is not carried out correctly.

21. An apparatus according to claim 1, wherein said apparatus detects both the height and existing position of a land or pattern.

22. An apparatus according to claim 1, wherein said beam source is a single laser beam.

23. An apparatus according to claim 1, wherein said apparatus utilizes a position sensitive detector for determining the position of the land or pattern.

24. An apparatus according to claim 1, wherein said apparatus utilizes a laser beam for detecting height.

25. An apparatus according to claim 1, wherein said apparatus detects both the height and existing position of a land or pattern.

26. An apparatus according to claim 25, wherein said beam source is a single laser beam.

27. An apparatus according to claim 26, wherein said apparatus utilizes a position sensitive detector for determining the position of the land or pattern.

28. An apparatus according to claim 27, wherein said apparatus utilizes a laser beam for detecting height.

29. An apparatus for inspecting a circuit board with a plurality of lands disposed on one side of a circuit board substrate two-dimensionally, which side has at a place other than a place provided with the lands an exposed portion constituting a background surface which is different in reflectance from a surface of each of the lands, the apparatus comprising a measurement system including:
a beam source for supplying an inspection beam obliquely onto an inspection surface of the circuit board, said inspection surface including a surface region where the lands are disposed;
a beam receiving section for receiving a reflected beam resulting from the inspection beam and reflected from the inspection surface, and producing a detection output which varies according to a reflected beam brightness and a reflected beam received position at said beam receiving section;
beam scanning means for scanning the beam within the inspection surface two-dimensionally;
height level information preparing means for preparing height level information which is information on height level at respective positions within the inspection surface, on the basis of the detection output indicative of the reflected beam received position at said beam receiving section; and
reflected beam brightness information preparing means for preparing reflected beam brightness information which is information on reflected beam brightness at respective positions on the inspection surface on the basis of the detection output of said beam receiving section;
the apparatus further comprising:
land existing region fixing means for fixing, within the inspection surface, land existing regions where the respective lands exist, on the basis of the difference in the reflected beam brightness represented by the reflected beam brightness information, between the background surface and the surface of each of the lands;
inspection information preparing means for preparing inspection information including land height level information which is information relating to surface height levels of the respective lands, on the basis of the height level information at respective positions within the land existing regions fixed by the land existing region fixing means; and inspection information output means for outputting the inspection information prepared by said inspection information preparing means;

wherein each of said land existing regions is fixed by means of an image which is displayed by collective pixels disposed on a pixel plane corresponding to said inspection surface, and a master image corresponding in shape to each of the land existing regions and reflecting an area and/or other dimensions of each of the land existing regions is prepared; and wherein said inspection information preparing means includes land center calculating means for selecting a position of said master image on the basis of the number of pixels which correspond to only one of said image of each of said land existing regions and said master image and calculating a geometric center of gravity of said master image at the selected position and determining the calculated geometric center of gravity as a center of corresponding one of the lands.

30. An apparatus according to claim 29, wherein said inspection information preparing means comprises land arranging interval calculating means for calculating a land arranging interval on the basis of a distance between the centers of the lands calculated by said land center calculating means.

31. An apparatus for inspecting a circuit board with a plurality of lands disposed on one side of a circuit board substrate two-dimensionally, which side has at a place other than a place provided with the lands an exposed portion constituting a background surface which is different in reflectance from a surface of each of the lands, the apparatus comprising a measurement system including:

a beam source for supplying an inspection beam obliquely onto an inspection surface of the circuit board, said inspection surface including a surface region where the lands are disposed;

a beam receiving section for receiving a reflected beam resulting from the inspection beam and reflected from the inspection surface, and producing a detection output which varies according to a reflected beam brightness and a reflected beam received position at said beam receiving section;

beam scanning means for scanning the beam within the inspection surface two-dimensionally;

height level information preparing means for preparing height level information which is information on height level at respective positions within the inspection surface, on the basis of the detection output indicative of the reflected beam received position at said beam receiving section; and reflected beam brightness information preparing means for preparing reflected beam brightness information which is information on reflected beam brightness at respective positions on the inspection surface on the basis of the detection output of said beam receiving section;

the apparatus further comprising:

land existing region fixing means for fixing, within the inspection surface, land existing regions where the respective lands exist, on the basis of the difference in the reflected beam brightness represented by the reflected beam brightness information, between the background surface and the surface of each of the lands;

inspection information preparing means for preparing inspection information including land height level information which is information relating to surface height levels of the respective lands, on the basis of the height level information at respective positions within the land existing regions fixed by the land existing region fixing means; and inspection information output means for outputting the inspection information prepared by said inspection information preparing means;

wherein each of said land existing regions is fixed by means of an image which is displayed by collective pixels disposed on a pixel plane corresponding to said inspection surface, and a master image corresponding in shape to each of the land existing regions and reflecting an area and/or other dimensions of each of the land existing regions is prepared;

wherein each of said image of each of said land existing regions and said master image is formed by a combination of a plurality of substantial or imaginary pixels in output states, the pixels being capable of being set to an intermediate output; and wherein said inspection information preparing means includes land center calculating means for selecting a position of said master image on the basis of the sum of difference in set output value between corresponding pairs of the pixels of said image of each or said land existing regions which is an object to be inspected and said master image and calculating a geometric cent of gravity of said master image at the selected position and determining the calculated geometric center of gravity as a center of corresponding one of the lands.

32. An apparatus according to claim 31, wherein said inspection information preparing means comprises land arranging interval calculating means for calculating a land arranging interval on the basis of a distance between the centers of the lands calculated by said land center calculating means.

* * * * *